US011904067B2

(12) United States Patent
Zhao et al.

(10) Patent No.: US 11,904,067 B2
(45) Date of Patent: Feb. 20, 2024

(54) DRY DOUBLE-SIDED MATERIAL FOR ADHESION OF WET TISSUES AND DEVICES

(71) Applicant: Massachusetts Institute of Technology, Cambridge, MA (US)

(72) Inventors: Xuanhe Zhao, Allston, MA (US); Hyunwoo Yuk, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 749 days.

(21) Appl. No.: 16/846,293

(22) Filed: Apr. 11, 2020

(65) Prior Publication Data

US 2020/0353120 A1    Nov. 12, 2020

Related U.S. Application Data

(60) Provisional application No. 62/845,976, filed on May 10, 2019.

(51) Int. Cl.
*A61L 24/00* (2006.01)
*A61B 5/00* (2006.01)
(Continued)

(52) U.S. Cl.
CPC ........ *A61L 24/0031* (2013.01); *A61B 5/1102* (2013.01); *A61B 5/68335* (2017.08);
(Continued)

(58) Field of Classification Search
CPC ............... A61L 24/0031; A61L 24/043; A61F 2013/00676
See application file for complete search history.

(56) References Cited

U.S. PATENT DOCUMENTS 5,704,905 A * 1/1998 Jensen .................. A61F 13/025
602/42
2003/0035786 A1    2/2003 Hendriks et al.
(Continued)

FOREIGN PATENT DOCUMENTS

CN          101378791        1/2013
CN          103429268       12/2013
(Continued)

OTHER PUBLICATIONS

Chung, et al "Rapidly Cross-Linkable DOPA Containing Terpolymer Adhesives and PEG-Based Cross-Linkers for Biomedical Applications", Macromolecules, 2012.
(Continued)

*Primary Examiner* — Brooke Labranche
(74) *Attorney, Agent, or Firm* — Peter A. Nieves; Nieves IP Law Group, LLC

(57) ABSTRACT

Dry adhesive materials, particularly in the form of a film or tape, for adhering one or more wet surfaces comprising: (i) one or more hydrophilic polymers; (ii) one or more amine coupling groups, and (iii) one or more cross linkers. The dry adhesive material, when placed in contact with the one or more wet surfaces, absorbs liquid from the one or more wet surfaces, swells to form temporary crosslinking with the wet surface, and forms covalent crosslinking with the one or more wet surfaces.

16 Claims, 46 Drawing Sheets

(51) Int. Cl.
A61B 5/11 (2006.01)
A61K 9/70 (2006.01)
A61L 24/04 (2006.01)
B32B 9/02 (2006.01)
B32B 29/00 (2006.01)
A61F 13/00 (2006.01)

(52) U.S. Cl.
CPC .......... *A61K 9/7084* (2013.01); *A61L 24/043* (2013.01); *B32B 9/02* (2013.01); *B32B 29/002* (2013.01); *A61B 2562/0261* (2013.01); *A61F 2013/00676* (2013.01); *B32B 2307/7163* (2013.01); *B32B 2307/748* (2013.01); *B32B 2405/00* (2013.01); *B32B 2535/00* (2013.01)

(56) References Cited

U.S. PATENT DOCUMENTS

2007/0286891 A1  12/2007  Kettlewell et al.
2016/0325010 A1  11/2016  Liebler et al.

FOREIGN PATENT DOCUMENTS

| CN | 105813545 | 7/2016 |
| CN | 112791227 | 5/2021 |
| EP | 3449819 | 8/2021 |
| WO | 2017165490 | 9/2017 |
| WO | 2018150186 | 8/2018 |

OTHER PUBLICATIONS

Yuk, et al "Dry Double-Sided Tape for Adhesion of Wet Tissues and Devices", Nature vol. 575 2019.
Annabi, N., Yue, K., Tamayol, A. & Khademhosseini, A. Elastic sealants for surgical applications. European Journal of Pharmaceutics and Biopharmaceutics 95, 27-39 (2015).
Yuk, H., Lu, B. & Zhao, X. Hydrogel bioelectronics. Chemical Society Reviews, doi: 10.1039/C1038CS00595H (2018).
Karp, J. M. A Slick and Stretchable Surgical Adhesive. New England Journal of Medicine 377, 2092-2094 (2017)).
Li, J. et al. Tough adhesives for diverse wet surfaces. Science 357, 378-381 (2017)).
Ouyang, L. et al. Enhanced PEDOT adhesion on solid substrates with electrografted P (EDOT-NH2). Science Advances 3, e1600448 (2017)).
Yuk, H., Zhang, T., Lin, S., Parada, G. A. & Zhao, X. Tough bonding of hydrogels to diverse non-porous surfaces. Nature Materials 15, 190 (2016).
Yuk, H., Zhang, T., Parada, G. A., Liu, X. & Zhao, X. Skin-inspired hydrogel-elastomer hybrids with robust interfaces and functional microstructures. Nature Communications 7, 12028 (2016).
Wirthl, D. et al. Instant tough bonding of hydrogels for soft machines and electronics. Science Advances 3, e1700053 (2017)).
Rose, S. et al. Nanoparticle solutions as adhesives for gels and biological tissues. Nature 505, 382-385 (2014).
Boehler, C., Oberueber, F., Schlabach, S., Stieglitz, T. & Asplund, M. Long-term stable adhesion for conducting polymers in biomedical applications: IrOx and nanostructured platinum solve the chronic challenge. ACS Applied Materials & Interfaces 9, 189-197 (2016).
Boutry, C. M. et al. A stretchable and biodegradable strain and pressure sensor for orthopaedic application. Nature Electronics 1, 314-321 (2018)).
Sadekar, A. G. et al. Robust PEDOT films by covalent bonding to substrates using in tandem sol-gel, surface initiated free-radical and redox polymerization. Journal of Materials Chemistry 22, 100-108 (2012).
Yuk, H. & Zhao, X. A new 3d printing strategy by harnessing deformation, instability, and fracture of viscoelastic inks. Advanced Materials 30, 1704028 (2018)).
Lu, B. et al. Pure PEDOT:PSS hydrogel with extraordinary electrical, mechanical and swelling properties. under review (2018).
Venkatraman, S. et al. In vitro and in vivo evaluation of PEDOT microelectrodes for neural stimulation and recording. IEEE Transactions on Neural Systems Rehabilitation Engineering 19, 307-316 (2011).
Roche, E. T. et al. Soft robotic sleeve supports heart function. Science Translational Medicine 9, eaaf3925 (2017).
Darnell, M. C. et al. Performance and biocompatibility of extremely tough alginate/polyacrylamide hydrogels. Biomaterials 34, 8042-8048 (2013)).
Vakalopoulos, K. A. et al. Mechanical strength and rheological properties of tissue adhesives with regard to colorectal anastomosis: an ex vivo study. Annals of Surgery 261, 323-331 (2015).
Cui, X. T. & Zhou, D. D. Poly (3, 4-ethylenedioxythiophene) for chronic neural stimulation. IEEE Transactions on Neural Systems Rehabilitation Engineering 15, 502-508 (2007).
Green, R. A. et al. Substrate dependent stability of conducting polymer coatings on medical electrodes. Biomaterials 33, 5875-5886 (2012).
Lee, B. P., Messersmith, P. B., Israelachvili, J. N. & Waite, J. H. Mussel-inspired adhesives and coatings. Annual Review of Materials Research 41, 99-132 (2011)).
Yamagishi, K. et al. Tissue-adhesive wirelessly powered optoelectronic device for metronomic photodynamic cancer therapy, Nature Biomedical Engineering 3, 27-36 (2019)).
Reece, T. B., Maxey, T. S. & Kron, I. L. A prospectus on tissue adhesives. The American Journal of Surgery 182, S40-S44 (2001)).

* cited by examiner

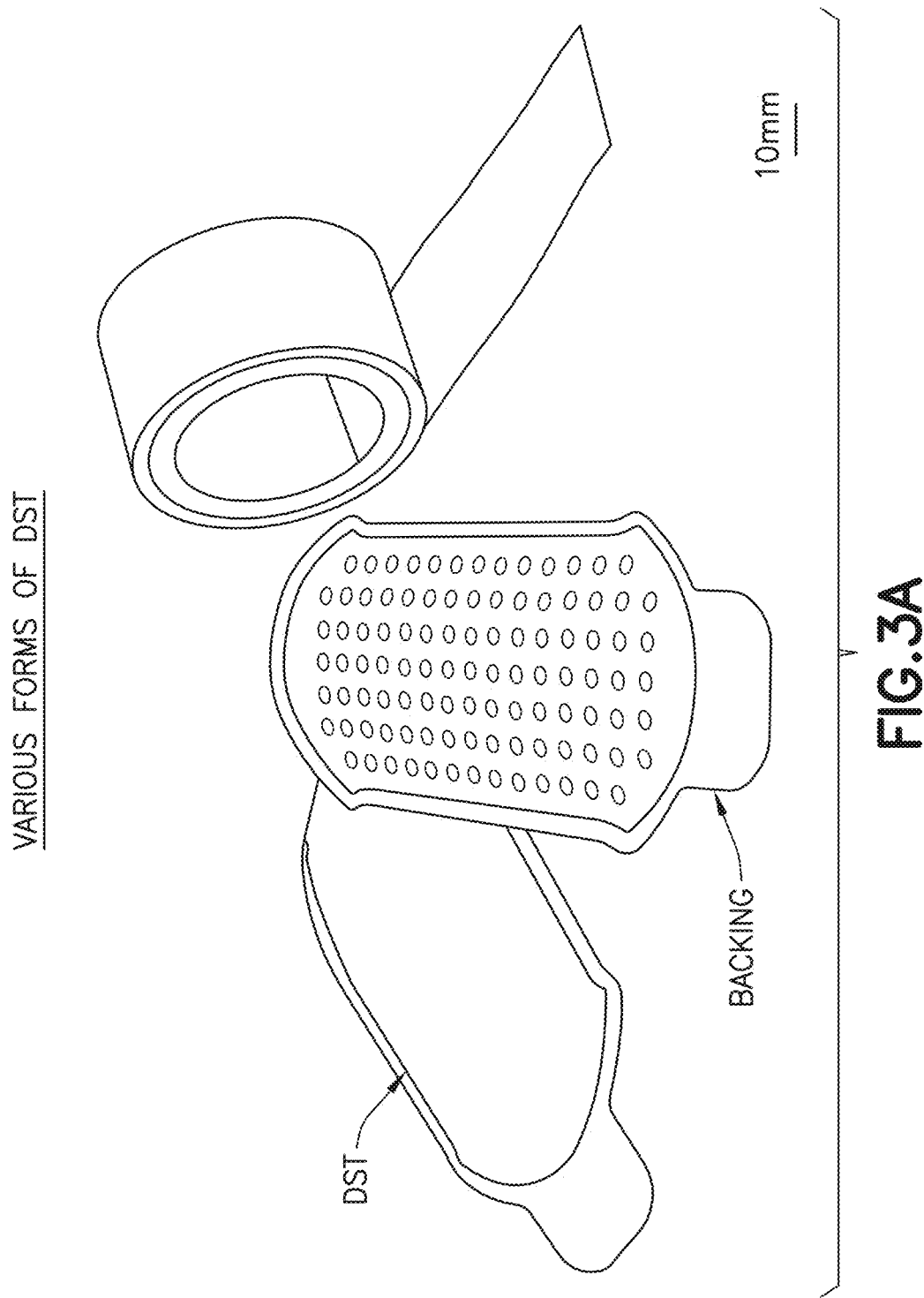

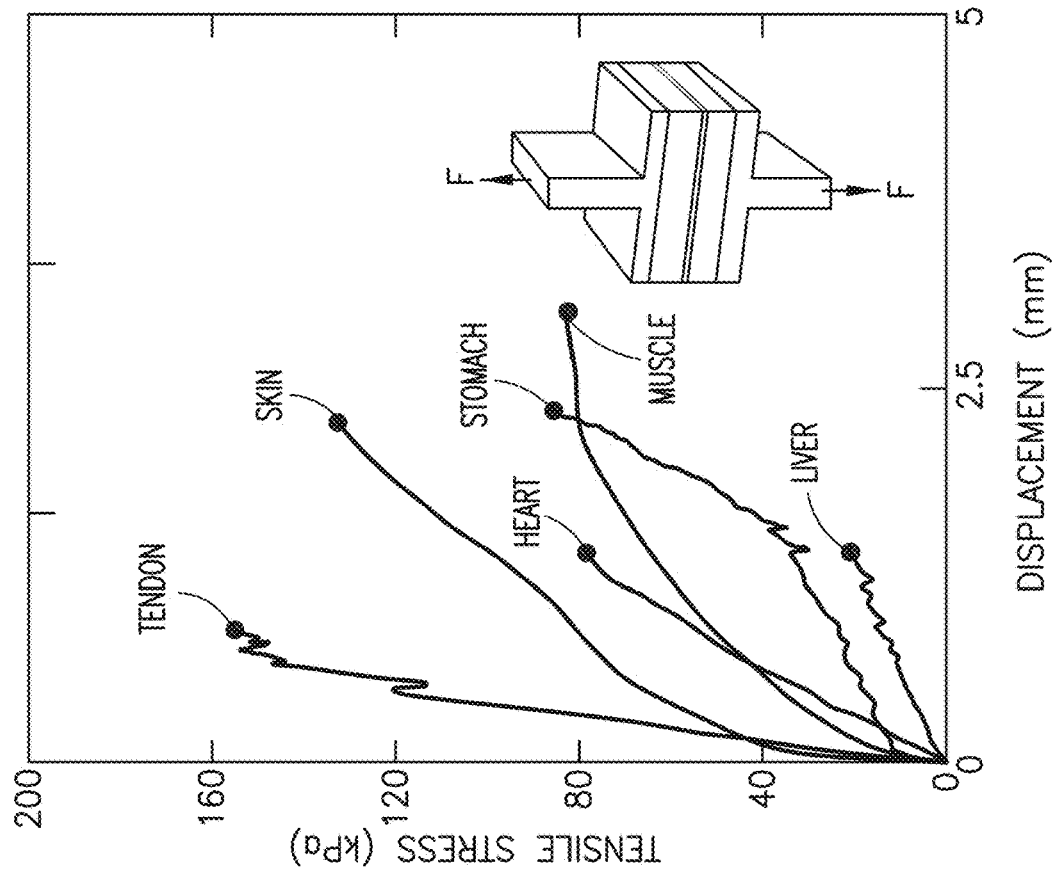
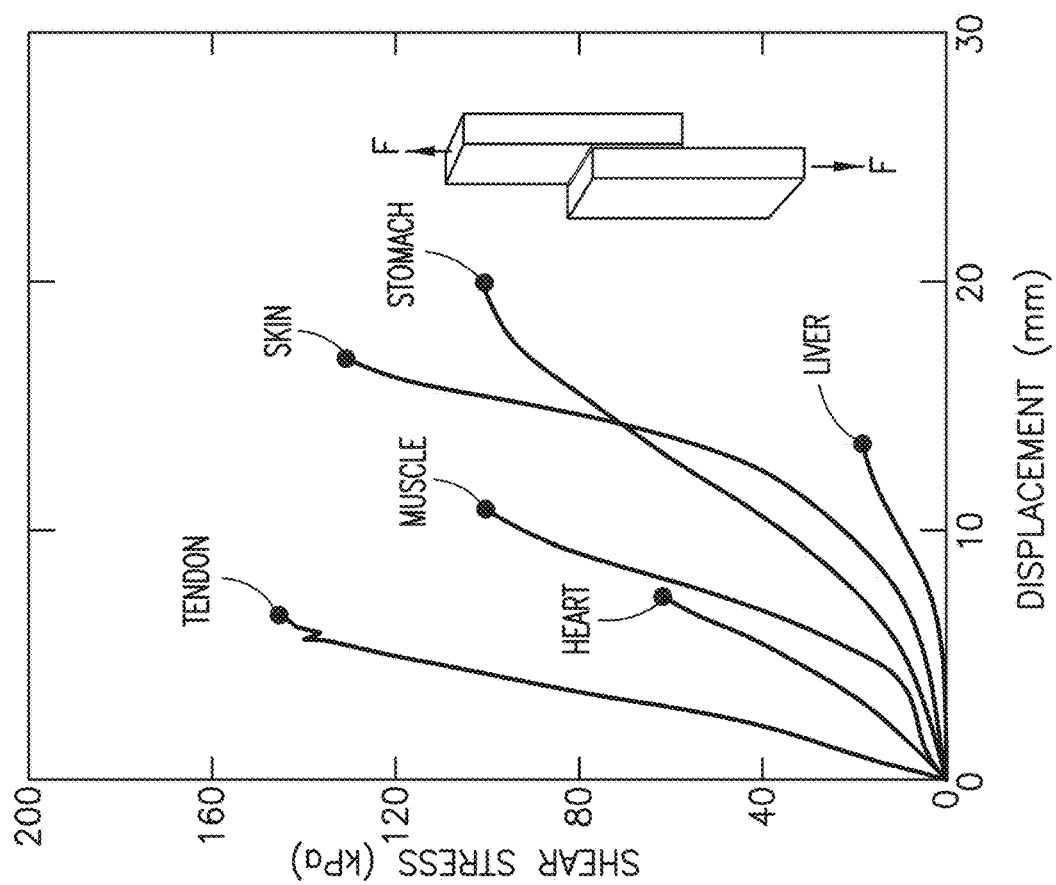
FIG. 14B
FIG. 14C

DRY DOUBLE-SIDED MATERIAL FOR ADHESION OF WET TISSUES AND DEVICES

CROSS-REFERENCE TO RELATED APPLICATIONS

This application claims the benefit of U.S. Provisional Application No. 62/845,976, filed on May 10, 2019. The entire teaching of the above application is incorporated herein by reference.

GOVERNMENT SUPPORT STATEMENT

This invention was made with Government support under Grant No. CMMI-1661627 awarded by the National Science Foundation (NSF). The Government has certain rights in the invention.

FIELD OF THE INVENTION

The present invention generally relates to materials and methods for adhering tissue, and more particularly to a dry double-sided material and methods for adhering wet tissues, particularly wherein the material is in the form of a flexible double-sided tape or film. According to preferred embodiments, the dry double-sided material includes a combination of one or more hydrophilic polymer, one or more amine coupling group, and one or more cross linkers.

BACKGROUND OF THE INVENTION

It is generally understood that two dry surfaces can instantly adhere upon contact with each other by intermolecular forces such as hydrogen bonds, electrostatic and van der Waals interactions. However, it is extremely challenging to form such instant adhesion between wet surfaces, such as biological tissues, because water separates molecules from the two surfaces to form instant interactions that impede adhesion between the surfaces.

Gluing wet surfaces, such as injured tissues, together or attaching devices onto wet surfaces have advantages over suturing or stapling. Existing tissue adhesives, mostly in the form of liquids or wet hydrogels, face many limitations including weak bonding, low biocompatibility, poor mechanical match with tissues, and slow adhesion formation. In particular, as depicted in FIGS. 1A-1B, such existing tissue adhesives rely on diffusion of their molecules (e.g., mono/macromers or polymers) into the polymer networks of the tissues for bonding, which can take significant time and provides weak adhesion, and wherein the presence of interfacial liquid between the adhesive and the tissues further interferes with the adhesion process.

For example, commercially available adhesives (e.g., fibrin glues, albumin-based adhesives, polyethylene glycol-based adhesives), nanoparticle solutions, and mussel-inspired adhesives exhibit slow adhesion formation (longer than 1 min) and weak adhesion on wet surfaces (interfacial toughness less than 20 J m$^{-2}$)(See Vakalopoulos, K. A. et al. Mechanical strength and rheological properties of tissue adhesives with regard to colorectal anastomosis: an ex vivo study. *Annals of Surgery* 261, 323-331 (2015); Rose, S. et al. Nanoparticle solutions as adhesives for gels and biological tissues. *Nature* 505, 382-385 (2014); Lee, B. P., Messersmith, P. B., Israelachvili, J. N. & Waite, J. H. Mussel-inspired adhesives and coatings. *Annual Review of Materials Research* 41, 99-132 (2011)). Cyanoacrylate adhesives have been found to further suffer from high cytotoxicity and inflexibility after curing (See Annabi, N., Yue, K., Tamayol, A. & Khademhosseini, A. Elastic sealants for surgical applications. *European Journal of Pharmaceutics and Biopharmaceutics* 95, 27-39 (2015); Karp, J. M. A Slick and Stretchable Surgical Adhesive. *New England Journal of Medicine* 377, 2092-2094 (2017)). Adhesion of bulk hydrogels on tissues having interfacial toughness on the order of 100 to 1,000 J m$^{-2}$ has been reported, but such hydrogels require prolonged pressure application of at least 10 min up to 30 min to form the adhesion (See Li, J. et al. Tough adhesives for diverse wet surfaces. *Science* 357, 378-381 (2017)). In addition, such bulk hydrogel adhesives are only capable of holding tissues together (see FIG. 1B), and are not capable of achieving adhesion directly between the tissue surfaces. In other words, the bulk hydrogel must be present between the two tissue surfaces in order to hold the tissue surfaces together. As such, removal of the hydrogel results in separation of the tissue surfaces.

Thus, the diffusion-based mechanism and the consequent limitations of existing tissue adhesive materials have severely hampered the success and scope of applications. In view of the great potential for tissue adhesives, improvements are greatly needed.

SUMMARY OF THE INVENTION

According to one aspect, the present invention provides a dry adhesive material for adhering one or more wet surfaces comprising: (i) one or more hydrophilic polymers; (ii) one or more amine coupling groups, and (iii) one or more cross linkers. The dry adhesive material is in the form of a film or tape having a top surface and a bottom surface. The dry adhesive material has a liquid content such that placement of one or more of the top and/or bottom surfaces of the dry adhesive material in contact with the one or more wet surfaces causes the dry adhesive material to absorb liquid from the one or more wet surfaces, swell to form temporary crosslinking between the dry adhesive material and the wet surface, and form covalent crosslinking between the one or more amine coupling groups and the one or more wet surfaces.

Embodiments according to this aspect can include one or more of the following features. The (i) one or more hydrophilic polymers can be selected from polyacrylic acid, polyacrylamide, polyvinyl alcohol, polyhydroxy ethyl methacrylate, polyethylene glycol, poly vinyl pyrrolidone, poly styrene sulfonate, casein, albumin, gelatin, collagen, chitosan, hyaluronic acid, alginic acid, oxidized alginate, pectin, and combinations thereof. The (ii) one or more amine coupling groups can be selected from N-hydroxysuccinimide ester, N-hydroxysulfosuccinimide ester, aldehyde, imidoester, epoxide, isocyanate, catechol, and combinations thereof. The (iii) one or more crosslinkers can be selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. The dry adhesive material can comprise poly(acrylic acid) grafted with N-hydroxysuccinimide ester, crosslinked by biodegradable gelatin methacrylate, and can further comprise one or more biodegradable biopolymers. The one or more biodegradable biopolymers can be selected from gelatin, chitosan, and combination thereof. Negatively charged carboxylic acid groups in the poly(acrylic acid) grafted with N-hydroxysuccinimide ester can facilitate absorption of liquid and swelling of the dry adhesive material and further form intermolecular bonds with the one or more wet tissue surfaces within less than 60 seconds after contact between the dry adhesive material and the one or more wet surfaces. The N-hydroxysuccinimide ester grafted in the poly(acrylic acid) can form covalent coupling with primary amine groups present on the one or more wet surfaces. After the covalent crosslinking is formed between the one or more amine coupling groups and the one or more wet surfaces, the swollen dry adhesive material can transform into a layer of a hydrogel. The hydrogel can have a fracture toughness of at least 1,000 J $m^{-2}$. The dry adhesive material can be in the form of a flat sheet, a perforated sheet, a double sided tape or film, and a perforated double sided tape or film. The dry adhesive material can have a top surface and a bottom surface, and can further comprise one or more backing material layers disposed on at least one of the top surface and bottom surface. The backing material can be a removable backing material fabricated of polyethylene, a hydrophobic polymer-coated paper, poly(methyl methacrylate), a hydrophobic polymer film, or combinations thereof. The backing material can be a non-removable material layer fabricated of silicone elastomer, thermoplastic polyurethane, hydrogel, a biocompatible material that is non-adhesive to wet tissues, or combinations thereof. The dry adhesive material can further comprise one or more engineering solids, and/or devices adhered to one or more surfaces of the dry adhesive material. The one or more engineering solids can be selected from hydrogel, silicon, titanium, polydimethylsiloxane, polyimide, polycarbonate, and combination thereof. The dry adhesive material can be biodegradable. The (i) one or more polymers and/or the (iii) one or more crosslinkers can be selected so as to modify biodegradability properties.

According to another aspect, the present invention provides a therapeutic agent delivery device for attachment to one or more wet tissue surfaces and for releasing one or more therapeutic agents to a target site comprising: (i) a dry adhesive material layer having a top surface and a bottom surface, and (ii) one or more therapeutic agent loaded patch disposed on one or more of the top surface and bottom surface of the dry adhesive material. The dry adhesive material layer comprising one or more hydrophilic polymers, one or more amine coupling groups, and one or more cross linkers, wherein the dry adhesive material is in the form of a film or tape having a top surface and a bottom surface. Further, the dry adhesive material has a liquid content such that placement of one or more of the top and/or bottom surfaces of the dry adhesive material in contact with the one or more wet surfaces causes the dry adhesive material to absorb liquid from the one or more wet surfaces, swell to form temporary crosslinking between the dry adhesive material and the wet surface, and form covalent crosslinking between the one or more amine coupling groups and the one or more wet surfaces.

According to another aspect, the present invention provides a device for providing electrical measurements of heart movements comprising: (i) a dry adhesive material layer having a top surface and a bottom surface, and (ii) one or more strain sensors disposed on one or more of the top surface and bottom surface of the dry adhesive material. The dry adhesive material layer comprising one or more hydrophilic polymers, one or more amine coupling groups, and one or more cross linkers, wherein the dry adhesive material is in the form of a film or tape having a top surface and a bottom surface. The dry adhesive material has a liquid content such that placement of one or more of the top and/or bottom surfaces of the dry adhesive material in contact with the one or more wet surfaces causes the dry adhesive material to absorb liquid from the one or more wet surfaces, swell to form temporary crosslinking between the dry adhesive material and the wet surface, and form covalent crosslinking between the one or more amine coupling groups and the one or more wet surfaces.

According to another aspect, the present invention provides a method of adhering wet tissues together comprising: providing a dry adhesive material comprising: (i) one or more hydrophilic polymers; (ii) one or more amine coupling groups, and (iii) one or more cross linkers; placing the dry adhesive material in contact with one or more wet tissue surfaces; allowing the dry adhesive material to absorb liquid from the one or more wet surfaces to thereby swell the adhesive material; allowing instant crosslinking by intermolecular interactions between the adhesive material and the one or more wet surfaces; and allowing quick covalent crosslinking between the adhesive material and the one or more wet surfaces.

According to another aspect, the present invention provides a method for delivering therapeutic agent to a target site comprising: providing a therapeutic agent delivery device comprising a (i) dry adhesive material comprising: one or more hydrophilic polymers; one or more amine coupling groups, and one or more cross linkers; and (ii) one or more therapeutic agent loaded patch disposed on one or more of the top surface and bottom surface of the dry adhesive material; placing one or more of the top surface and bottom surface of the dry adhesive material in contact with one or more wet tissue surfaces; allowing the dry adhesive material to absorb liquid from the one or more wet surfaces to thereby swell the adhesive material; allowing instant crosslinking by intermolecular interactions between the adhesive material and the one or more wet surfaces; allowing quick covalent crosslinking between the adhesive material and the one or more wet surfaces; and allowing the one or more therapeutic agent loaded patch to release therapeutic agent to the target site.

According to another aspect, the present invention provides a method for providing electrical measurements of heart movements comprising: providing an electrical measurement device comprising: (i) a dry adhesive material layer having a top surface and a bottom surface, the dry adhesive material layer comprising: one or more hydrophilic polymers; one or more amine coupling groups, and one or more cross linkers; and (ii) one or more strain sensors disposed on one or more of the top surface and bottom surface of the dry adhesive material; placing one or more of the top surface and bottom surface of the dry adhesive material in contact with one or more wet tissue surfaces; allowing the dry adhesive material to absorb liquid from the one or more wet surfaces to thereby swell the adhesive material; allowing instant crosslinking by intermolecular interactions between the adhesive material and the one or more wet surfaces; allowing quick covalent crosslinking between the adhesive material and the one or more wet surfaces; and allowing the one or more strain sensors to electrically measure heart movements.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIGS. 3A-E schematically illustrate various features of the DST according to an embodiment of the present invention, wherein FIG. 3A depicts various shapes of the DST owing to its high flexibility in fabrication, FIG. 3B illustrates a DST as colorized with a red food dye for visualization in a swollen state (through water absorption) and stretched 9 times and 16 times of the original unstretched length, FIG. 3C shows a nominal stress vs. stretch curve for the DST in FIG. 3B as stretched to over 16 times of the original unstretched length, FIG. 3D is a photograph of In vitro biocompatibility of the DST based on Live/Dead assay of mouse embryonic fibroblasts (mEFs) after 24-hour culture (left) and a graph thereof (right), and FIG. 3E graphically illustrates In vitro biodegradation of the gelatin-based DST in DPBS with collagenase.

FIGS. 4A-B are photographs of a DST according to an embodiment of the present invention, wherein FIG. 4A illustrates the DST as initially prepared in dry state with thin tape form (~100 μm dry thickness), and FIG. 4B illustrates use of the DST together with backing material.

FIGS. 6A-D graphically show the properties and adhesion performance of a chitosan-based DST according to an embodiment of the present invention, wherein FIG. 6A shows a nominal stress vs. stretch curve for a swollen chitosan-based DST, FIG. 6B shows a force vs. displacement curve between clamps for an unnotched and a notched chitosan-based DST for fracture toughness measurement, FIG. 6C shows interfacial toughness, and shear and tensile strength between wet pig skins adhered by the chitosan-based DST, and FIG. 6D shows In vitro biodegradation of the chitosan-based DST in Dulbecco's PBS (DPBS) with collagenase, lysozyme, and NAGase.

FIGS. 8A-C schematically illustrate mechanical testing setups for evaluation of adhesion performance of the DST according to an embodiment of the present invention, wherein FIG. 8A shows a testing setup for interfacial toughness measurements based on the standard 180-degree peeling test (ASTM F2256), FIG. 8B shows a testing setup for shear strength measurements based on the standard lap-shear test (ASTM F2255), and FIG. 8C shows a testing setup for tensile strength measurements based on the standard tensile test (ASTM F2258).

FIGS. 9A-E graphically illustrate adhesion performance of a DST according to an embodiment of the present invention, wherein FIG. 9A shows interfacial toughness and shear and tensile strength vs. pressing time for adhered wet pig skins by the DST with NHS ester, FIG. 9B shows interfacial toughness and shear and tensile strength vs. time after pressing for adhered wet pig skins by the DST with NHS ester, FIG. 9C shows interfacial toughness and shear and tensile strength vs. pressing time for adhered wet pig skins by the DST without NHS ester, FIG. 9D shows interfacial toughness and shear and tensile strength vs. time after pressing for adhered wet pig skins by the DST without NHS ester, and FIG. 9E shows a comparison of adhesion performances between the DST and commercially available tissue adhesives. Values in FIGS. 9A-E represent the mean and the standard deviation (n=3-5).

FIGS. 10A-B illustrate a DST between adhered tissues according to an embodiment of the present invention, wherein FIG. 10A shows dark-field and bright-field overlaid with green fluorescence microscope images of pig skins adhered by the DST right after application, and FIG. 10B shows dark-field and bright-field overlaid with green fluorescence microscope images of pig skins adhered by the DST 24 h after application.

FIGS. 13I-N show photographs of pig skin and various engineering solids adhered by the DST.

FIGS. 14A-C graphically illustrate representative curves for mechanical tests of various tissues adhered by the DST according to an embodiment of the present invention, wherein FIG. 14A show a force/width vs. displacement curves for 180-degree peeling tests of various tissues adhered by the DST, FIG. 14B shows shear stress vs. displacement curves for lap-shear tests of various tissues adhered by the DST, and FIG. 14C shows tensile stress vs. displacement curves for tensile tests of various tissues adhered by the DST.

FIGS. 15A-C schematically depict surface functionalization of engineering solids, wherein FIG. 15A is a schematic illustration for primary amine functionalization of silicon, titanium, and PDMS, and subsequent covalent coupling between the primary amine groups and the NHS ester groups in the DST according to an embodiment of the present invention, FIG. 15B is a schematic illustration for primary amine functionalization of polycarbonate, and subsequent covalent coupling between the primary amine groups and the NHS ester groups in the DST according to an embodiment of the present invention, and FIG. 15C shows a schematic illustration for primary amine functionalization of polyimide, and subsequent covalent coupling between the primary amine groups and the NHS ester groups in the DST according to an embodiment of the present invention.

FIGS. 17A-D schematically illustrate surgical-sealing applications enabled by the DST according to embodiments of the present invention, wherein FIG. 17A illustrates sealing an air-leaking lacerated porcine trachea, FIG. 17B illustrates sealing of an air-leaking lacerated porcine lung lobe, FIG. 17C illustrates sealing of a fluid-leaking porcine stomach, and FIG. 17D illustrates sealing of damaged porcine small intestine by forming anastomosis with DST.

FIGS. 18A-D schematically illustrate integration of various devices onto wet tissues enabled by the DST according to embodiments of the present invention, wherein FIG. 18A illustrates adhesion of a drug-loaded patch on a beating porcine heart with a cut, FIG. 18B graphically shows diffusion of a mock-drug (fluorescein) from the DST-adhered drug patch of FIG. 18A into the heart tissue over time, FIG. 18C illustrates adhesion of a DST-strain sensor hybrid on a beating porcine heart, FIG. 18D illustrates normalized electrical resistance of the DST-adhered strain sensor of FIG. 18C over time to measure the deformation of the beating heart.

DETAILED DESCRIPTION

Figure 1A:
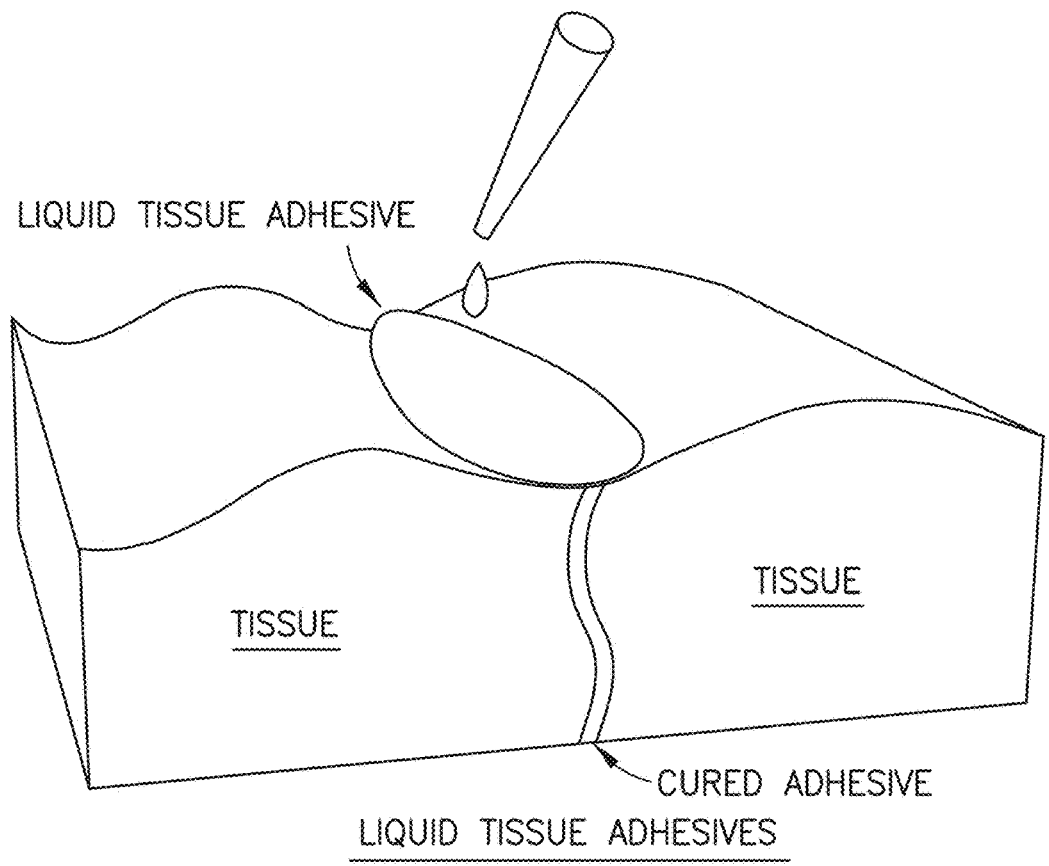
FIGS. 1A-C schematically illustrate tissue adhesives according to the prior art, with FIG. 1A depicting an existing tissue adhesive in the form of liquid, FIG. 1B depicting an existing tissue adhesives in the form of a wet hydrogel, and FIG. 1C depicting a schematic for the mechanism of existing tissue adhesives which relies on diffusion of monomers or polymers into the polymer network of tissues for bonding.

The following definitions are useful for interpreting terms applied to features of the embodiments disclosed herein, and are meant only to define elements within the disclosure.

As used herein, the term "dry" when describing the double sided material of the present invention refers to a material that is below the equilibrium moisture content of the material in use. As such, when a dry double sided material of the present invention is placed in contact with a wet tissue or other wet or wetted (e.g., wetted by saline) surface to which it will adhere, the material will absorb water, saline, moisture, and physiological body fluids such as blood plasma, interstitial fluid, lymphatic fluid, cerebrospinal fluid, and gastrointestinal fluid from the wet or wetted surface. Generally, a dry adhesive material will have less than about 50% by weight of liquid components based on total weight of the dry adhesive material.

As used herein, the term "absorb" when describing the mechanism by which the dry double sided material absorbs water, saline, moisture, and physiological body fluids such as blood plasma, interstitial fluid, lymphatic fluid, cerebrospinal fluid, and gastrointestinal fluid from a wet surface in which it is placed in contact with, refers to atoms or molecules from the liquid of the wet surface crossing the surface of and entering the dry double sided material.

As used herein, the term "tape" or "film" when describing the double sided material of the present invention refers to a structure that has a relatively large area as compared to thickness. Such a structure provides flexibility.

As used herein, the term "double sided" when describing the adhesive material of the present invention refers to the adhesive tape or film that provides adhesive properties on both top and bottom sides of the adhesive. It is noted that while the adhesive material may be referred to as double sided, the adhesive properties of a single side or of both sides of the adhesive material may be utilized in a given application. For example, during use, it may be desirable to utilize the adhesive properties of only one side of the adhesive material, while the adhesive properties of a second side, for example, may not be utilized by maintaining a material layer or backing material disposed upon the second side surface during use so as to block the adhesive properties on that second side. In such an example, the material layer or backing material may initially be disposed upon both the first and second sides, with the material layer or backing material being removed from only the first side prior to application to enable use of the adhesive properties of the first side only.

As used herein, the term "wet tissue" refers to the biological tissues that contains or be covered with aqueous media including water, saline, moisture, and physiological body fluids such as blood plasma, interstitial fluid, lymphatic fluid, cerebrospinal fluid, and gastrointestinal fluid.

As used herein, the term "instant" when used to describe the instant temporary crosslinks between the double sided material and one or more wet surfaces refers to a time elapse from the instant that the double sided material makes contact with the one or more wet surfaces of greater than zero seconds and up to or within about one minute, more preferably less than or equal to about 50 seconds, more preferably less than or equal to about 40 seconds, more preferably less than or equal to about 30 seconds, more preferably less than or equal to about 20 seconds, more preferably less than or equal to about 15 seconds, more preferably less than or equal to about 10 seconds, more preferably less than or equal to about 9 seconds, more preferably less than or equal to about 8 seconds, more preferably less than or equal to about 7 seconds, more preferably less than or equal to about 6 seconds, and more preferably less than or equal to about 5 seconds.

As used herein, the term "temporary" when used to describe the instant temporary crosslinks between the double sided material and one or more wet surfaces refers to a time range extending between time at which the instant temporary crosslinks form and the sufficiently long time such as over 24 hours after which the instant temporary crosslinks form.

As used herein, "fast" or "quick" when used to describe the fast covalent cross linking between the double sided material and one or more wet surfaces refers to a time elapse from the instant that the double sided material makes contact with the one or more wet surfaces of greater than zero seconds and up to and including 5 minutes, more preferably less than or equal to about 4.5 minutes, more preferably less than or equal to about 4 minutes, more preferably less than or equal to about 3.5 minutes, more preferably less than or equal to about 3 minutes, more preferably less than or equal to about 2.5 minutes, more preferably less than or equal to about 2 minutes, more preferably less than or equal to about 1.5 minutes, and more preferably less than or equal to about 1 minute.

As used herein, "swelling" when used to describe the dry adhesive material absorption and swelling upon contact with one or more wet surfaces generally refers to an increase in size by the dry adhesive material. The dry adhesive material is generally in the form of a tape or film, which becomes thicker upon uptake of liquid.

As used herein, "biodegradable" when used to describe the dry adhesive material refers the decomposition and/or subsequent removal of the implanted material in part or whole within the living animals by the endogenous enzymes and/or water inside the animals.

As used herein, "engineering solids" refers to solid materials that are not biological tissues including synthetic materials such as plastics, metals, glass, ceramics, and elastomers as well as biomaterials processed from natural sources.

Figure 2A:
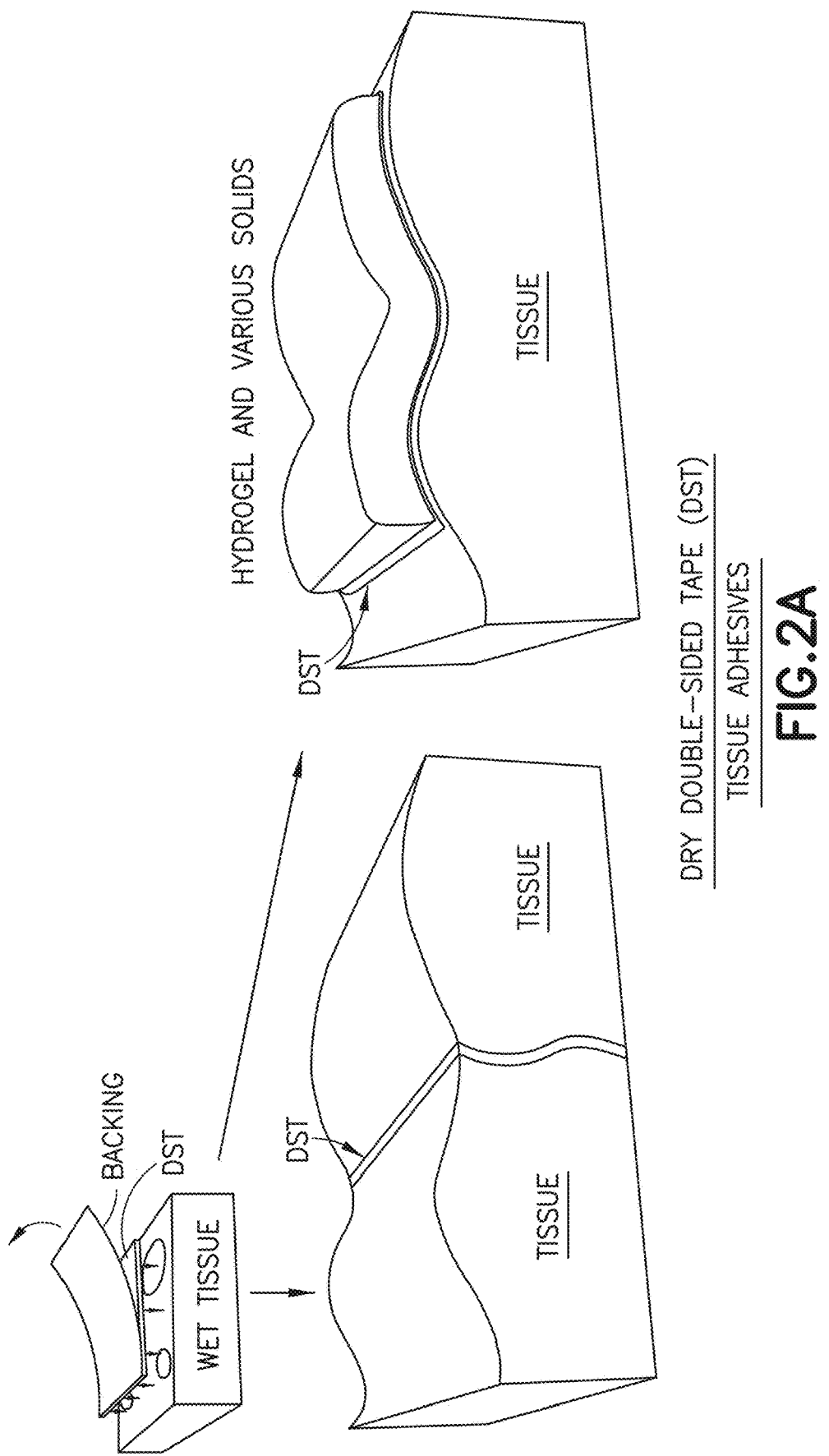
FIGS. 2A-B schematically illustrate a dry double sided material in the form of a tape according to an embodiment of the present invention, with FIG. 2A depicting placement of the dry double sided tape (hereinafter sometimes referred to as "DST") between two wet tissues according to an embodiment of the present invention (left) and attachment of a hydrogel and/or various other materials to a wet tissue surface using the DST according to an embodiment of the present invention (right), and FIG. 2B depicting a dry-crosslinking mechanism for the DST according to an embodiment of the present invention which integrates drying of interfacial liquid (e.g., water) by swelling of the DST, instant temporary crosslinking, and fast covalent crosslinking.

The present invention generally provides an adhesive material that is capable of adhering to wet surfaces and adhering wet surfaces together, particularly wet tissue surfaces. The adhesive material is a dry adhesive material fabricated so as to provide a new dry-crosslinking mechanism for instant strong adhesion of wet surfaces. In particular, the dry adhesive material is fabricated such that, when placed into contact with one or more wet surface, it absorbs liquid from the one or more wet surfaces, which swells the adhesive material. This absorption of interfacial liquid allows instant crosslinking by intermolecular interactions between the adhesive material and the one or more wet surfaces, followed by quick covalent crosslinking between the adhesive material and the one or more wet surfaces (see FIGS. 2A-B).

Figure 1B:
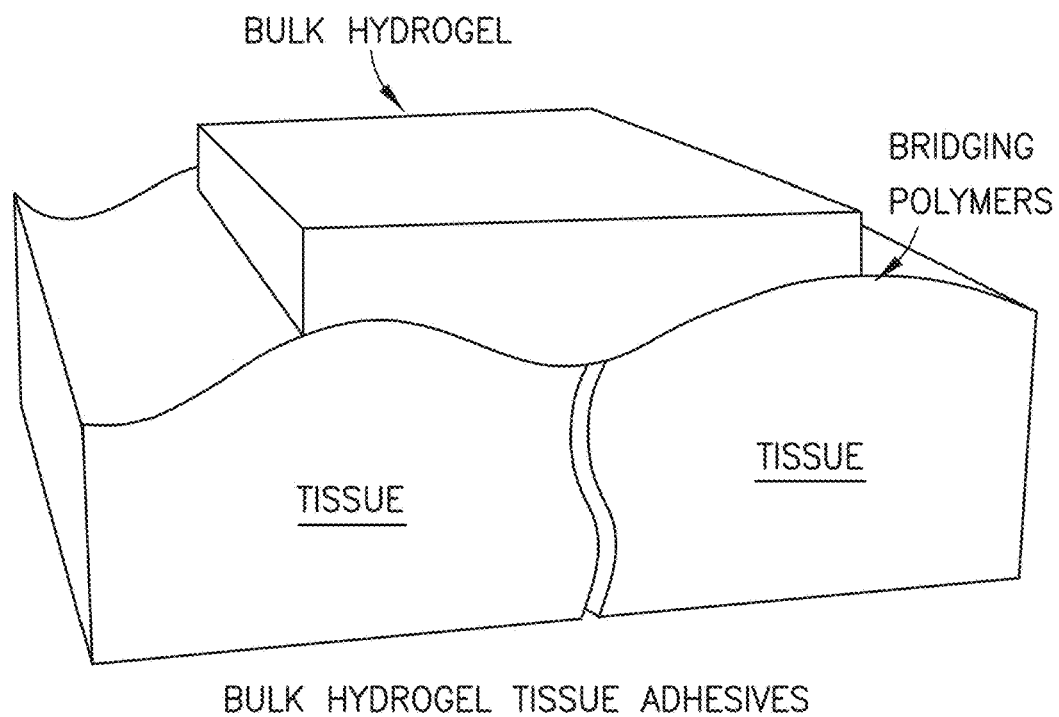
Figure 1C:
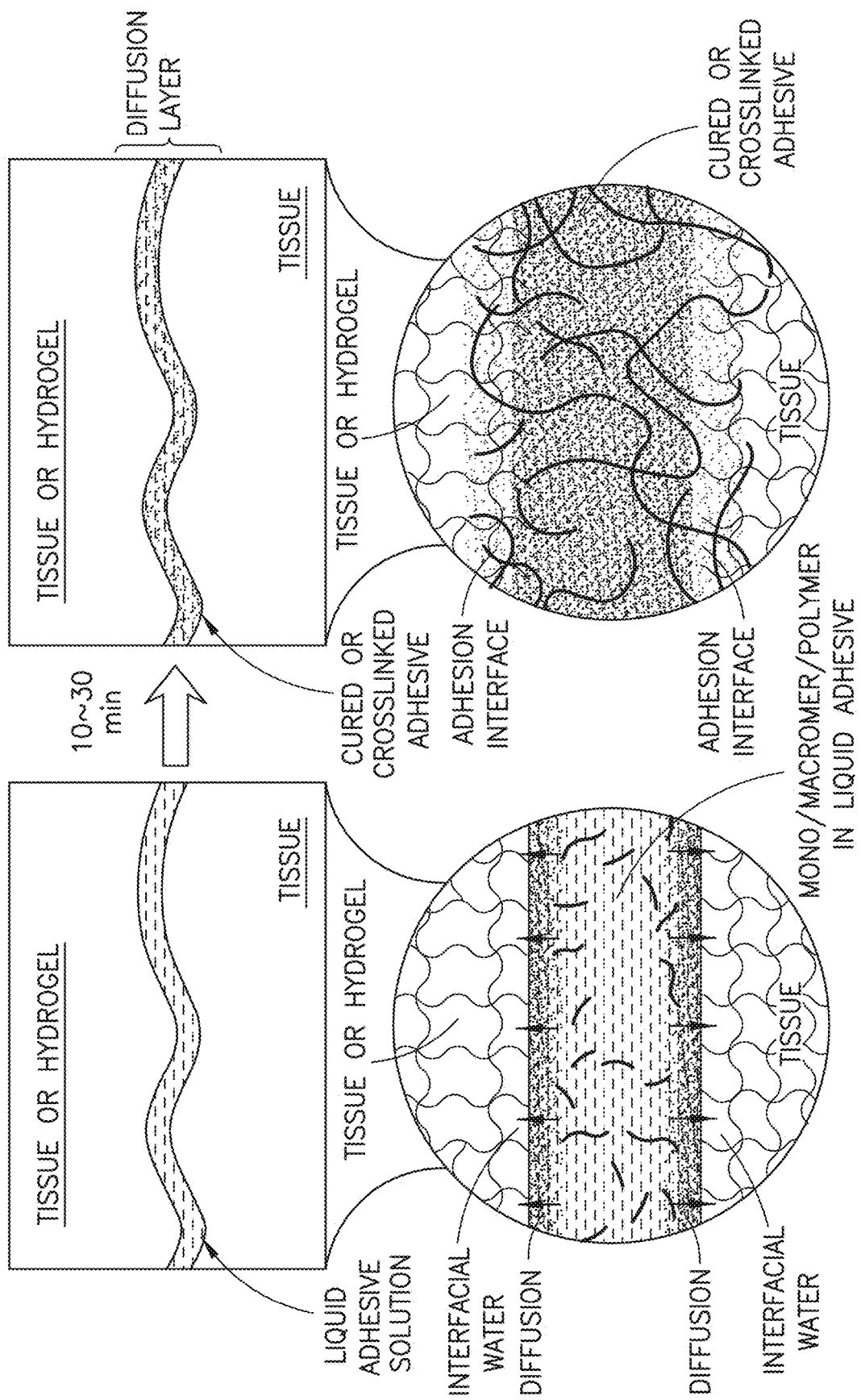

The present invention dry adhesive material thereby overcomes the above-mentioned limitations of the existing adhesive materials (as further depicted in FIGS. 1A-C). Rather than diffusing molecules towards tissues as required by the existing adhesive materials, the present dry adhesive material achieves instant strong adhesion to wet surfaces by synergistically combining drying of interfacial liquid by swelling of the dry adhesive material, instant temporary crosslinking, and fast covalent crosslinking between the adhesive material and the one or more wet surfaces.

As described further below, ex vivo and in vitro models demonstrated that the present dry adhesive material is capable of achieving strong adhesion between diverse wet dynamic tissues (e.g., skin, tendon, stomach, muscle, heart, and liver) and engineering solids (e.g., hydrogel, silicon, titanium, polydimethylsiloxane, polyimide, and polycarbonate) within five seconds, with interfacial toughness on the order of about 1,150 J m$^{-2}$ and shear and tensile strengths on the order of about 160 kPa, while providing low shear moduli (~10 kPa) and high stretchability (greater than 10 times) similar to those properties found in biological tissues, high biocompatibility and controllable biodegradation. As such, the present dry adhesive material provides not only a new paradigm in wet adhesion, but also enables new opportunities in applications as diverse as tissue adhesives, bioscaffolds, drug delivery, and wearable and implantable devices.

Reference will now be made in detail to embodiments of the present invention, examples of which are illustrated in the accompanying drawings. Wherever possible, the same reference numbers are used in the drawings and the description to refer to the same or like parts.

According to one aspect, the present invention provides an adhesive material comprising combination of: (i) one or more hydrophilic polymers, (ii) one or more amine coupling groups, and (iii) one or more cross linkers. The adhesive material is in the form of a dry material in that, when it is placed into contact with one or more wet surfaces such as wet tissue, it absorbs liquid from the one or more wet surfaces, removing the interfacial liquid present between the adhesive material and the wet surfaces. This liquid absorption causes the dry material to swell. Absorption of liquid and swelling of the dry adhesive material provides instant temporary crosslinking between the adhesive material (particularly between carboxylic acid groups, hydroxyl groups, sulfonic acid groups, amine groups, and catechol groups in the adhesive material) and the wet surface, and further allows for fast subsequent covalent coupling or crosslinking between the one or more amine coupling groups (e.g., NHS ester groups, sulfo-NHS ester groups, aldehyde groups, imidoester groups, epoxide groups) and the one or more wet surfaces via amine groups naturally present in the one or more wet surfaces.

According to embodiments of the present invention, the (i) one or more hydrophilic polymers are selected from any conventional hydrophilic polymers that absorb water at a dry state, including, but not limited to polyacrylic acid, polyacrylamide, polyvinyl alcohol, polyhydroxy ethyl methacrylate, polyethylene glycol, poly vinyl pyrrolidone, poly styrene sulfonate, casein, albumin, gelatin, collagen, chitosan, hyaluronic acid, alginic acid, oxidized alginate, pectin, and combinations thereof. Because the present adhesive material can be used in a wide variety of biomedical applications, the polymers used in the present invention are preferably biocompatible (although for non-biomedical applications it would not be necessary to utilize only biocompatible polymer materials). According to preferred embodiments, the one or more hydrophilic polymers contain one or more negatively-charged groups such as poly (acrylic acid), casein, albumin, and alginic acid, whose negatively-charged groups endow hygroscopic properties that are desirable for rapid absorption and removal of interfacial liquid on wet surfaces.

According to embodiments of the present invention, the (ii) one or more amine coupling groups are selected from conventional amine coupling groups, including but not limited to, N-hydroxysuccinimide ester, N-hydroxysulfosuccinimide ester, aldehyde, imidoester, epoxide, isocyanate, catechol, and combinations thereof. Because the present adhesive material can be used in a wide variety of biomedical applications, the amine coupling groups used in the present invention are preferably biocompatible (although for non-biomedical applications it would not be necessary to utilize only biocompatible amine coupling groups). Such amine coupling groups are configured such that the one or more hydrophilic polymers can be grafted with the one or more amine-coupling groups, and such that the one or more amine coupling groups subsequently form covalent crosslinks with the wet surface on which the adhesive material is used.

According to embodiments of the present invention, the (iii) one or more crosslinkers are selected from conventional crosslinkers, including but not limited to gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. Because the present adhesive material can be used in a wide variety of biomedical applications, the crosslinkers used in the present invention are preferably biocompatible (although for non-biomedical applications it would not be necessary to utilize only biocompatible crosslinkers).

According to a preferred embodiment, the adhesive material is a gelatin-based adhesive material. A gelatin-based adhesive material according to an embodiment of the present invention preferably includes: about 20 w/w % to about 40 w/w %, more preferably about 25 w/w % to about 35 w/w %, and even more preferably about 30 w/w % polyacrylic acid; about 5 w/w % to about 15 w/w %, more preferably about 10 w/w % gelatin; about 0.5 w/w % to about 1.5 w/w % PAAc-NHS ester, more preferably about 1 w/w % PAAc-NHS ester; about 0.05 w/w % to about 0.15 w/w % gelatin methacrylate, more preferably about 0.1 w/w % gelatin methacrylate; and deionized water for the remaining parts, in its as-prepared (before drying) form.

According to an exemplary embodiment, a gelatin-based DST comprises about 30 w/w % polyacrylic acid, about 10 w/w % gelatin, about 1 w/w % PAAc-NHS ester, about 0.1 w/w % gelatin methacrylate, and deionized water for the remaining parts in its as-prepared (before drying) form.

According to a preferred embodiment, the adhesive material is a chitosan-based adhesive material. A chitosan-based adhesive material according to an embodiment of the present invention preferably includes: about 20 w/w % to about 40 w/w %, more preferably about 25 w/w % to about 35 w/w %, and even more preferably about 30 w/w % polyacrylic acid; about 1 w/w % to about 3 w/w %, more preferably about 2 w/w % chitosan; about 0.5 w/w % to about 1.5 w/w % PAAc-NHS ester, more preferably about 1 w/w % PAAc-NHS ester; about 0.05 w/w % to about 0.15 w/w % gelatin methacrylate, more preferably about 0.1 w/w % gelatin methacrylate; and deionized water for the remaining parts in its as-prepared (before drying) form.

According to an exemplary embodiment, a chitosan-based DST comprises about 30 w/w % poly (acrylic acid), about 2 w/w % chitosan, about 1 w/w % PAAc-NHS ester, about 0.1 w/w % gelatin methacrylate, and deionized water for the remaining parts in its as-prepared (before drying) form.

According to a preferred embodiment, an adhesive material comprises: (i) about 20 w/w % to about 55 w/w % of one or more hydrophilic polymers, (ii) about 0.5 w/w % to about 1.5 w/w % of one or more amine coupling groups, and (iii) and about 0.05 w/w % to about 0.15 w/w of one or more crosslinkers, and deionized water for the remaining parts in its as-prepared (before drying) form.

Figure 2B:
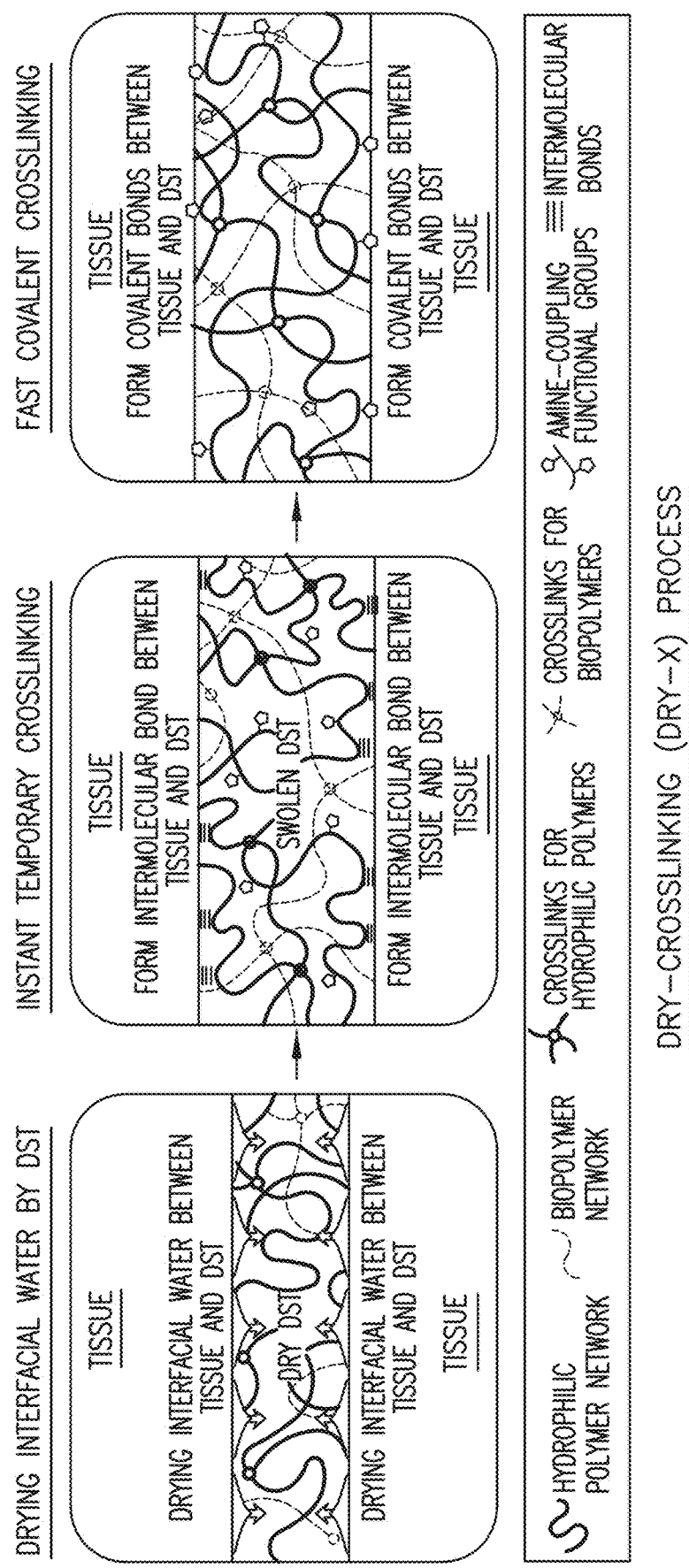
Figure 5:
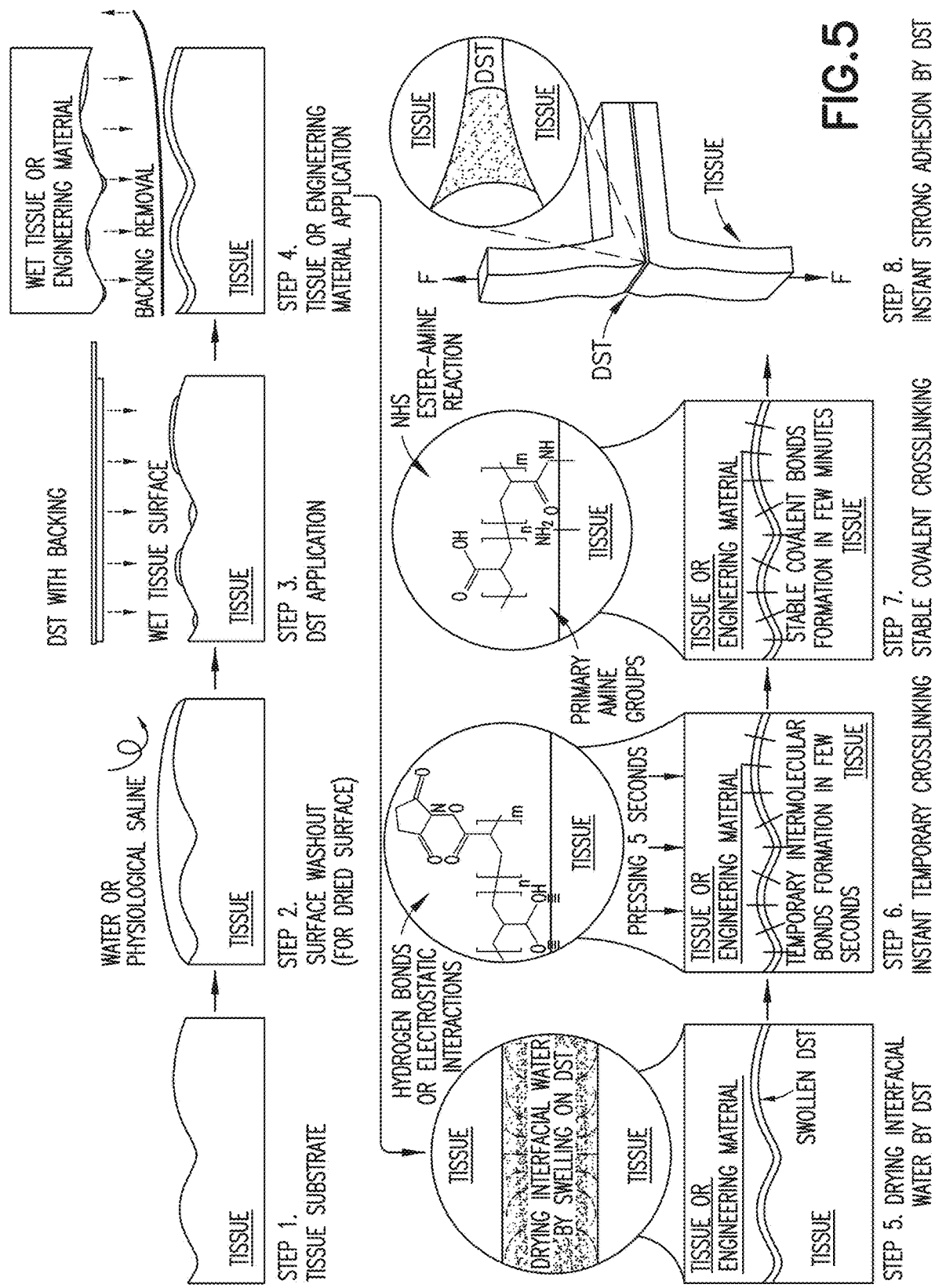
FIG. 5 schematically illustrates DST application according to an embodiment of the present invention, wherein the DST provides adhesion between two wet surfaces.

In a specific embodiment of the proposed mechanism, the dry adhesive material comprises (i) poly(acrylic acid), (ii) grafted with N-hydroxysuccinimide ester (PAAc-co-NHS ester), (iii) crosslinked by biodegradable gelatin methacrylate, and (i) one or more biodegradable biopolymers (e.g., gelatin or chitosan). This dry adhesive material is preferably in the form of a film or tape. The negatively charged carboxylic acid groups in the PAAc-co-NHS ester facilitate quick swelling of the dry adhesive material to dry the wet surfaces of various tissues quickly. Simultaneously, the carboxylic acid groups in the PAAc-NHS form instant intermolecular bonds (e.g., hydrogen bonds and electrostatic interactions) with the tissue surfaces under gentle pressing (e.g., 1 kPa pressure) for 1a short period of time (e.g., less than 5 sec) (FIGS. 2B and 5). The NHS ester groups grafted in the PAAc-co-NHS ester further form covalent coupling with primary amine groups present on various tissues within few minutes without further pressing to provide strong long-term adhesion (FIGS. 2B and 5). After adhering on the tissue surface, the swollen dry adhesive material becomes a thin layer of a hydrogel with fracture toughness over 1,000 J m$^{-2}$ (FIGS. 6 and 7), owing to the double-network structure formed between the stretchable PAAc-co-NHS ester network and the biopolymer network.

According to embodiments of the present invention, the adhesive material has a top surface and a bottom surface. Preferably, the adhesive material is generally in the form of a sheet, tape, or film (all of which may be perforated, partially perforated, or not perforated), with a top surface and a bottom surface. In preferred embodiments, the adhesive material is provided with a removable backing layer or an integrated (non-removable) material layer disposed upon one or more adhesive surfaces. For example, one or more removable backing material layers may be disposed upon one or more adhesive surfaces, particularly to aid in handling the adhesive material and to provide protection against moisture. If desired, one or more integrated material layers may be may be disposed upon one or more adhesive surfaces, particularly to provide one or more non-adhesive sides or portions of sides for single-sided usage or for partial side usage.

For example, an entire top surface of an adhesive material may have a removable backing layer disposed thereon, while the entire bottom surface may have an integrated material layer disposed thereon. As such, only the adhesive properties of the top surface of the adhesive material may be used in an application by removing the backing layer prior to use. Similarly, both the entire top and bottom surfaces may have a removable backing layers disposed thereon, such that the adhesive properties of both the top and bottom surfaces of the adhesive material may be used in an application by removing the backing layers prior to use. In some applications, it may be desirable to have a combination of one or more removable backing layers disposed on a single surface (e.g., a top surface) and one or more integrated material layers also disposed on that same single surface (e.g., top surface) so that the adhesive properties of only those portions of the surface (e.g., top surface) with the removable backing layer disposed thereon may be used by removing the backing layer from those portions, while the adhesive properties of those portions of the surface (e.g., top surface) with the integrated backing material layer disposed thereon are not utilized. For example, a central portion of a top surface of an adhesive material may have an integrated material layer disposed thereon, while portions of the top surface surrounding the central portion may have one or more removable backing layers disposed thereon. This will provide a configuration in which the top surface of the adhesive material will adhere to a wet surface along an outside portion or perimeter of the adhesive material upon removal of the removable backing layers, while a central portion of the adhesive material will not adhere due to the integrated material layer which is not removed.

The integrated material layer or removable backing layer is provided so as to prevent adhesion of the material prior to the intended time of use. As such, the removable backing layer or integrated material layer is one which blocks the adhesive properties of the material. The integrated material layer or removable backing layer is provided so as to prevent adhesion of the material to non-targeted tissues during and after application on wet tissues. As such, the integrated material layer or removable backing layer is one which is non-adhesive to wet biological tissues. The removable backing layer or integrated material layer may be disposed directly on (i.e., without anything disposed between) the one or more surfaces of the adhesive material. In some embodiments, a layer or glue or other substance used for sticking materials together is disposed in between the one or more surfaces of adhesive material and the integrated material layer or removable backing layer. The removable backing layer or integrated material layer can be fabricated of any substance which prevents adhesion of the adhesive material to a wet surface. The integrated material layer or removable backing layer can be fabricated of any substance which is non-adhesive to wet biological tissues. In particular, as described herein, the adhesive material is in the form of a dry material that absorbs liquid from a wet surface when placed into contact with the wet surface, which causes the dry material to swell. This absorption of liquid and swelling of the dry adhesive material provides instant temporary cross-linking between the adhesive material and the wet surface, and further allows for fast subsequent covalent coupling or crosslinking between the adhesive material and the wet surface. As such, the removable backing layer or integrated material layer can generally be fabricated of any material that prevents liquid from coming into contact with the surface of the adhesive material. As such, the integrated material layer or backing material layer can generally be fabricated of any material that does not form an adhesive interface with wet biological tissues. Due to the use of the adhesive materials of the invention, the removable backing layer or integrated material layer should be fabricated of a biocompatible material. According to embodiments of the invention, the removable backing layer is fabricated of polyethylene or any hydrophobic polymer-coated paper and poly(methyl methacrylate) or any hydrophobic polymer films. Such removable backing layers can be adhered directly to the one or more surfaces of the adhesive material or can be adhered with a layer of glue or other adhesive such as acrylic adhesives. According to embodiments of the invention, the integrated material layer is fabricated of silicone elastomer, thermoplastic polyurethane, hydrogel, or any other biocompatible materials without adhesiveness to wet tissues. Such integrated material layers can be adhered directly to the one or more surfaces of the adhesive material.

For the instant strong adhesion of a strain sensor, the DST-strain sensor hybrid was adhered on the beating pig heart after removing the backing. The adhered strain sensor on the beating pig heart was kept for 12 hours at room temperature, and then connected with the digital multimeter to monitor the deformation of the beating heart.

As shown in FIG. 5 the adhesive material in the form of a dry double sided tape (DST) can be applied directly on the wet tissue surfaces of interest after removing a removable material layer or backing material layer provided on one or more surfaces of the DST without any other preparation process (steps 3-4). Upon contact with the wet surfaces, the dry adhesive material quickly swells by absorbing the interfacial liquid (e.g., water) and dries the wet surfaces (step 5). Simultaneously, the carboxylic acid groups in the DST form instant intermolecular bonds with the tissue surfaces (Step 6), followed by the fast covalent coupling between the NHS ester groups (amine coupling groups) in the adhesive material and the amine groups on the tissues (step 7). After adhering on tissues, the swollen adhesive material (DST) becomes a thin layer of hydrogel which provides strong adhesion between the surfaces (step 8).

Figure 6A:
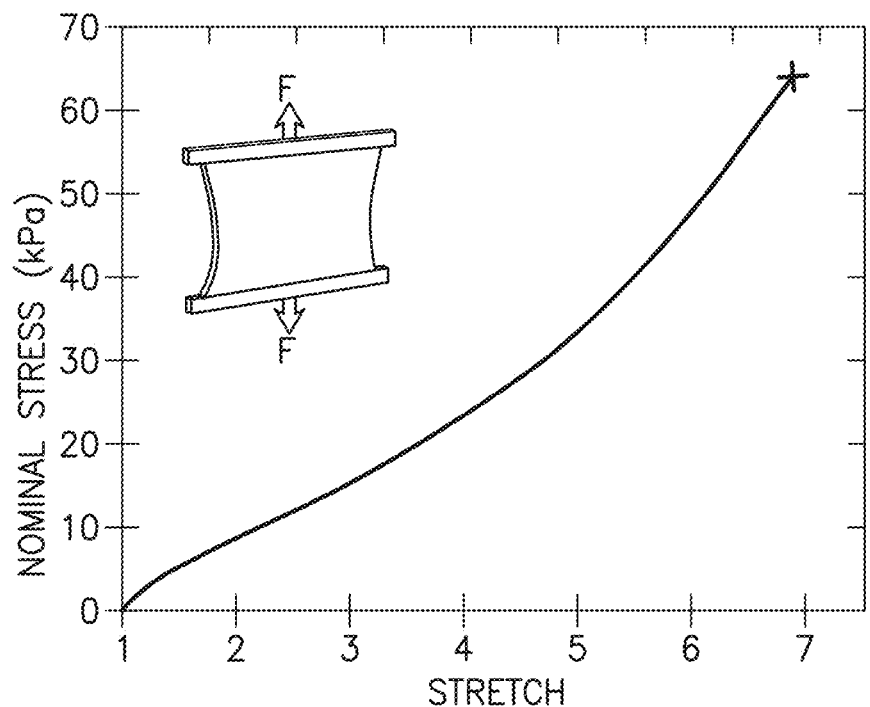
Figure 6B:
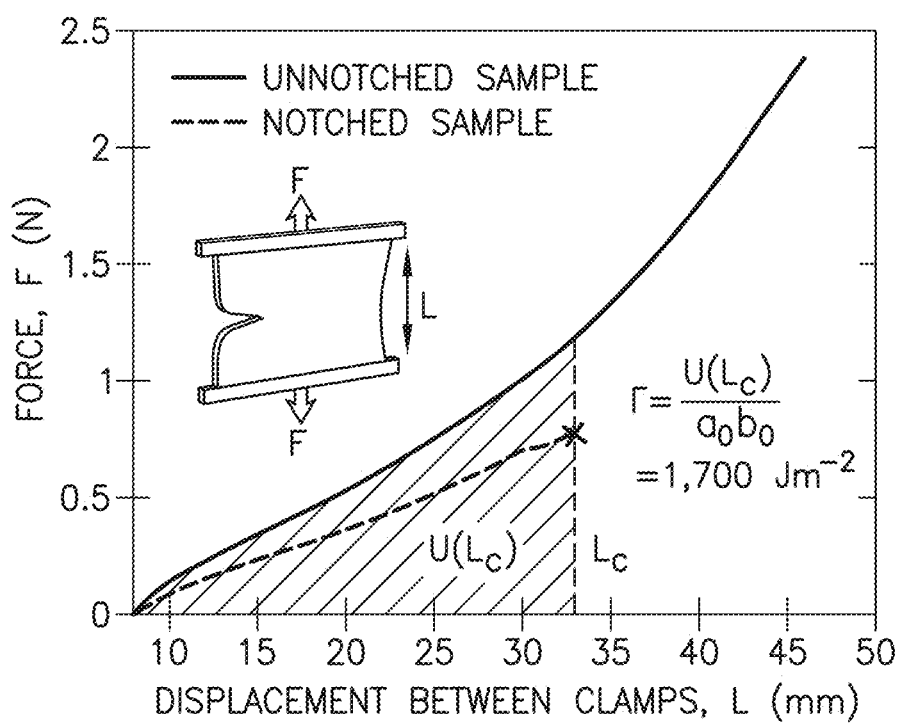
Figure 6C:
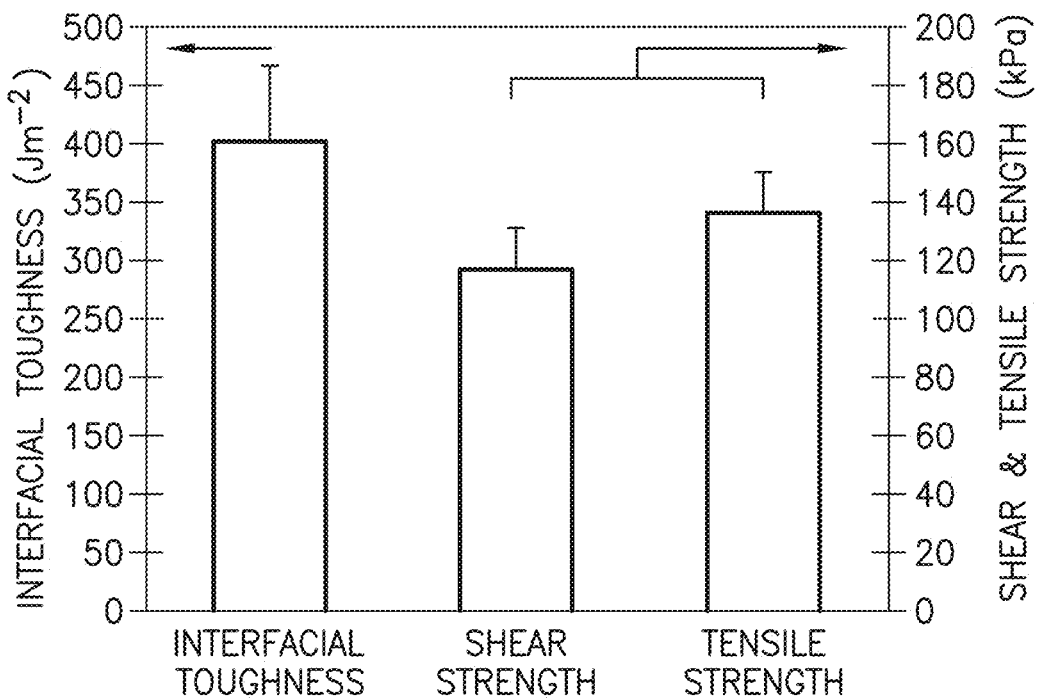
Figure 6D:
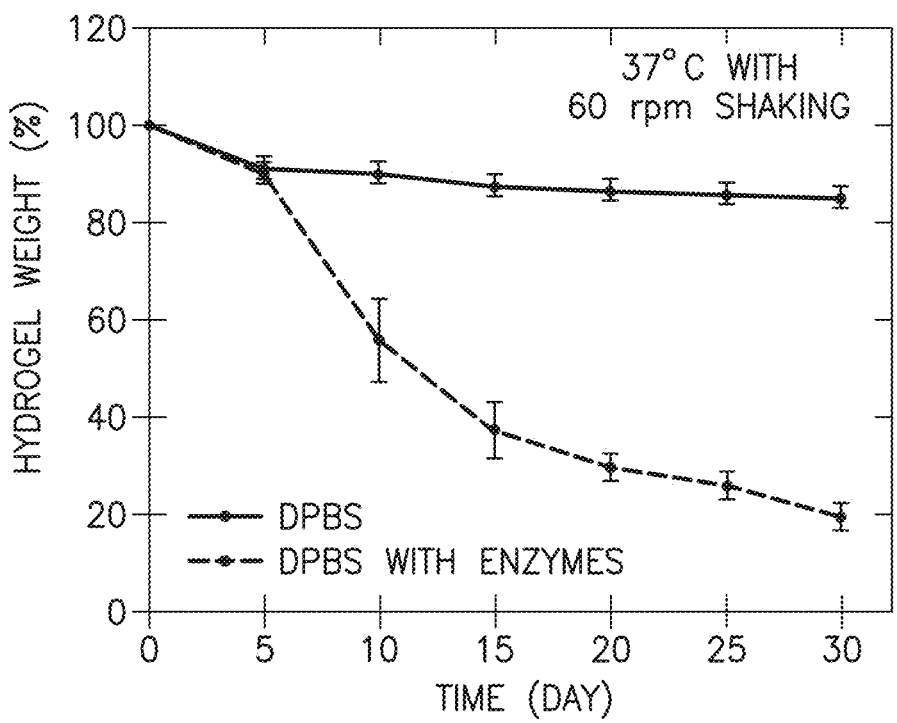

As graphically depicted in FIGS. 6A-D, this embodiment of a chitosan based dry adhesive material exhibits excellent properties and adhesion performance. As demonstrated in FIG. 6A the nominal stress vs. stretch curve for a swollen chitosan-based DST indicates that the chitosan-based DST also exhibits low shear modulus (~30 kPa) and high stretchability (>6 times) comparable to those of soft biological tissues. The chitosan-based dry adhesive material, as depicted in the FIG. 6B force vs. displacement curves between clamps for an unnotched and a notched chitosan-based DST, demonstrated excellent measured fracture toughness of 1,700 J m$^{-2}$. In addition, as depicted in FIG. 6C, excellent interfacial toughness and shear and tensile strengths between wet pig skins adhered by the chitosan-based material of the present invention were measured. FIG. 6D further demonstrates that desirable in vitro biodegradation of the chitosan-based dry adhesive material in DPBS with collagenase, lysozyme, and NAGase was achieved. Values in FIGS. 6C-D represent the mean and the standard deviation (n=3-5).

Figure 7:
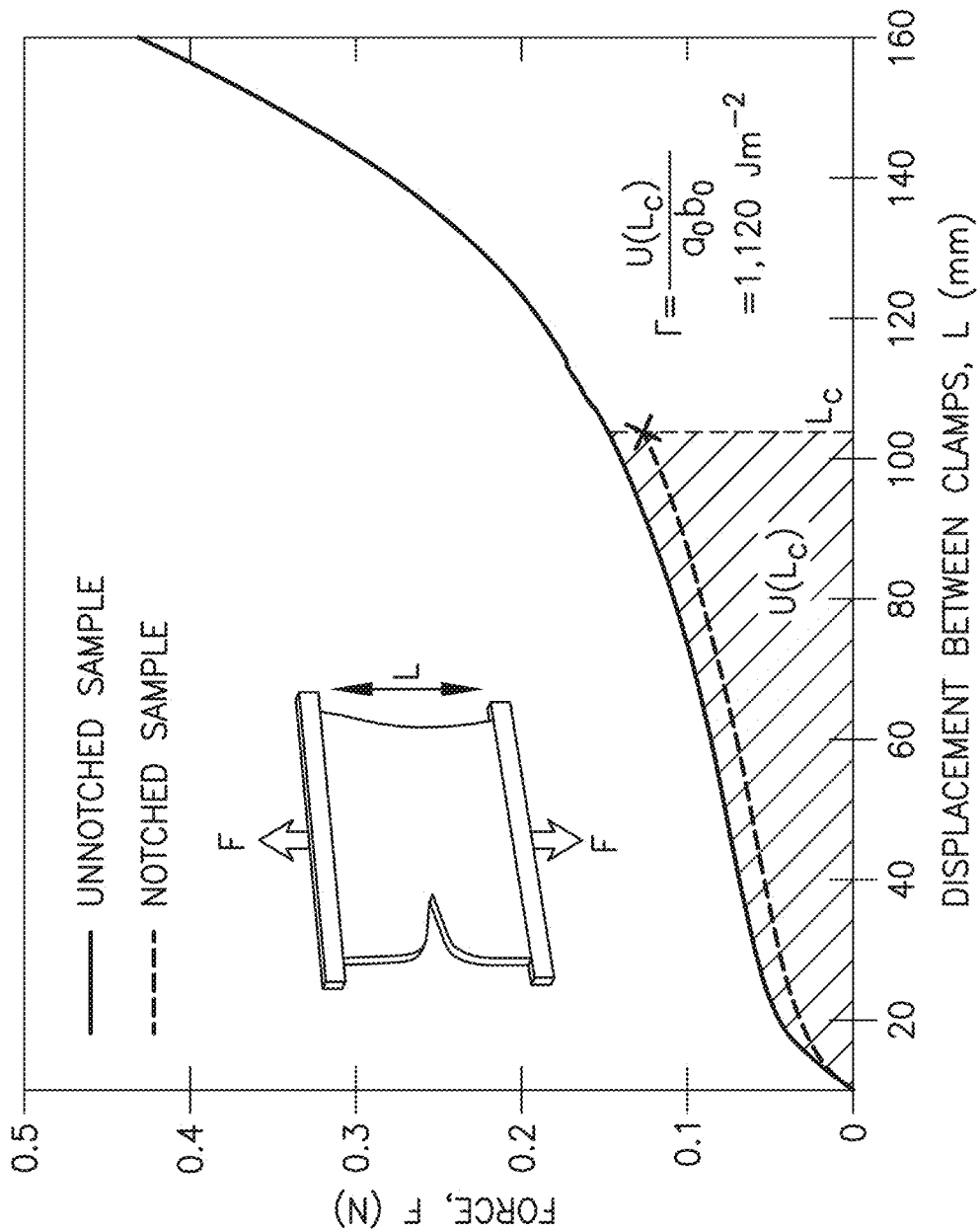
FIG. 7 graphically illustrates the fracture toughness for a gelatin-based DST according to an embodiment of the present invention.

FIG. 7 further graphically illustrates fracture toughness for this embodiment of a gelatin-based dry adhesive material. As shown, the force vs. displacement between clamps for the unnotched and notched gelatin-based adhesive material for fracture toughness measurement provided a fracture toughness of the gelatin-based adhesive material of 1,120 J m$^{-2}$. For fracture toughness measurements in FIGS. 6B and 7, F indicates the force applied to the sample, L indicates the displacement between the clamps, $L_c$ is the critical displacement between the clamps at which the notched gel fractures, $a_0$ is the width of the unnotched sample, $b_o$ is the thickness of the unnotched sample, $U(L_c)$ is the elastic energy stored in the unnotched sample at the critical displacement between the clamps $L_c$ calculated as $U(L_c)=\int_0^{L_c} F dL$, and $\Gamma$ indicates the calculated fracture toughness of the sample.

Figure 3B:
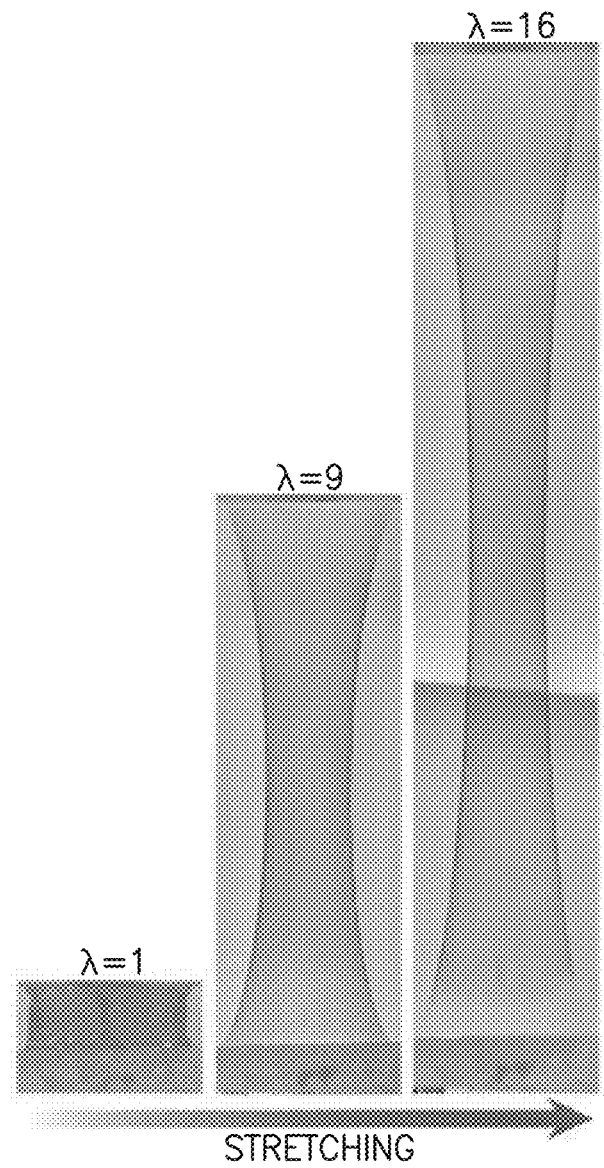
Figure 3C:
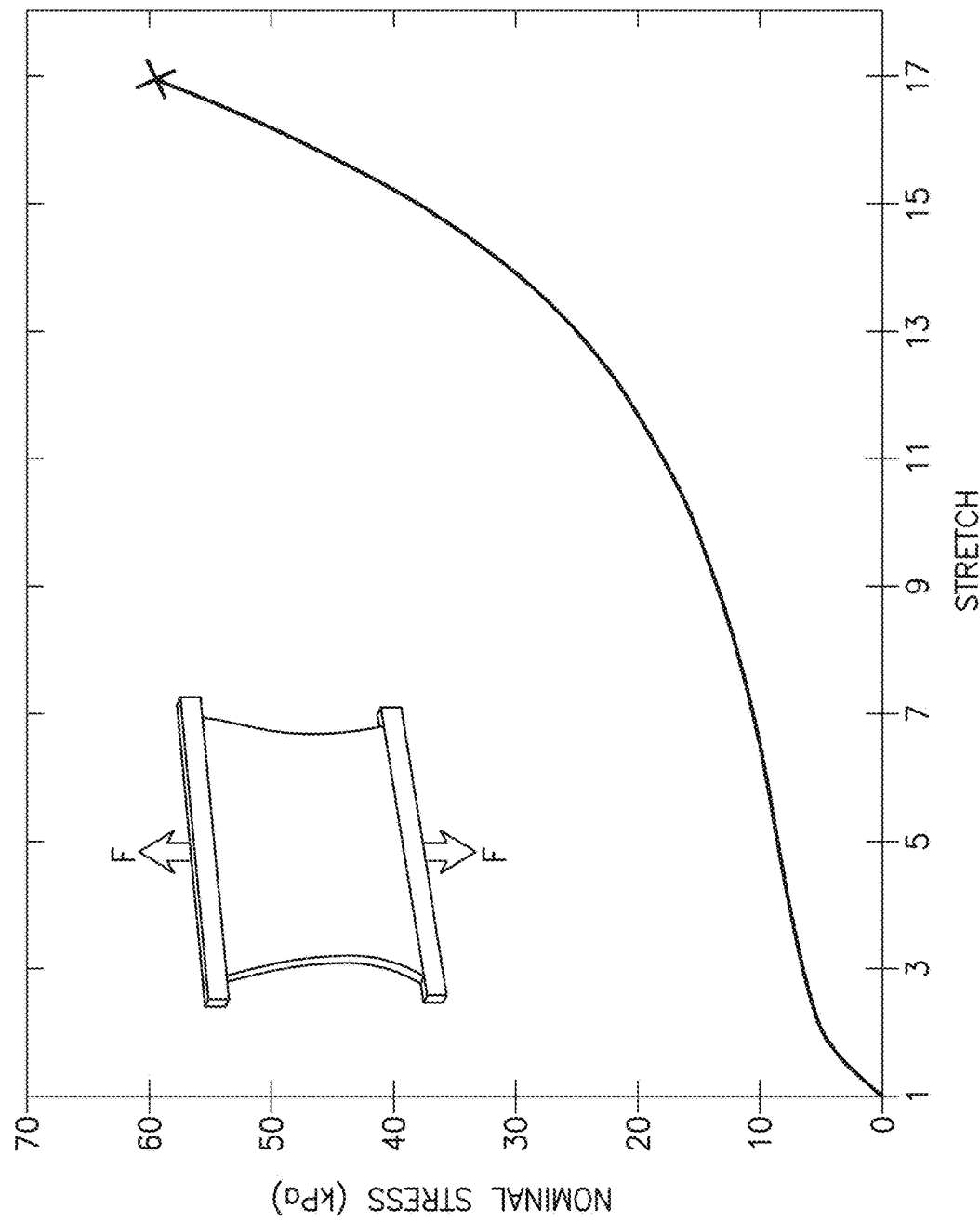
Figure 3D:
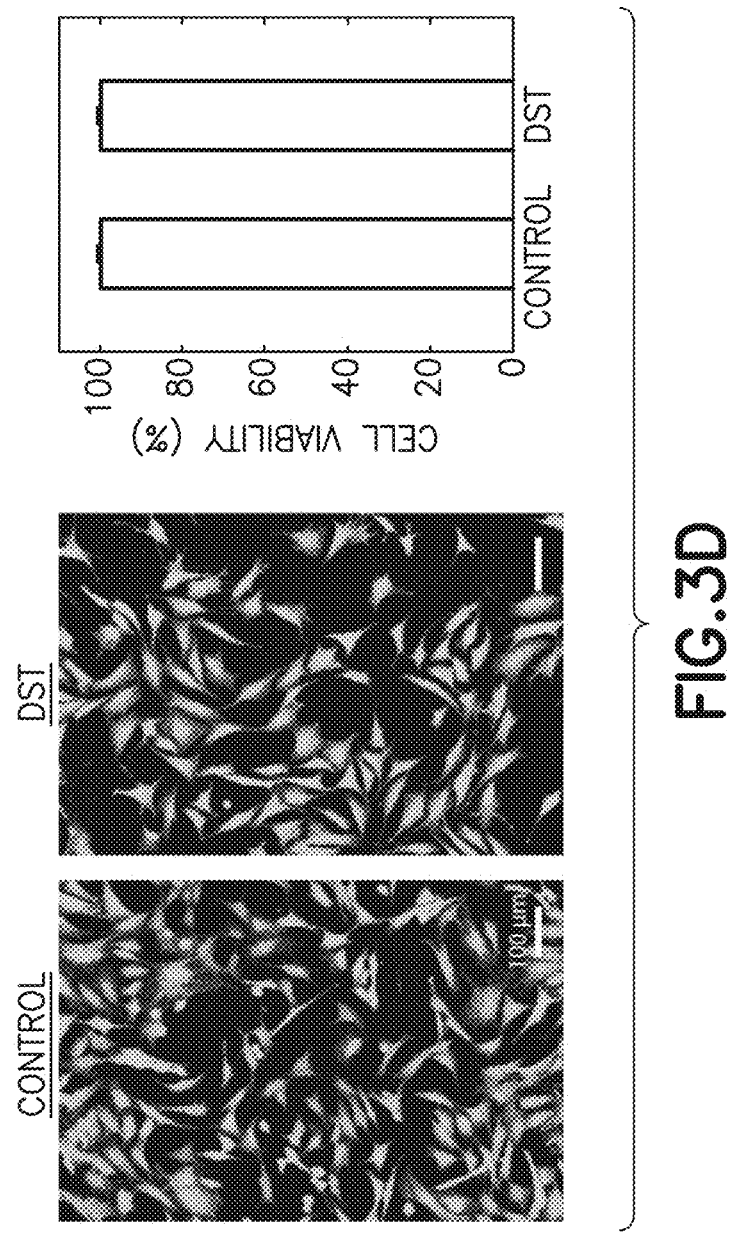
Figure 3E:
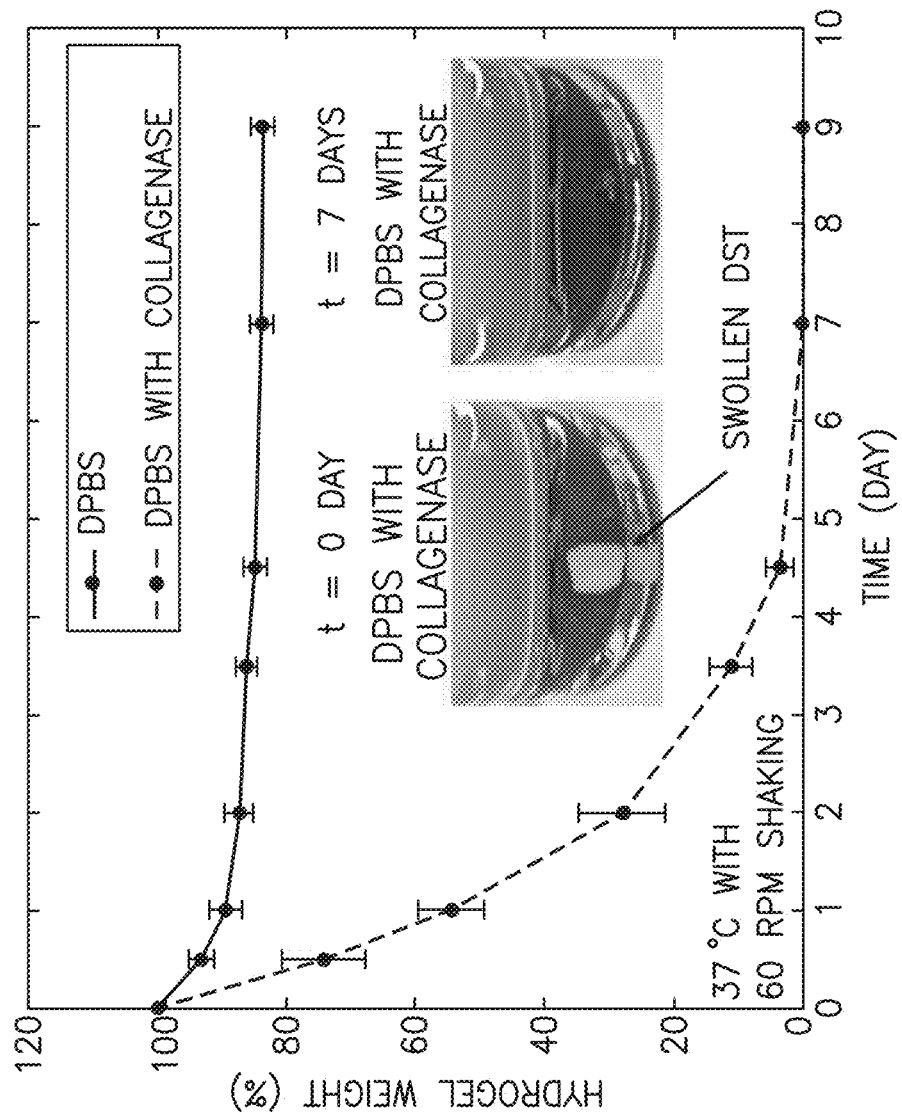
Figure 4B:
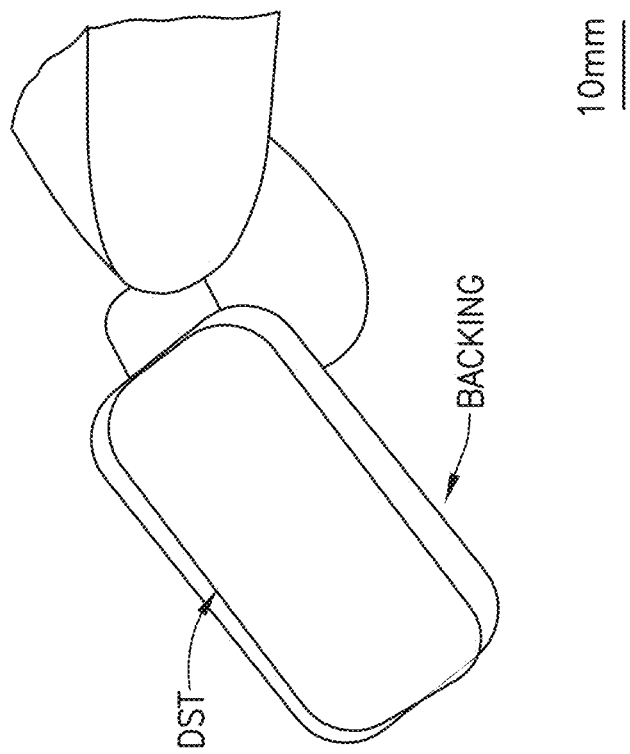
Figure 4A:
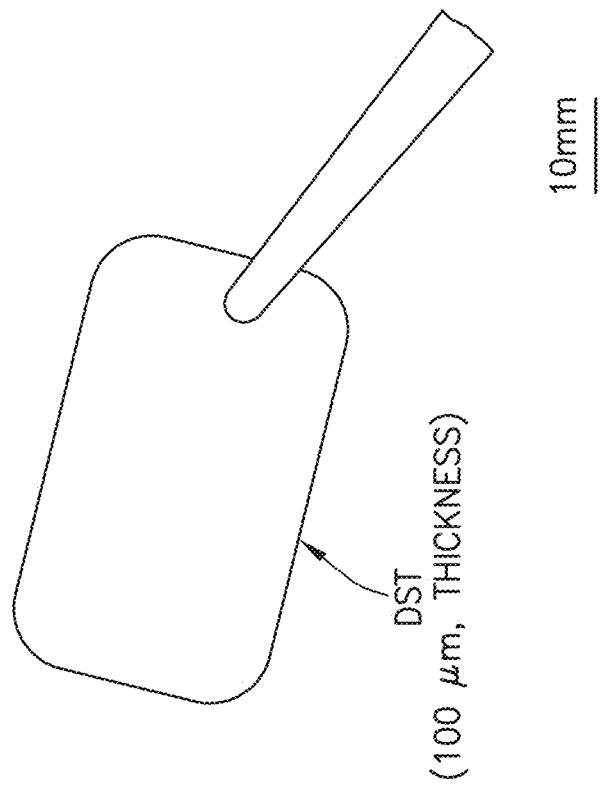

The high processability of the dry adhesive material allows its flexible fabrication into diverse shapes such as, but not limited to, flat sheets, perforated sheets, and tape-like rolls to meet various needs (see FIG. 3A). The dry adhesive material also possesses several favorable properties for biological applications. In particular, the dry adhesive material in swollen state exhibits a shear modulus of about 2.5 to about 5 kPa and stretchability over 16 times of its original unswollen length, mechanically matching those properties of soft tissues (FIGS. 3B-C). The dry adhesive material is highly biocompatible and biodegradable, owning to its composition (FIGS. 3D-E). The biocompatibility of the dry adhesive material-conditioned media is the same as the control tissue culture media (Dulbecco's Modified Eagle Medium (DMEM)), showing no observable in vitro cytotoxicity for mouse embryonic fibroblasts (mEFs) after 24-hour culture (FIG. 3D). Values in FIGS. 3 D-E represent the mean and the standard deviation (n=3-5).

Still further, the (i) one or more polymers and/or the (iii) one or more crosslinkers utilized in the present dry double sided material can be selected so as to provide a desired biodegradability properties. For example, as demonstrated in FIGS. 3E and 6D, the crosslinkers (i.e., gelatin methacrylate) for PAAc-co-NHS ester and the biopolymers (i.e., gelatin or chitosan) in the adhesive material are biodegradable by endogenous enzymes (e.g., collagenase, lysozyme, NAGase) at varying rates. As shown, gelatin typically degrades much faster than chitosan in physiological conditions. Hence, the biodegradation rate of the adhesive material can be controlled desired, e.g., from a week (for the gelatin-based DST) to several months (for the chitosan-based DST) by tuning its composition as demonstrated in FIGS. 3E and 6D.

Figure 8A:
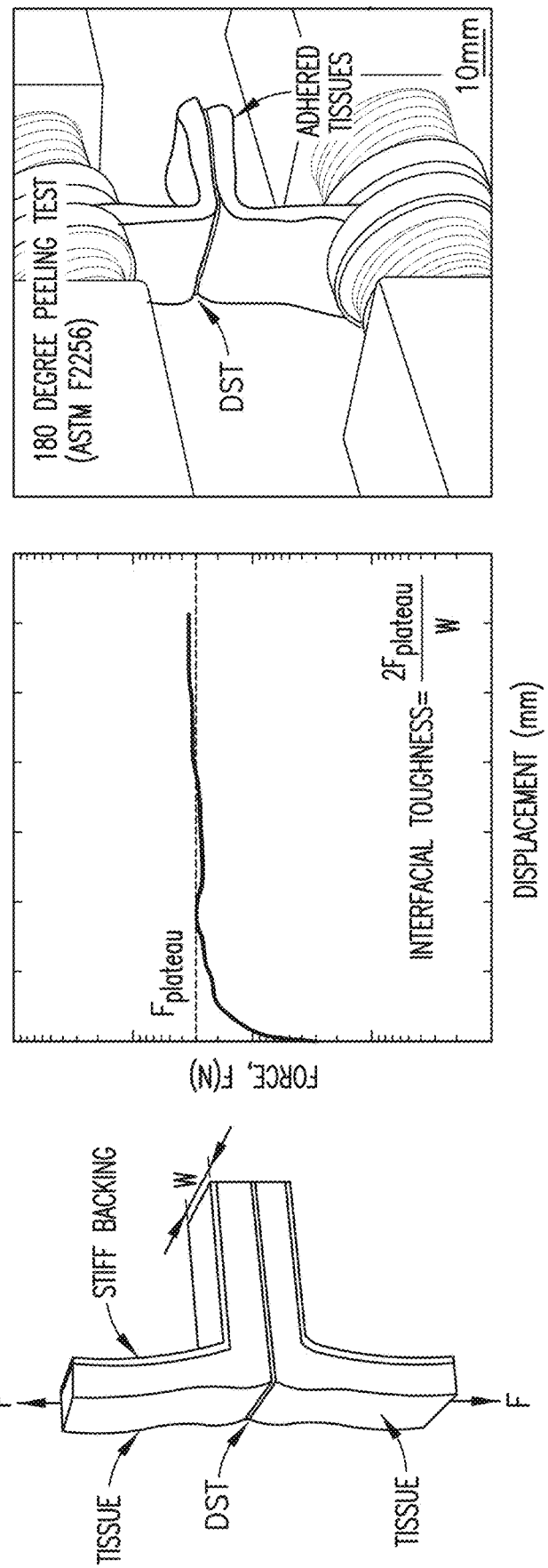
Figure 8B:
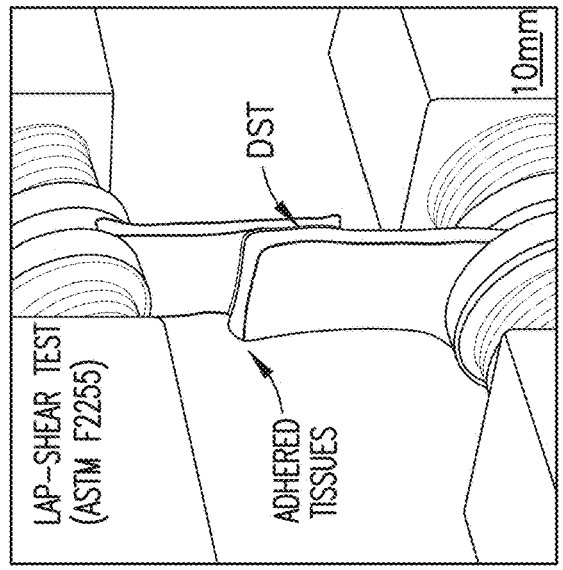
Figure 8B:
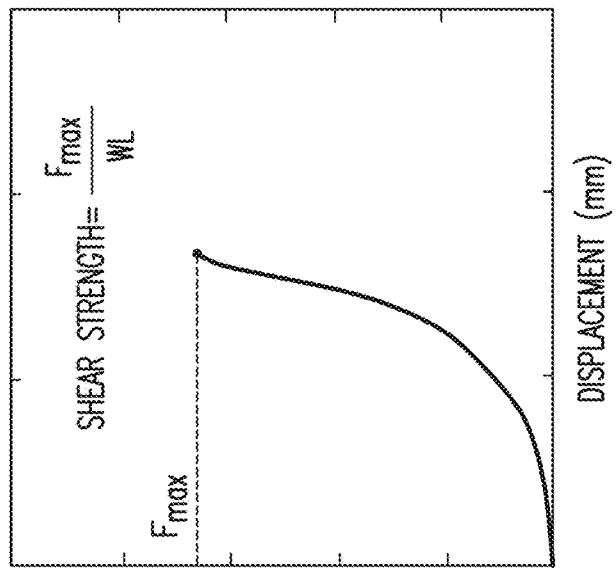
Figure 8B:
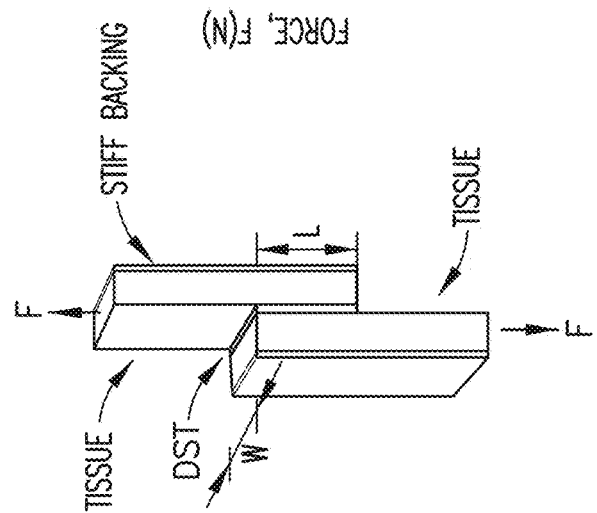
Figure 8C:
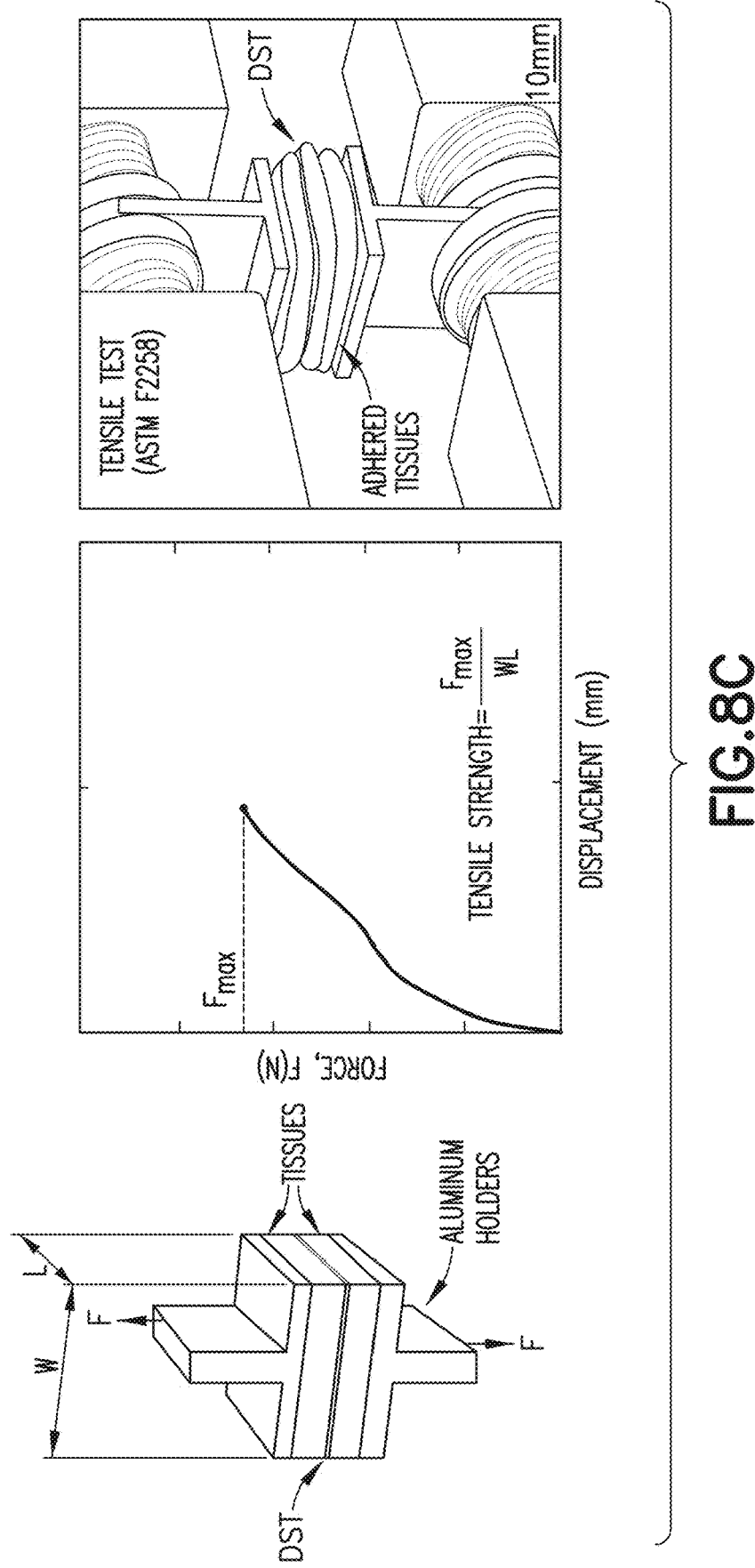
Figure 9A:
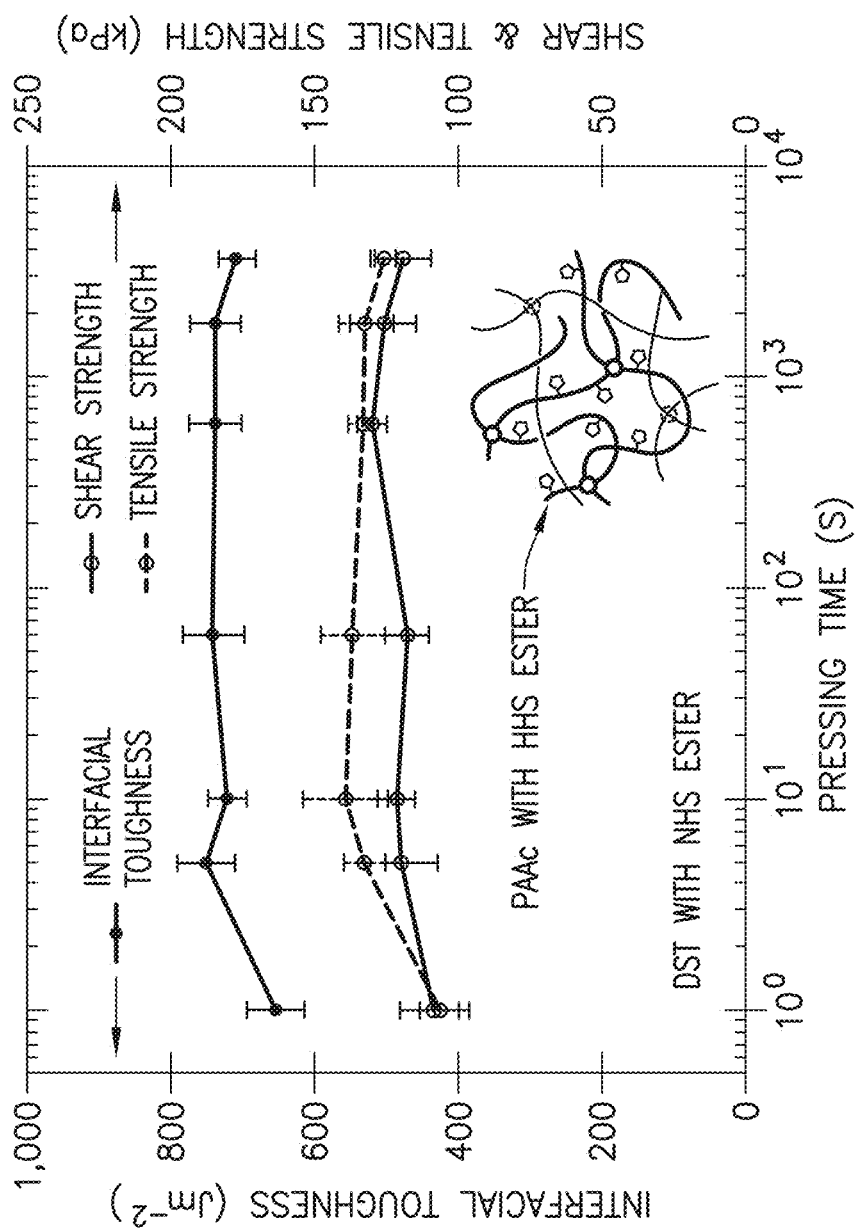
Figure 9B:
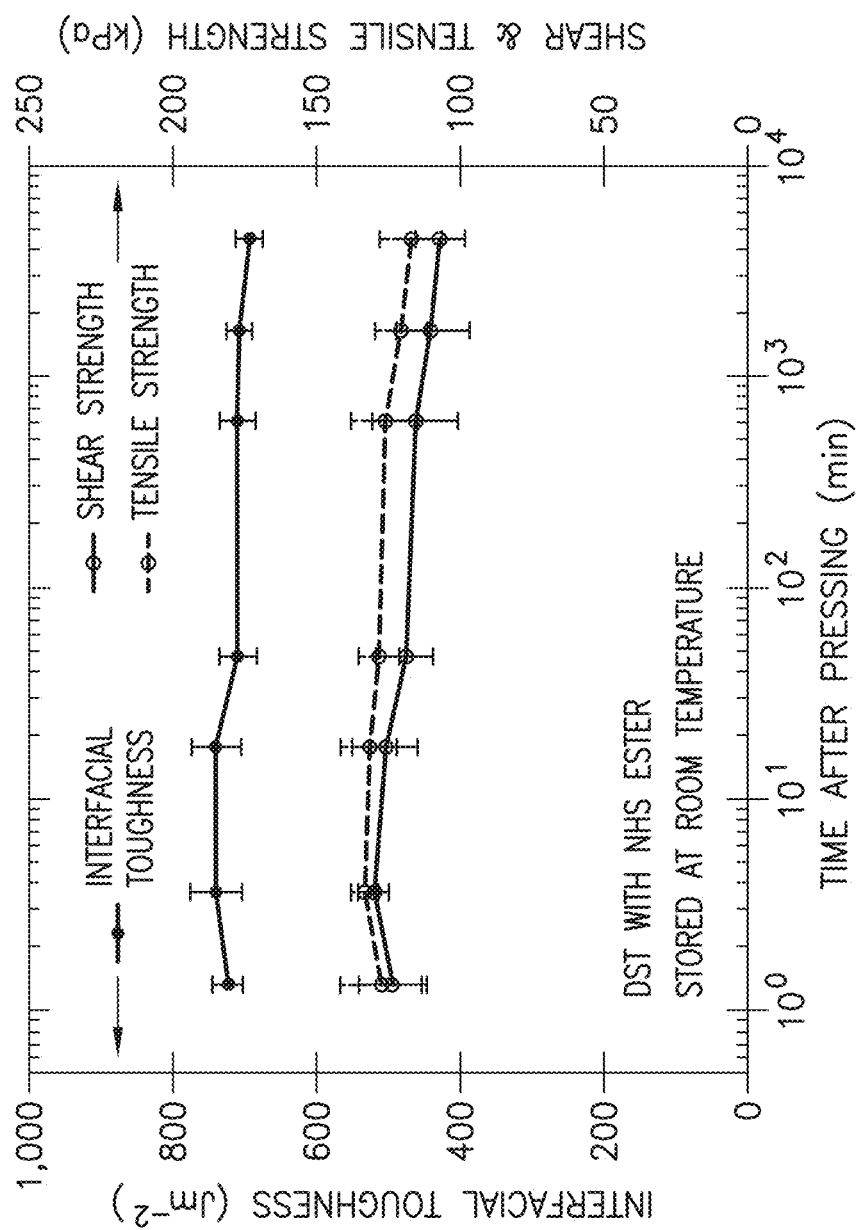
Figure 10A:
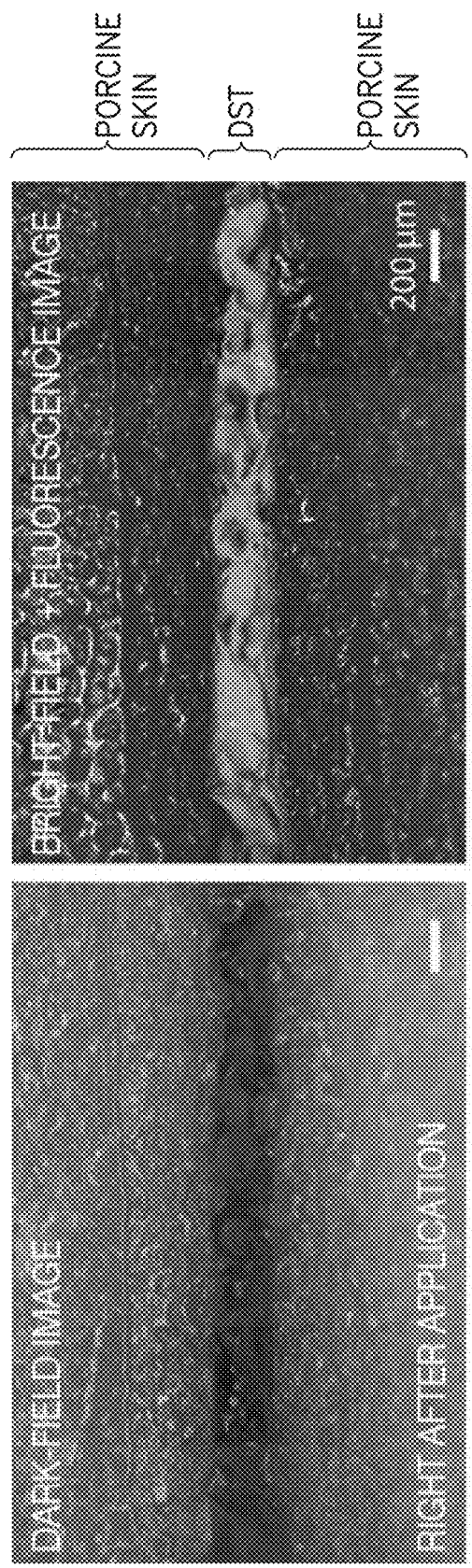
Figure 10B:
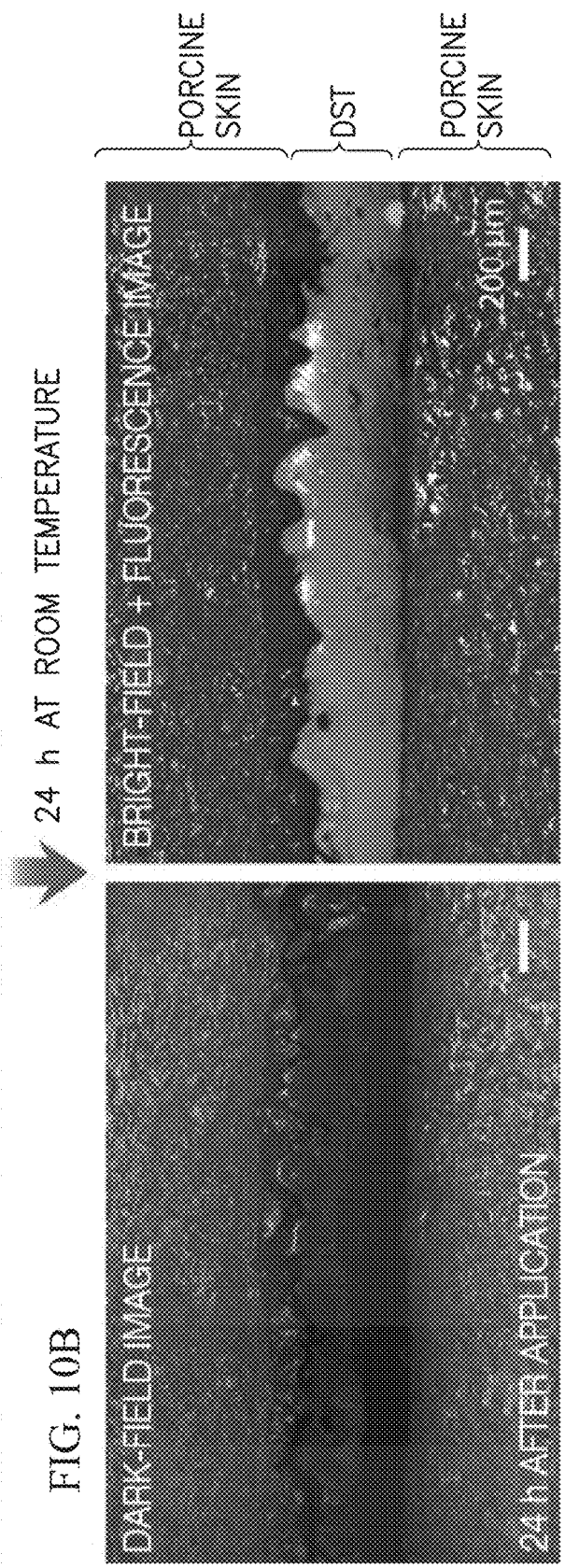

To evaluate the adhesion performance of the dry adhesive material, three different types of mechanical tests were conducted following the testing standards for tissue adhesives (ASTM F2256 for peeling tests, ASTM F2255 for lap-shear tests, and ASTM F2258 for tensile tests) to measure the interfacial toughness (by peeling tests), shear strength (by lap-shear tests), and tensile strength (by tensile tests), respectively (FIG. 8A-C). In these tests, wet pig skins were chosen as the model tissue for adhesion performance evaluation due to its close resemblance to human skin and mechanical robustness. The present invention adhesive material is capable of establishing tough (interfacial toughness over 710 J m$^{-2}$) and strong (shear and tensile strength over 120 kPa) fast adhesion between wet pig skins (e.g. wherein maximum adhesion strength can be attained within and even less than 30-60 seconds) upon contact with gentle pressing for less than 5 seconds (FIG. 9A). The tissues adhered by the adhesive material exhibit stable long-term strong adhesion (over 24 h after an initial 5 sec gentle pressing) with negligible decrease in the measured interfacial toughness and strength as demonstrated in FIGS. 9B and 10. In particular, FIGS. 10A-B illustrate a dry adhesive material in the form of a double sided tape (DST) between adhered tissues according to an embodiment of the present invention. FIG. 10A shows a dark-field and bright-field overlaid with green fluorescence microscope images of pig skins adhered by the DST right after application, and FIG. 10B shows the images 24 h after application. As shown, the DST has further swollen after 24 hours by absorbing the water from the wet tissues while maintaining strong and conformal adhesion between two wet pig skins.

Figure 11:
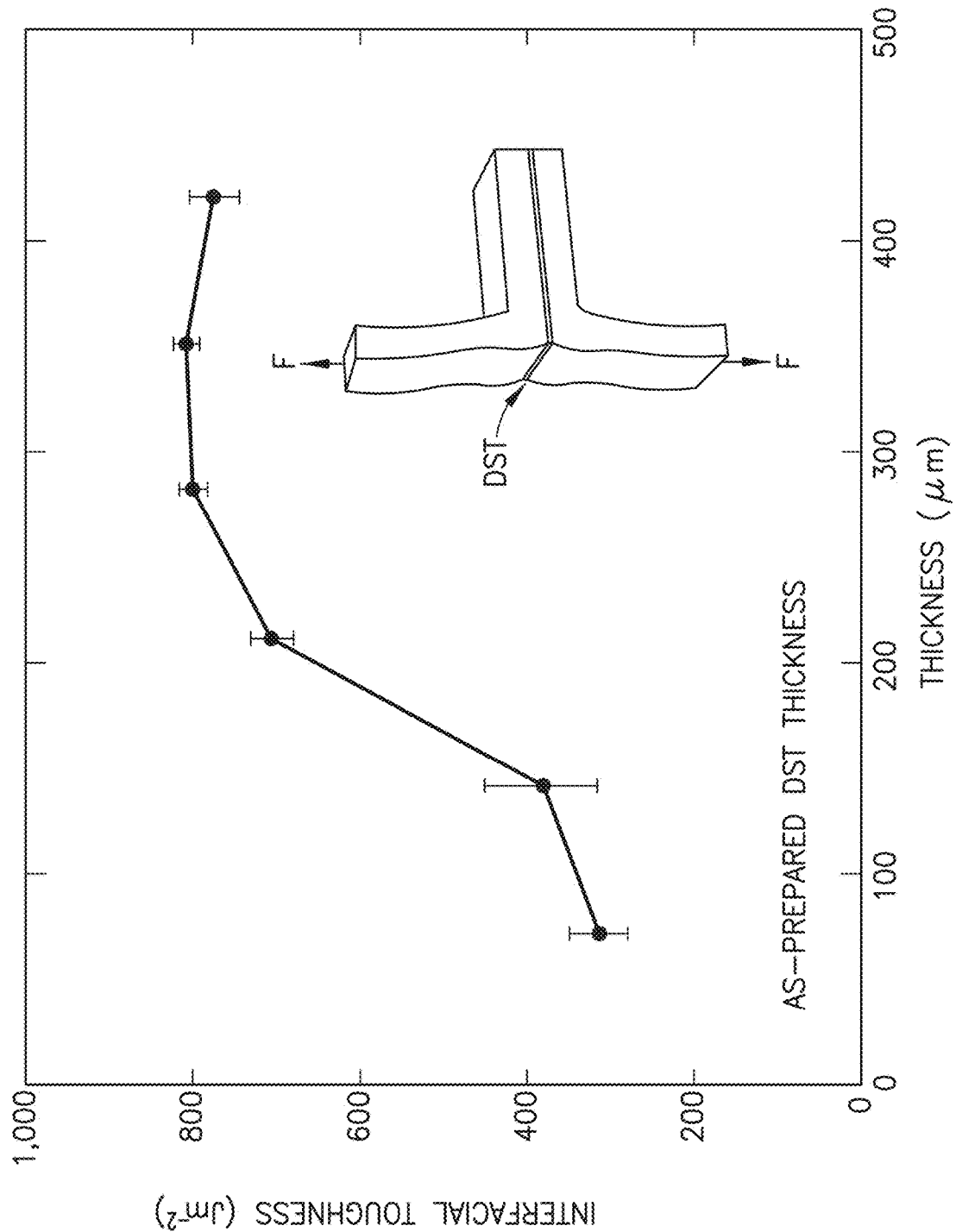
FIG. 11 graphically shows thickness-dependence in adhesion performance of the DST according to an embodiment of the present invention. Values represent the mean and the standard deviation (n=3-5).

The adhesion performance of the dry adhesive material is affected by the thickness of the dry adhesive material. As demonstrated in the FIG. 11 graphs, a thicker dry adhesive material tends to provide higher interfacial toughness between wet pig skins until reaching a plateau value around 800 J m$^{-2}$ with the as-prepared dry adhesive material thickness above 210 μm.

Figure 9C:
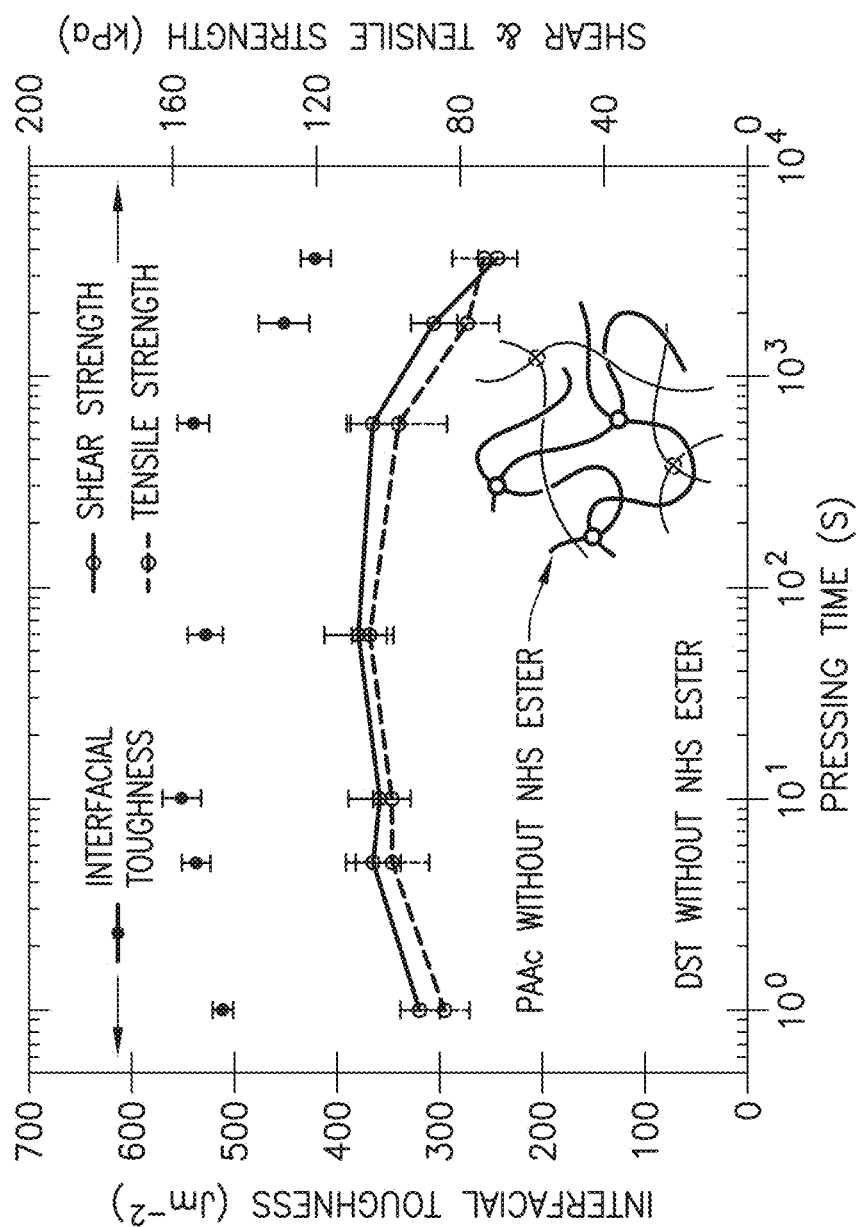
Figure 9D:
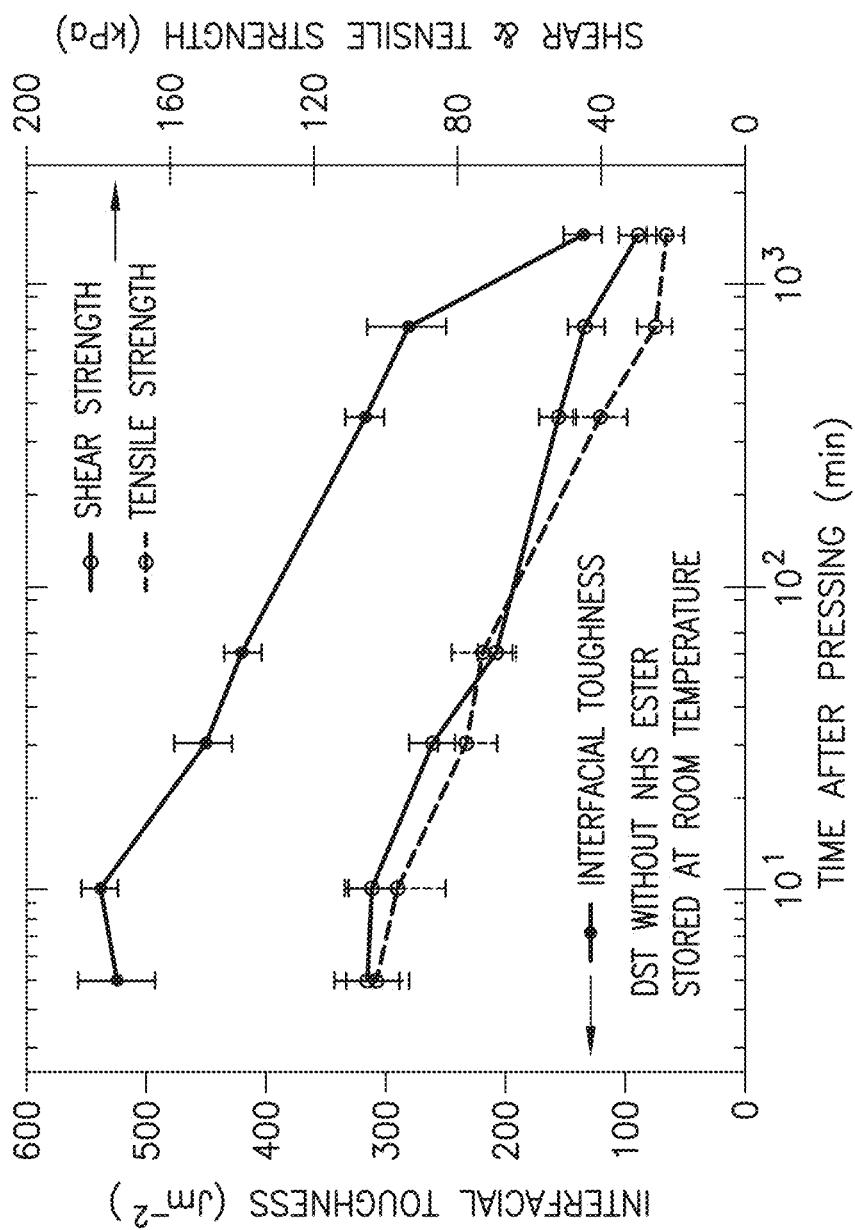

The present invention dry adhesive material forms superior adhesion of wet tissues due to the synergistic combination of drying of interfacial liquid by swelling of the dry adhesive material, the instant temporary crosslinking, and the fast covalent crosslinking. As such that components of the dry adhesive material which provide the drying, swelling, instant temporary crosslinking, and fast covalent crosslinking are important in providing the adhesive properties. For example, the fast covalent bonding after the instant intermolecular bonding in adhesion performance of the dry adhesive material was tested by analyzing the adhesion performance of the dry adhesive material formed without grafted NHS ester in the PAAc. This composition, as shown in FIGS. 9C-D, did not form covalent bonding with the wet tissues. While the dry adhesive material without NHS ester is capable of providing tough (interfacial toughness over 500 J m$^{-2}$) and strong (shear and tensile strength over 80 kPa) adhesion instantly upon application between wet pig skins (FIG. 9C), the adhesion performance shows significant deterioration over time (FIG. 9D). This deterioration is believed to be due to the unstable and temporary nature of the instant intermolecular bonds in wet environments. Hence, the present dry adhesive materials are capable of providing stable strong adhesion on wet surfaces through the inclusion of materials and the use of mechanisms which provide both the instant temporary adhesion and subsequent fast covalent (FIG. 2B).

Figure 9E:
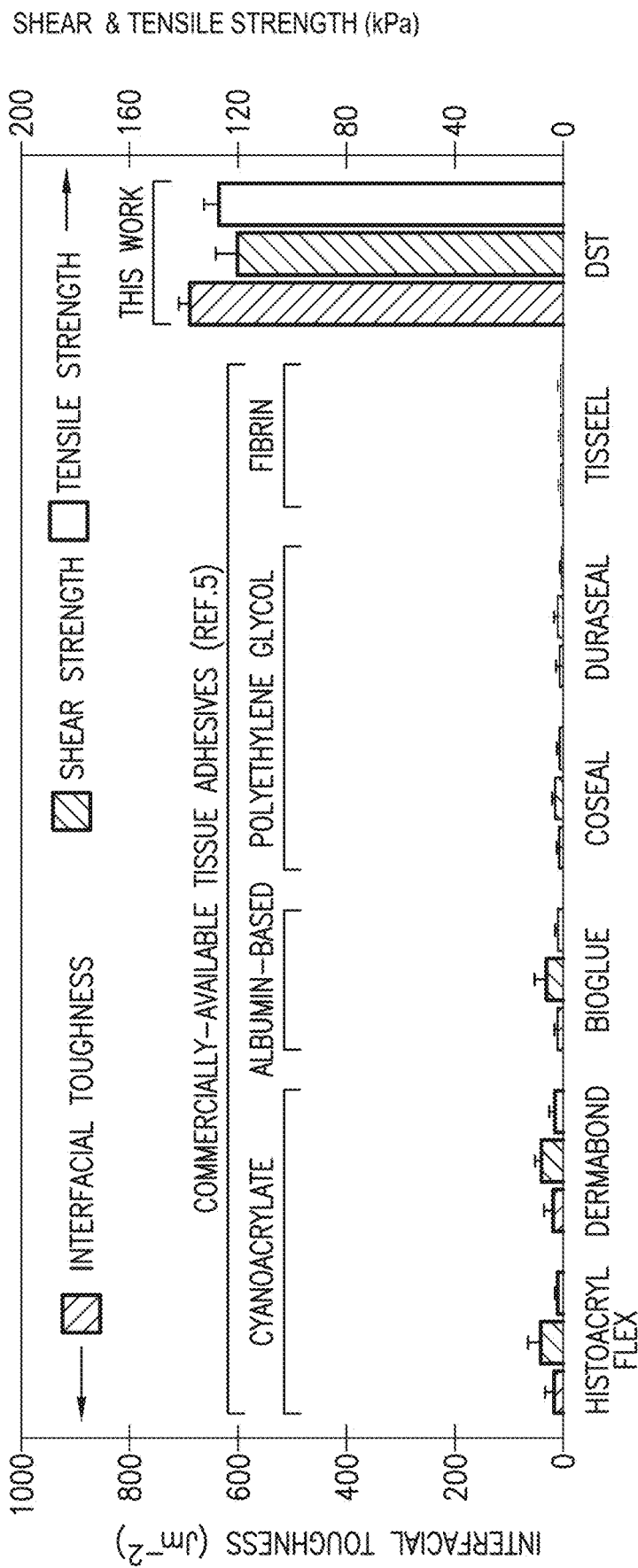
Figure 12:
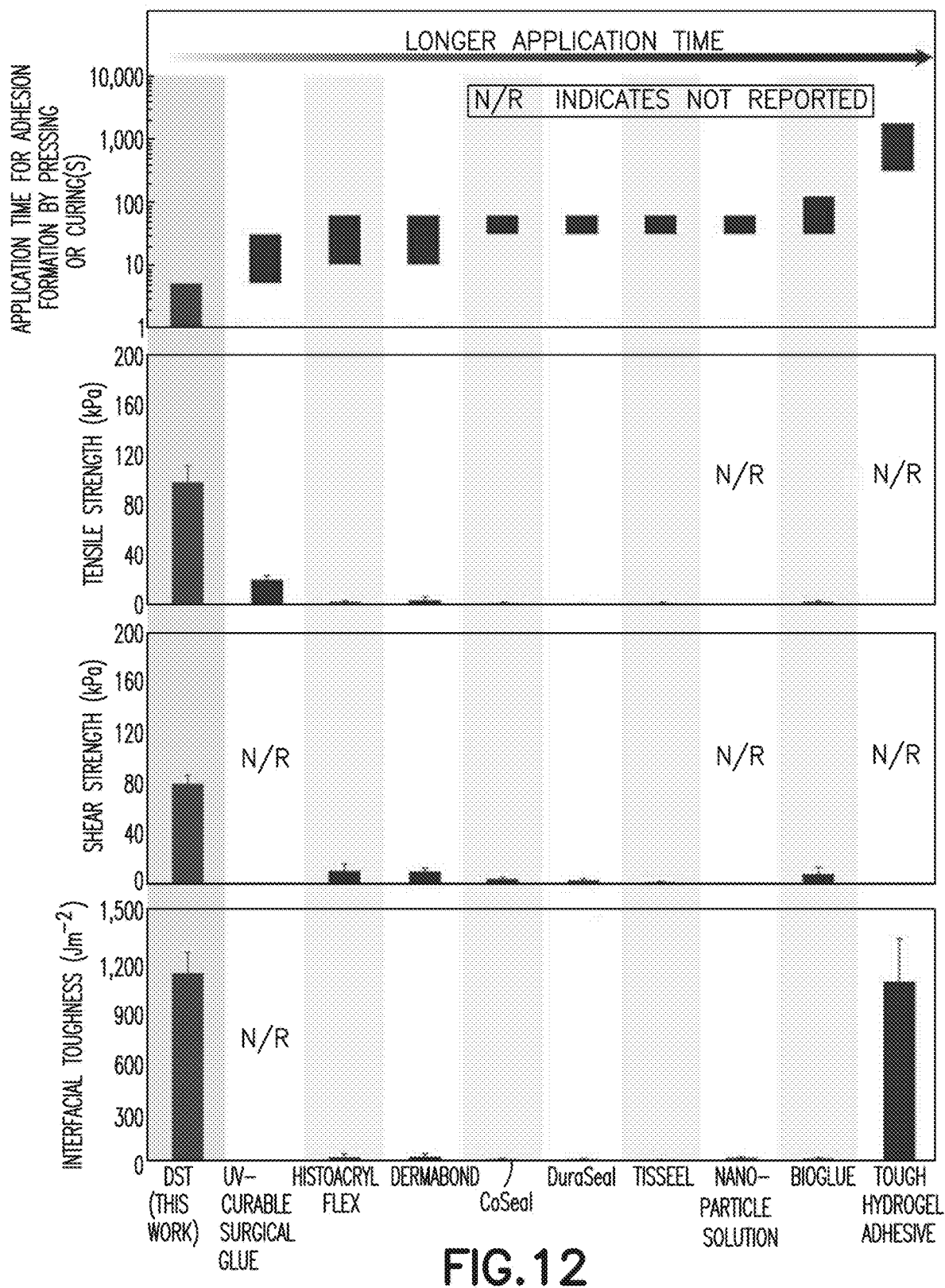
FIG. 12 graphically compares adhesion performances between the DST according to an embodiment of the present invention and some existing tissue adhesives. Values represent the mean and the standard deviation (n=3-5).

The present invention dry adhesive material further provides superior adhesion performance compared to existing tissue adhesives including commercially available cyanoacrylate adhesives (e.g., Histoacryl Flex™, Dermabond™), albumin-based adhesives (e.g., Bioglue™), polyethylene glycol-based adhesives (e.g., CoSeal™, DuraSeal™), fibrin glues (e.g., Tisseel™) as well as nanoparticle solutions and UV-curable surgical glues. These existing tissue adhesives require relatively long time to form adhesion (longer than 1 min) and exhibit limited adhesion performances on wet tissues (interfacial toughness lower than 20 J m$^{-2}$ and shear/tensile strength lower than 10 kPa) (see FIGS. 9E and 12). In FIG. 9E the data for commercially available tissue adhesives is obtained from the literature (See Vakalopoulos, K. A. et al. Mechanical strength and rheological properties of tissue adhesives with regard to colorectal anastomosis: an ex vivo study. *Annals of Surgery* 261, 323-331 (2015)). In FIG. 12, typical values for interfacial toughness, shear and tensile strength, and application time for adhesion formation are compared between the dry adhesive materials (between hydrogel and pig skin) and various existing tissue adhesives. The data for commercially available adhesives in FIG. 12 (Histoacryl Flex™, Dermabond™, CoSeal™, DuraSeal™, Tisseel™, and Bioglue™), UV-curable surgical glue, nanoparticle solution, and tough hydrogel adhesive is obtained from the literatures and the application manuals (for commercially available tissue adhesives)(See Vakalopoulos, K. A. et al. Mechanical strength and rheological properties of tissue adhesives with regard to colorectal anastomosis: an ex vivo study. *Annals of Surgery* 261, 323-331 (2015); Roche, E. T. et al. Soft robotic sleeve supports heart function. *Science Translational Medicine* 9, eaaf3925 (2017); Rose, S. et al. Nanoparticle solutions as adhesives for gels and biological tissues. Nature 505, 382-385 (2014); Li, J. et al. Tough adhesives for diverse wet surfaces. Science 357, 378-381 (2017); Reece, T. B., Maxey, T. S. & Kron, I. L. A prospectus on tissue adhesives. *The American Journal of Surgery* 182, S40-S44 (2001)). N/R indicates not reported. As demonstrated, the present invention dry adhesive material provides much higher interfacial toughness (up to 1,150 J m$^{-2}$), shear and tensile strength (up to 160 kPa) than existing tissue adhesives within less than 5 sec (see FIGS. 8E and 12).

The present invention dry adhesive material is applicable for a wide range of wet tissues including skin, tendon, stomach, muscle, heart, and liver. In particular, FIG. 13A-G illustrates the instant strong adhesion of a variety of wet tissues by the present dry adhesive materials. For example, FIG. 13A graphically demonstrates the interfacial toughness and shear and tensile strength between various tissues adhered by the dry adhesive material, with FIGS. 13B-G showing photographs of various tissues adhered by the dry adhesive material for pig skin 13B, tendon 13C, stomach 13D, muscle 13E, heart 13F, and liver 13G.

Figure 13A:
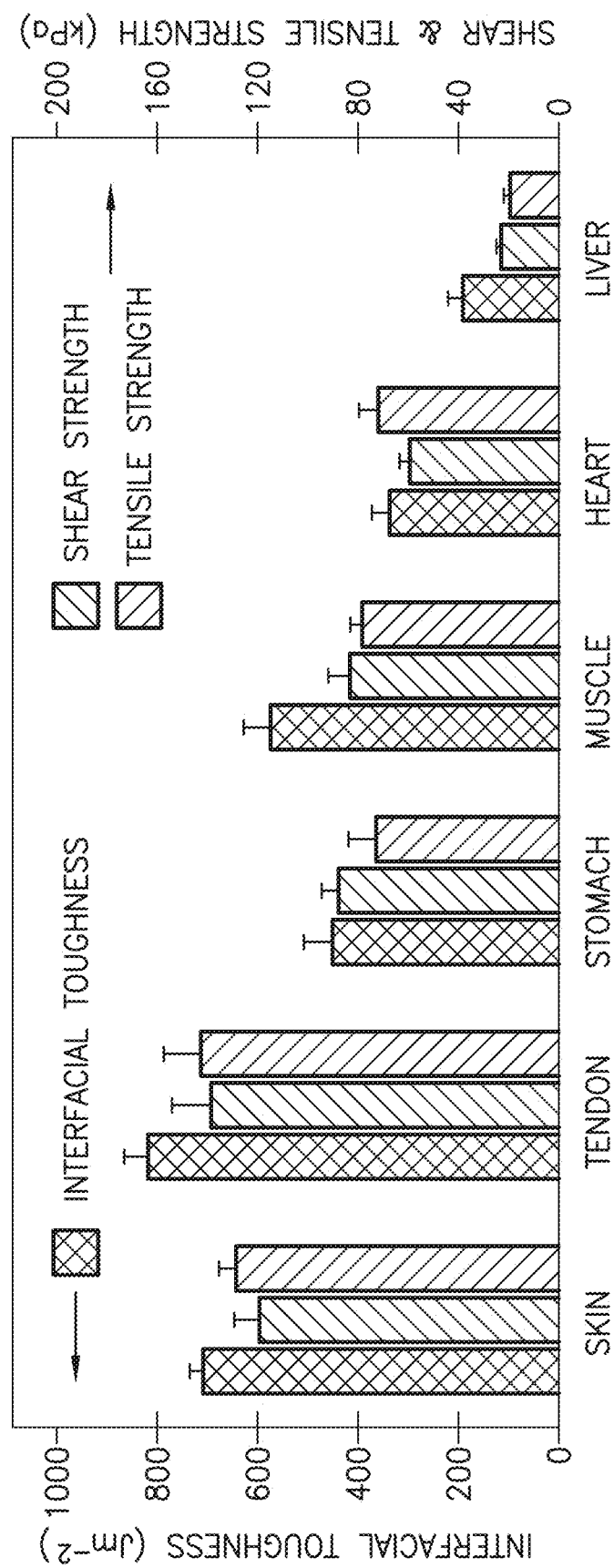
FIGS. 13A-N illustrate the instant strong adhesion of a variety of wet tissues and engineering solids by the DST according to an embodiment of the present invention, wherein FIG. 13A graphically shows the interfacial toughness and shear and tensile strength between various tissues adhered by the DST.
Figure 13B:
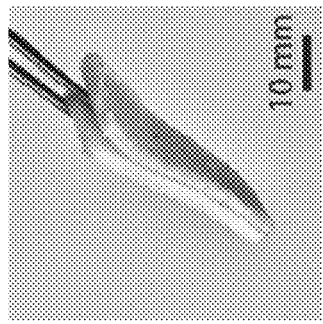
FIGS. 13B-G show photographs of various tissues adhered by the DST, FIG. 13H graphically show interfacial toughness and shear and tensile strength between pig skin and various engineering solids by the DST.
Figure 13C:
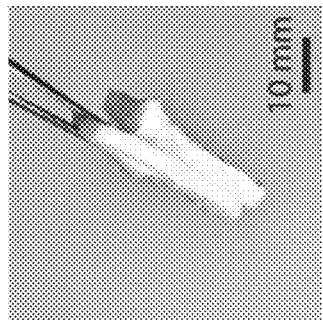
Figure 13D:
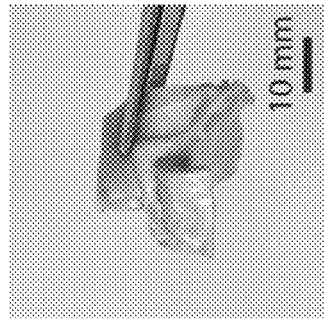
Figure 13E:
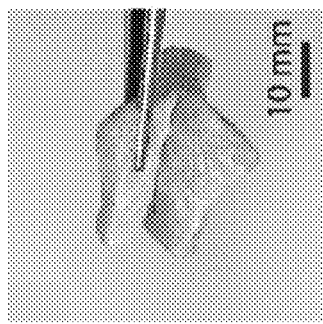
Figure 13F:
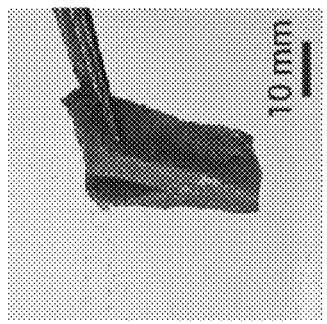
Figure 13G:
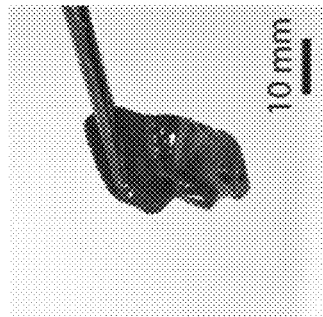
Figure 13H:
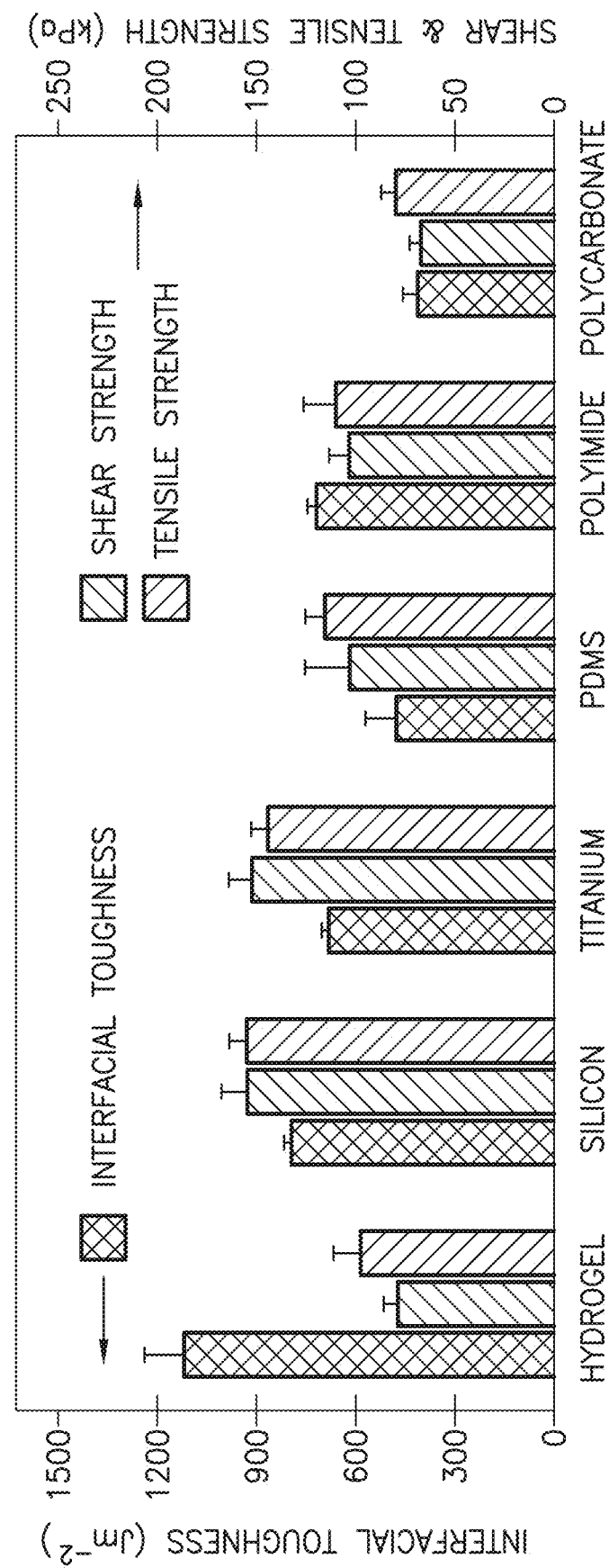
Figure 13K:
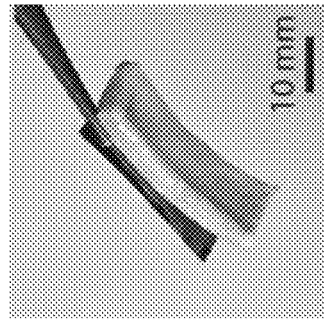
Figure 13N:
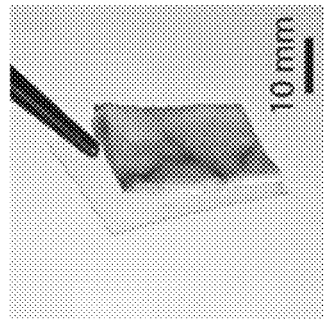
Figure 13J:
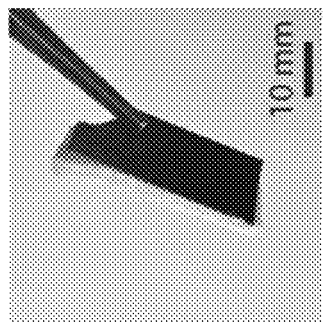
Figure 13M:
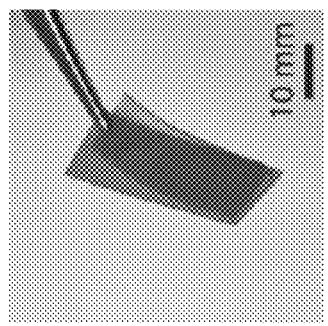
Figure 13I:
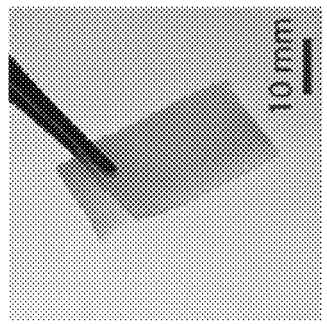
Figure 13L:
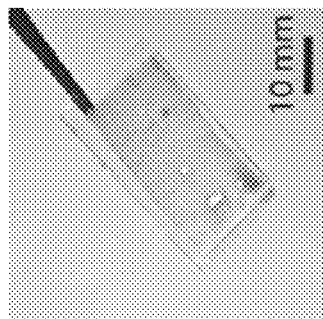

The remarkable versatility of the present intention dry adhesive material can also provide instant tough adhesion between wet tissues and various engineering solids including hydrogel, silicon, titanium, polydimethylsiloxane (PDMS), polyimide, and polycarbonate, which are unachievable with existing tissue adhesives (FIGS. 13H-N). In other words, the present dry adhesive material can be used to attach one or more various engineering solids to one or more wet tissue surfaces (see FIGS. 13I-N). As shown, such attachment to one or more wet tissue surfaces provides high interfacial toughness and shear and tensile strength between pig skin and the various engineering solids (FIG. 13H).

Figure 14A:
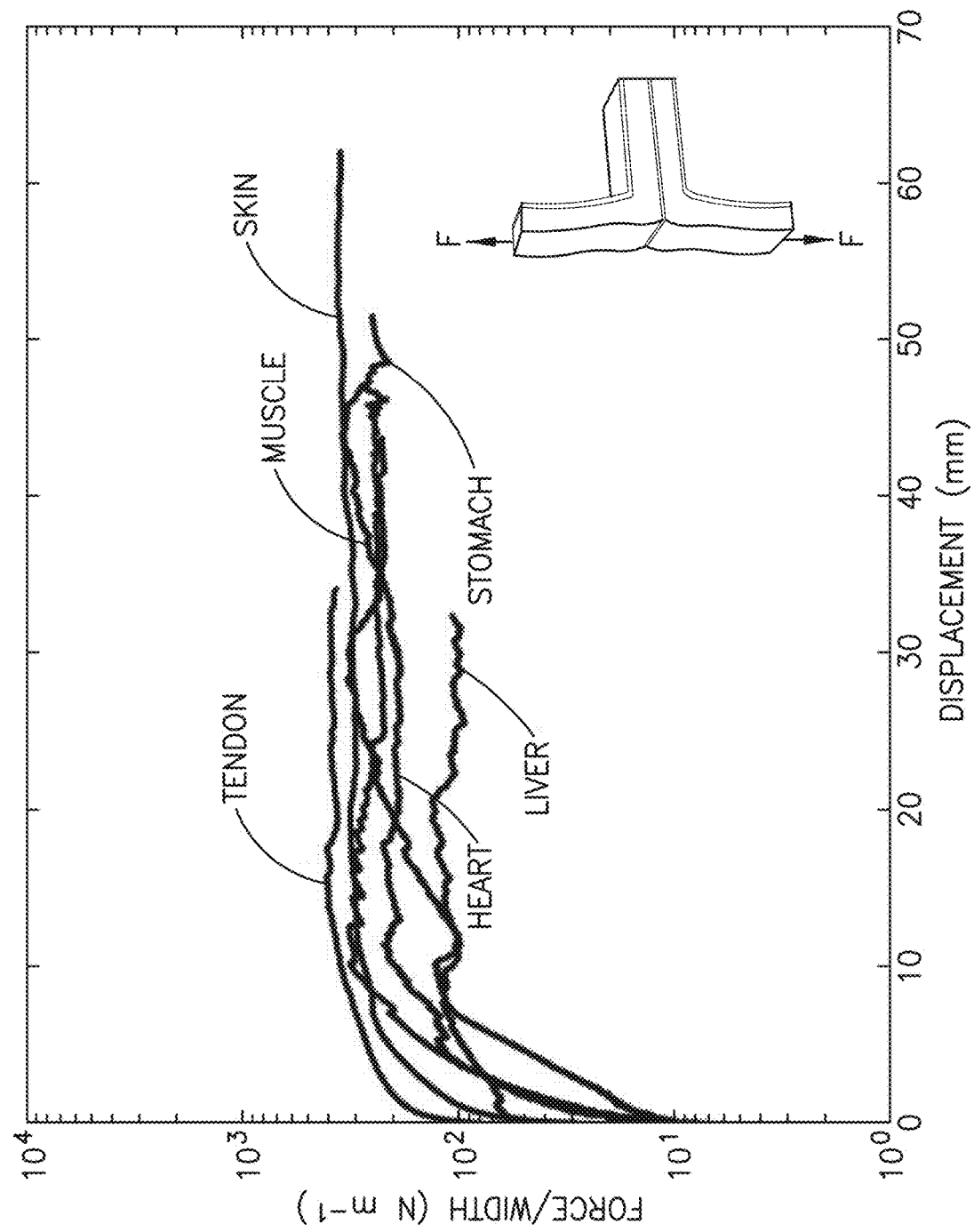

FIGS. 14A-C further graphically illustrate representative curves for mechanical tests of various tissues adhered by the dry adhesive material according to embodiments of the present invention, wherein FIG. 14A show a force/width vs. displacement curves for 180-degree peeling tests of various tissues adhered by the DST, FIG. 14B shows shear stress vs. displacement curves for lap-shear tests of various tissues adhered by the DST, and FIG. 14C shows tensile stress vs. displacement curves for tensile tests of various tissues adhered by the DST. As demonstrated, the present dry adhesive material provides high interfacial toughness (over 710 J m$^{-2}$ for skin, 820 J m$^{-2}$ for tendon, 450 J m$^{-2}$ for stomach, 570 J m$^{-2}$ for muscle, 340 J m$^{-2}$ for heart, 190 J m$^{-2}$ for liver) and high shear and tensile strength (over 120 kPa for skin, 140 kPa for tendon, 70 kPa for stomach, 80 kPa for muscle, 70 kPa for heart, 20 kPa for liver) (FIGS. 13A and 14).

Figure 15A:
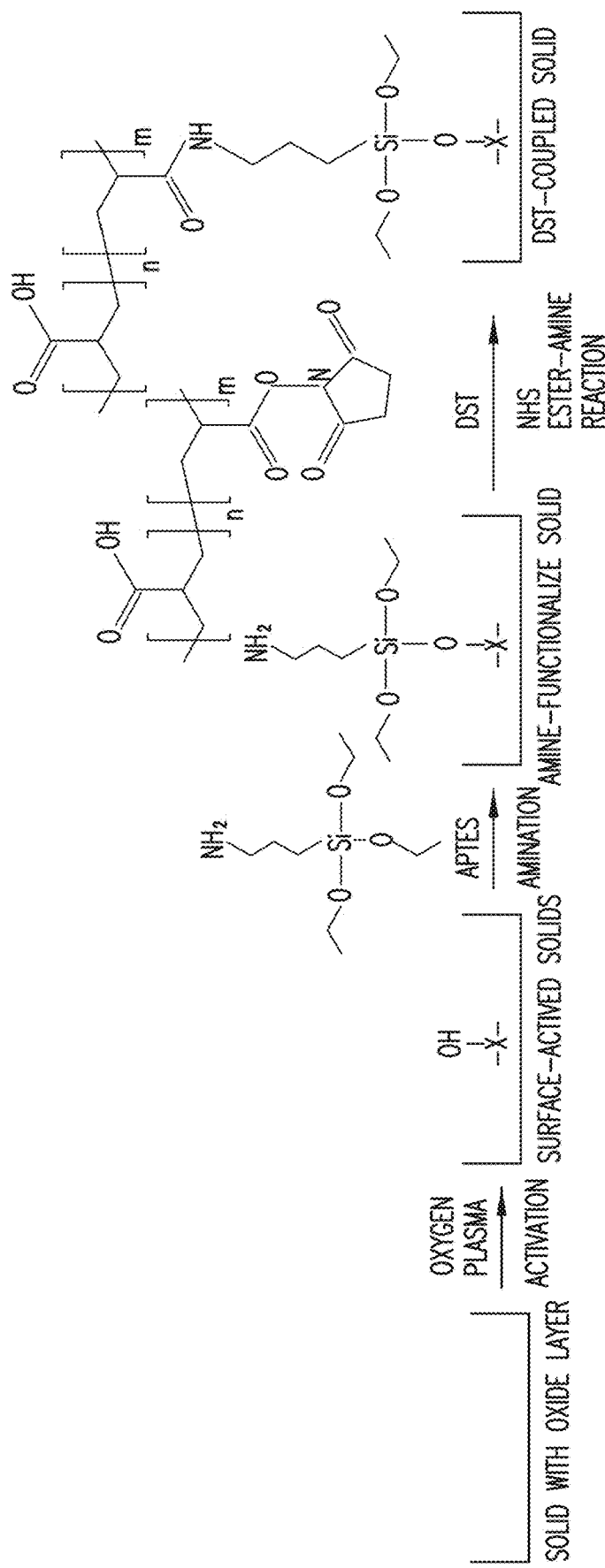
Figure 15B:
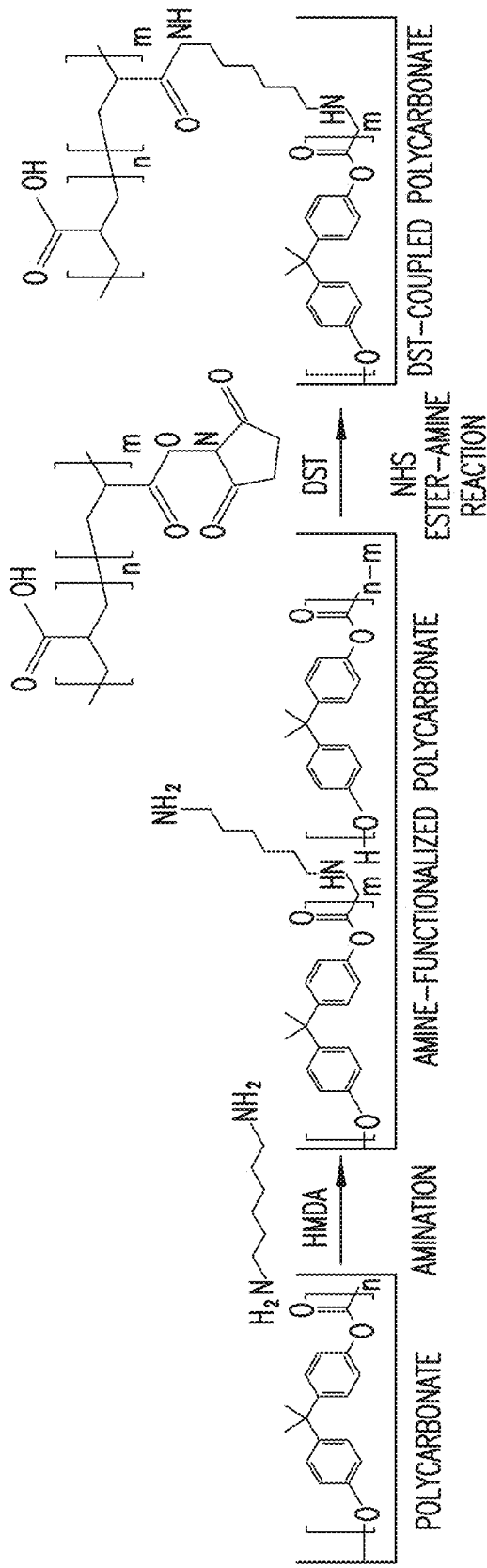
Figure 15C:
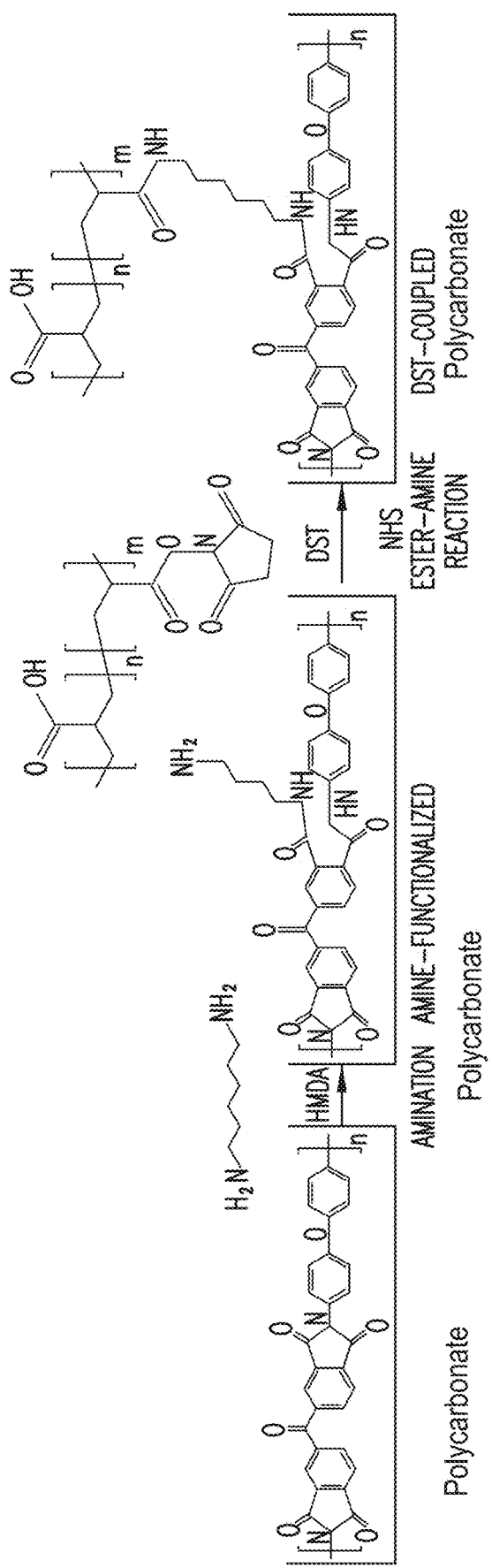

As shown in FIGS. 15A-C, attachment of the various engineering solids to wet tissue using the present dry adhesive material was achieved by first functionalizing one or more surfaces of the engineering solid with primary amines in order to provide fast covalent coupling with the dry adhesive material. Thereafter, the dry adhesive material is adhered to the desired wet tissue surface as described herein. In particular, FIG. 15A depicts a schematic illustration for primary amine functionalization of silicon, titanium, and PDMS, and subsequent covalent coupling between the primary amine groups and the NHS ester groups in the DST according to an embodiment of the present invention. FIG. 15B shows a schematic illustration for primary amine functionalization of polycarbonate, and subsequent covalent coupling between the primary amine groups and the NHS ester groups in the DST according to an embodiment of the present invention. FIG. 15C shows a schematic illustration for primary amine functionalization of polyimide, and subsequent covalent coupling between the primary amine groups and the NHS ester groups in the DST according to an embodiment of the present invention. Thus, the present materials and methods provide for the attachment of a variety of engineering solids to wet surfaces.

Figure 16A:
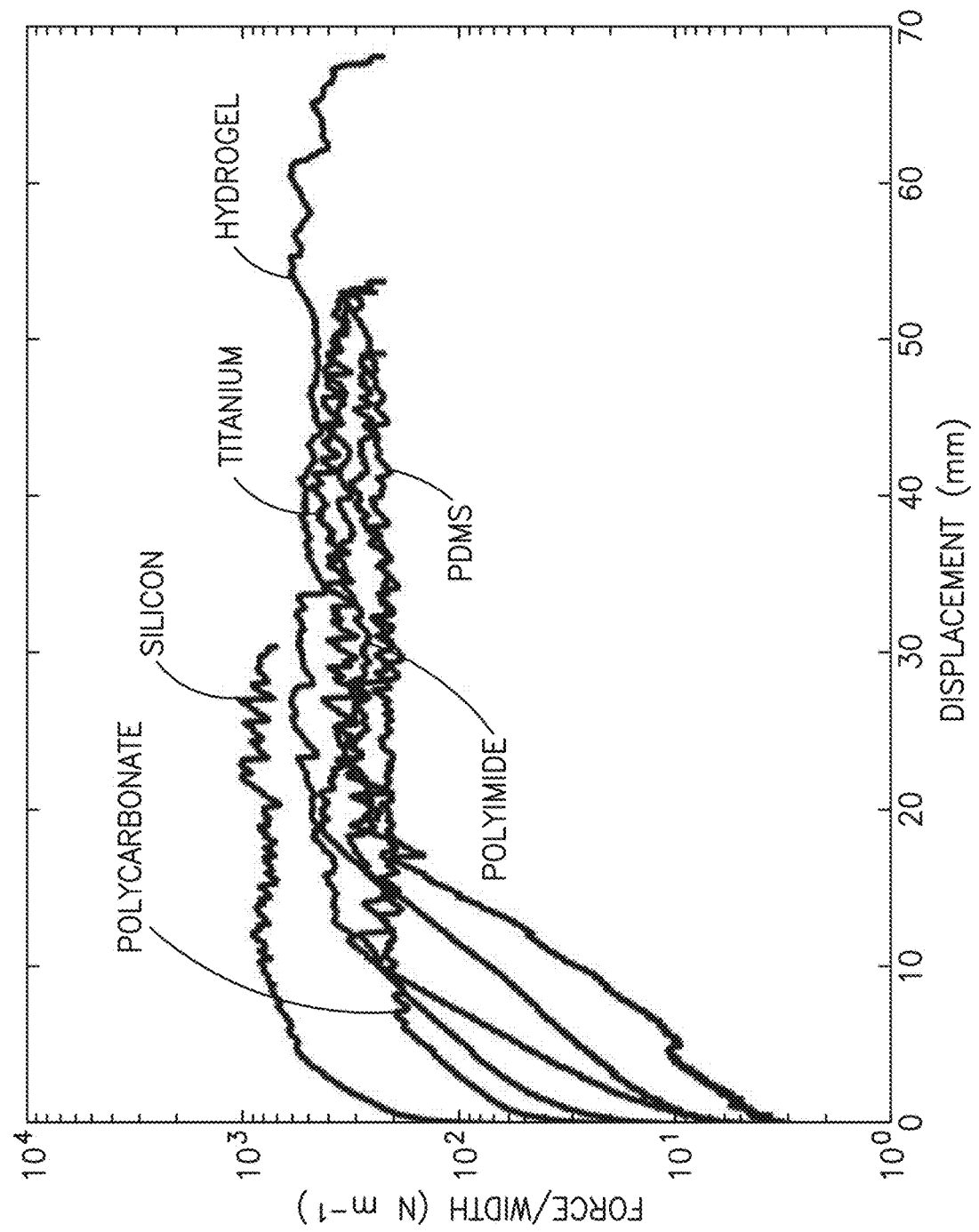
FIGS. 16A-C graphically illustrate representative curves for mechanical tests of pig skins and various engineering solids adhered by the DST according to an embodiment of the present invention, wherein FIG. 16A show force/width vs. displacement curves for 180-degree peeling tests and 90-degree peeling tests (for silicon) of pig skins and various engineering solids adhered by the DST, FIG. 16B show shear stress vs. displacement curves for lap-shear tests of pig skins and various engineering solids adhered by the DST, FIG. 16C show tensile stress vs. displacement curves for tensile tests of pig skins and various engineering solids adhered by the DST.
Figure 16C:
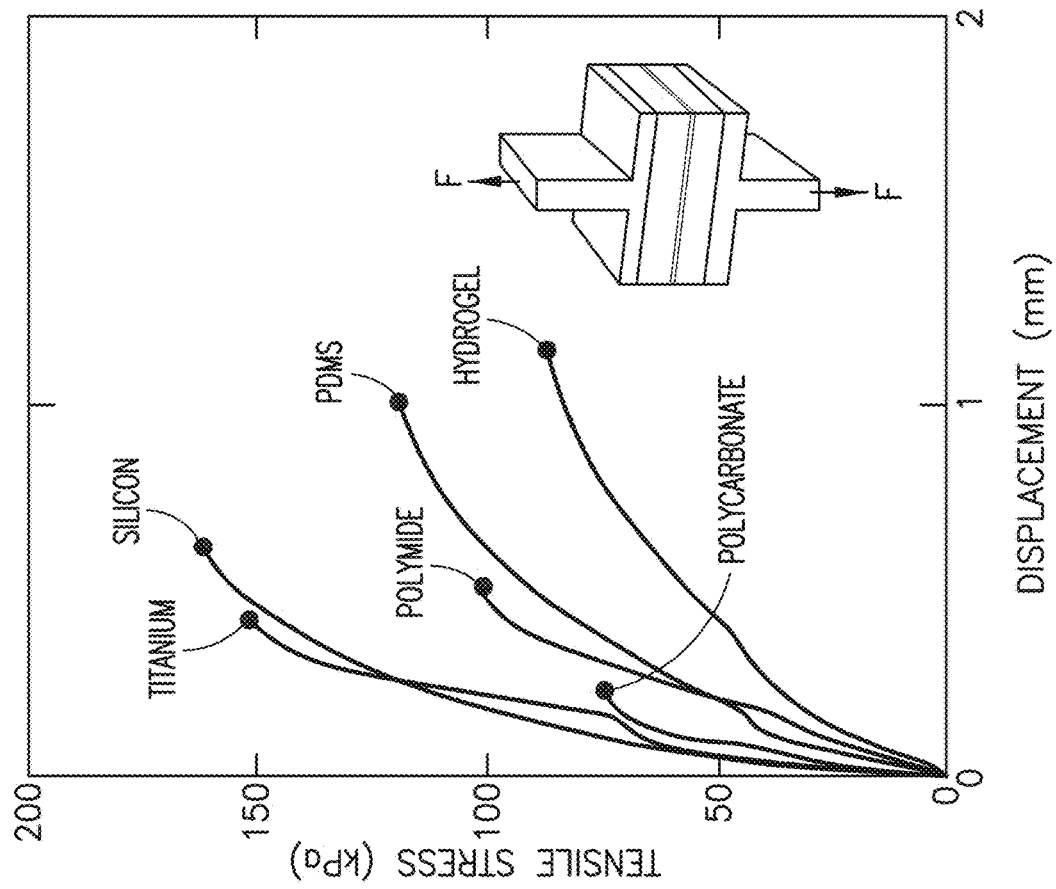
Figure 16B:
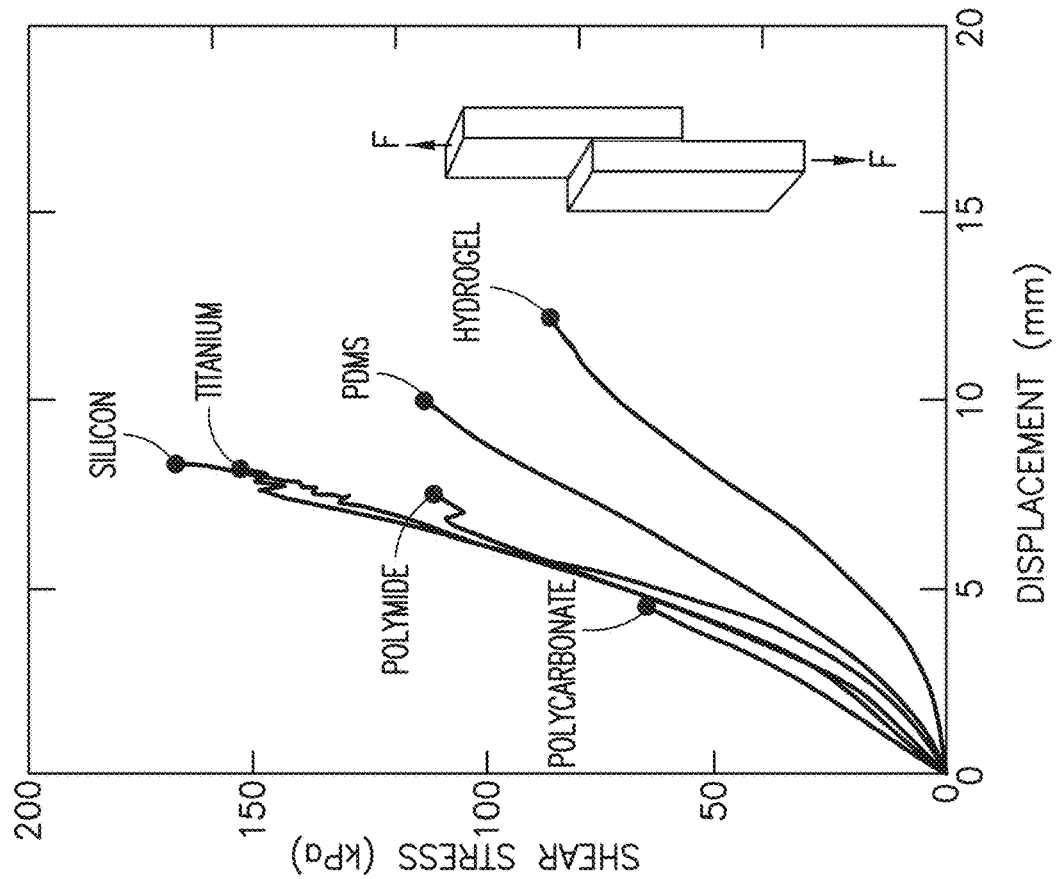
Figure 17A:
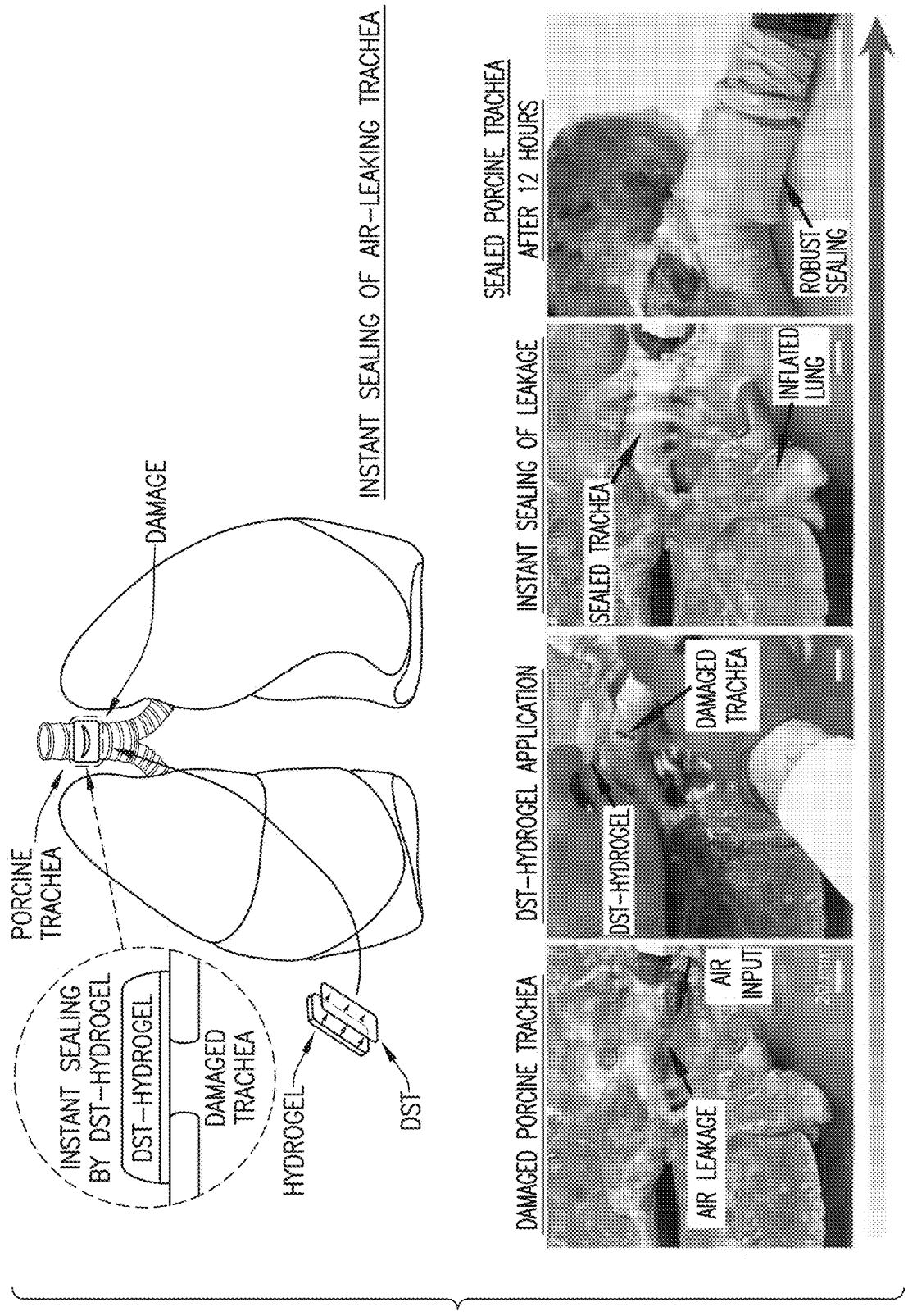
Figure 17B:
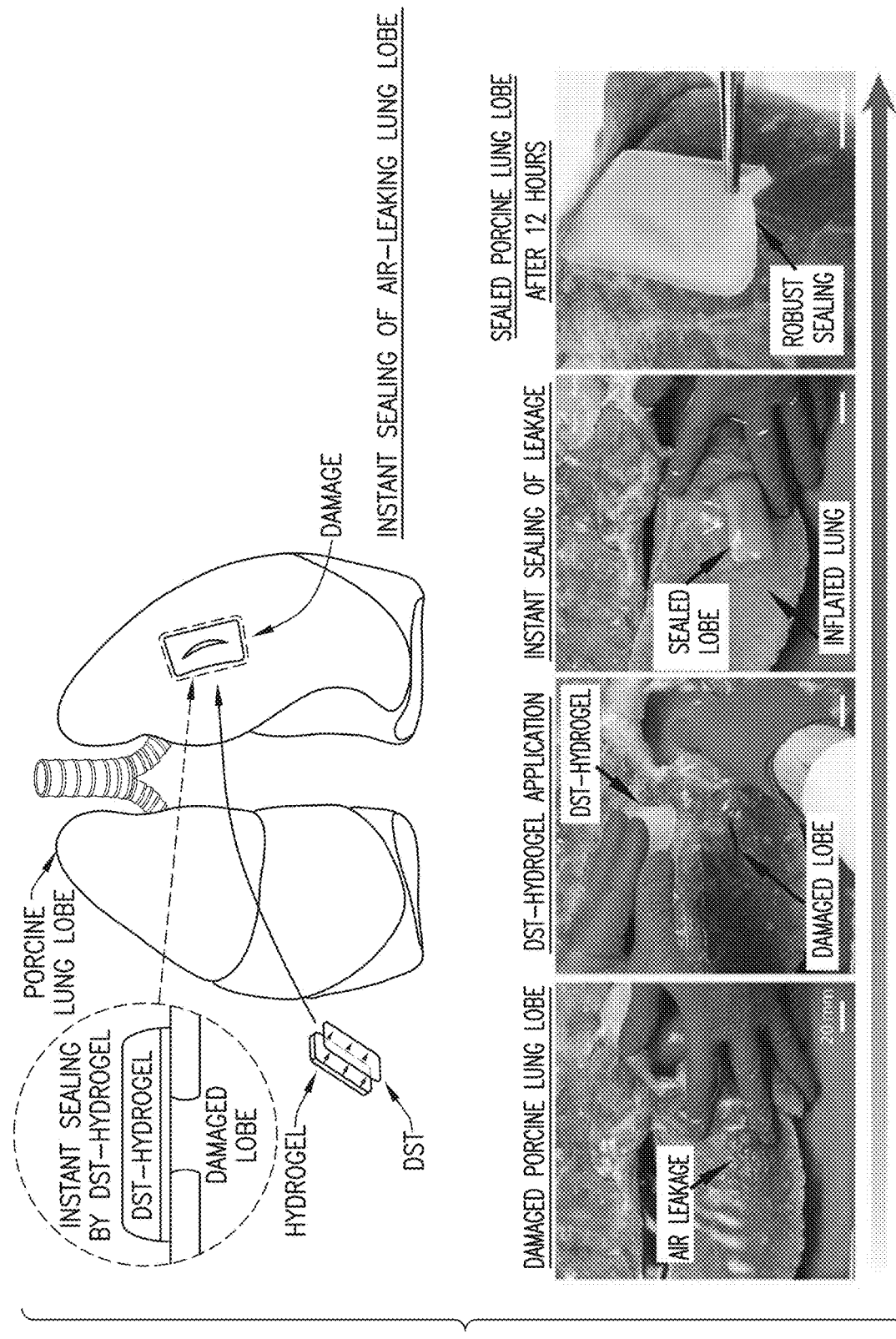
Figure 17C:
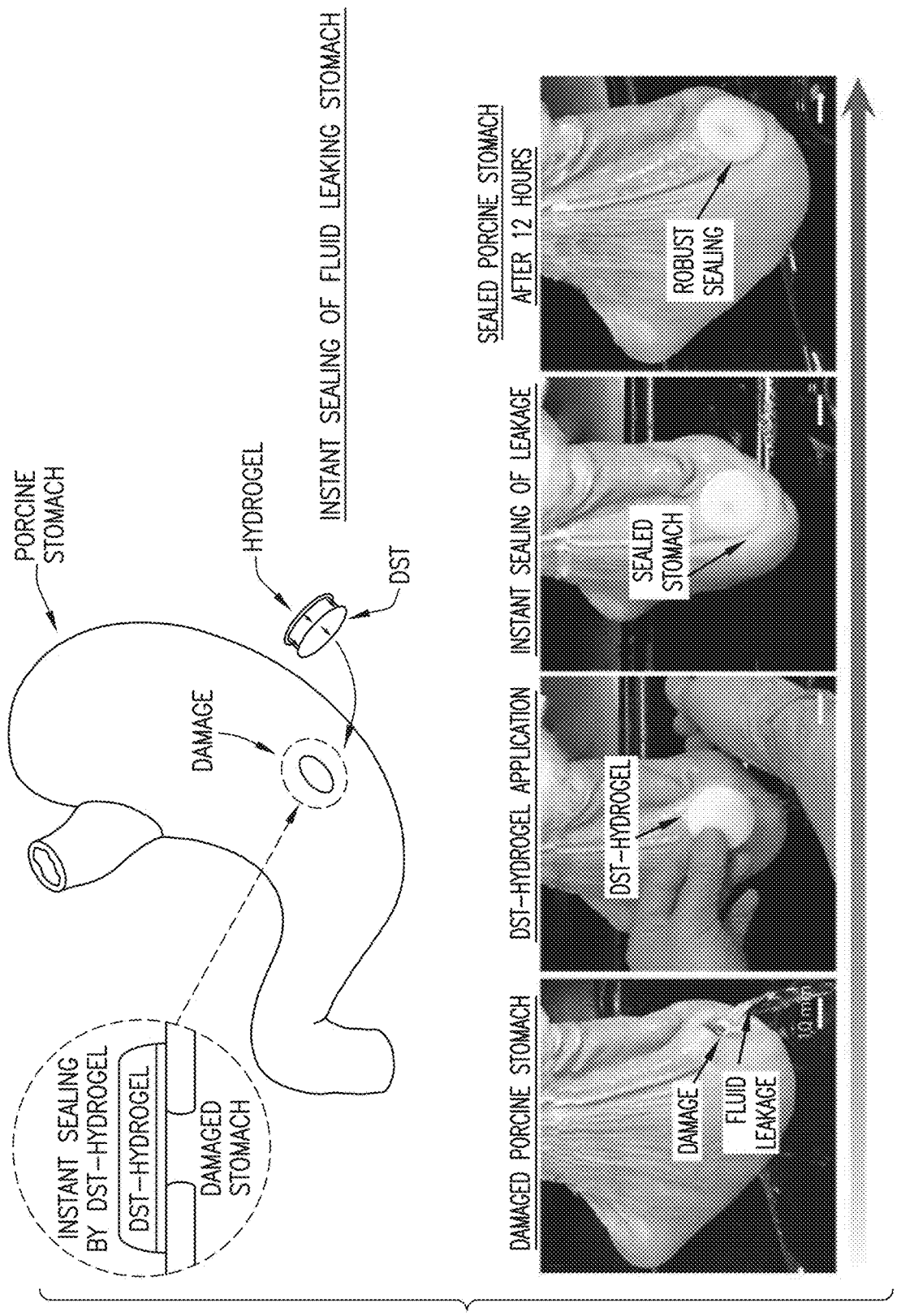
Figure 17D:
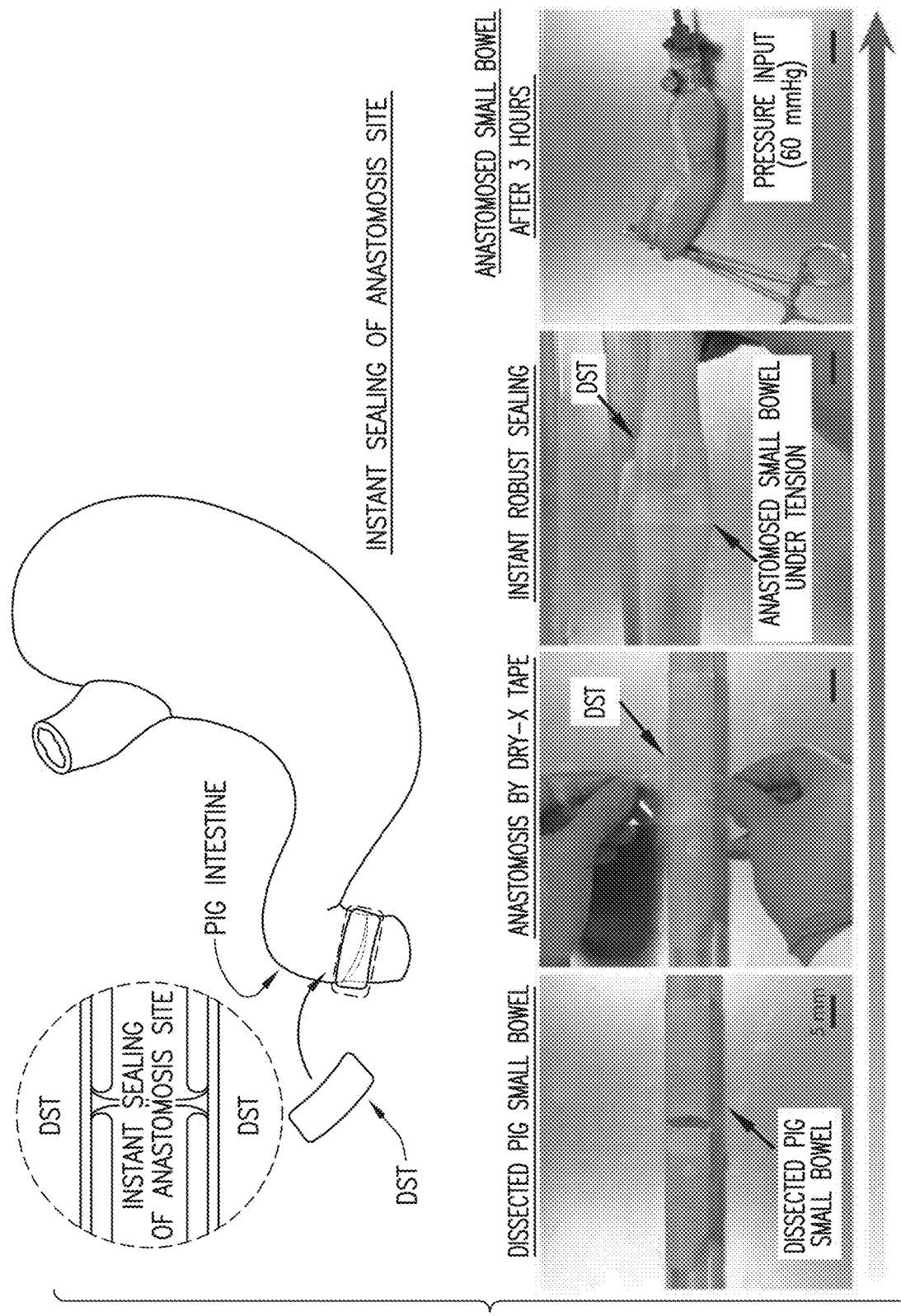

Adhesion performance of such composites (wherein composites refers to the present invention dry adhesive material with one or more engineering solid attached thereto) was evaluate by adhering the composites to wet pig skins (FIG. 16). The adhesion between the wet tissues and various engineering solids by the dry adhesive material exhibited high interfacial toughness (over 1,150 J m$^{-2}$ for hydrogel, 800 J m$^{-2}$ for silicon, 680 J m$^{-2}$ for titanium, 480 J m$^{-2}$ for PDMS, 720 J m$^{-2}$ for polyimide, 410 J m$^{-2}$ for polycarbonate) and high shear and tensile strength (over 80 kPa for hydrogel, 160 kPa for silicon, 150 kPa for titanium, 100 kPa for PDMS, 100 kPa for polyimide, 70 kPa for polycarbonate) (see FIG. 13H).

The capabilities and versatility of the present invention dry adhesive material can thus enable a broad range of unprecedented functions such as instant sealing of damaged tissues and attachments of various devices on wet dynamic tissues (FIG. 17). In an ex vivo test, an air-leaking pig trachea and a lung lobe with a cut was quickly sealed within 1 minute by the present invention dry adhesive material with a hydrogel patch adhered thereto (a composite dry adhesive material with hydrogel patch disposed and adhered thereon), thereby recovering the function of the air-leaking pig trachea without air leakage (FIG. 17A-B). Similarly, a fluid-leaking pig stomach with a hole of 1 cm in diameter was quickly sealed within 1 minute by the present invention dry adhesive material with a hydrogel patch adhered thereto (a composite dry adhesive material with hydrogel patch disposed and adhered thereon), readily stopping the leakage of flowing water (FIG. 17C). Furthermore, the instant and strong adhesion capability of the DST enables facile repair of damaged porcine intestine to form fluid-tight anastomosis (FIG. 17D). This quick sealing of damaged tissues by the present invention dry adhesive material, thus, may find particular utility in surgical repair or closure of wounds as a promising alternative to suturing or stapling.

Figure 18A:
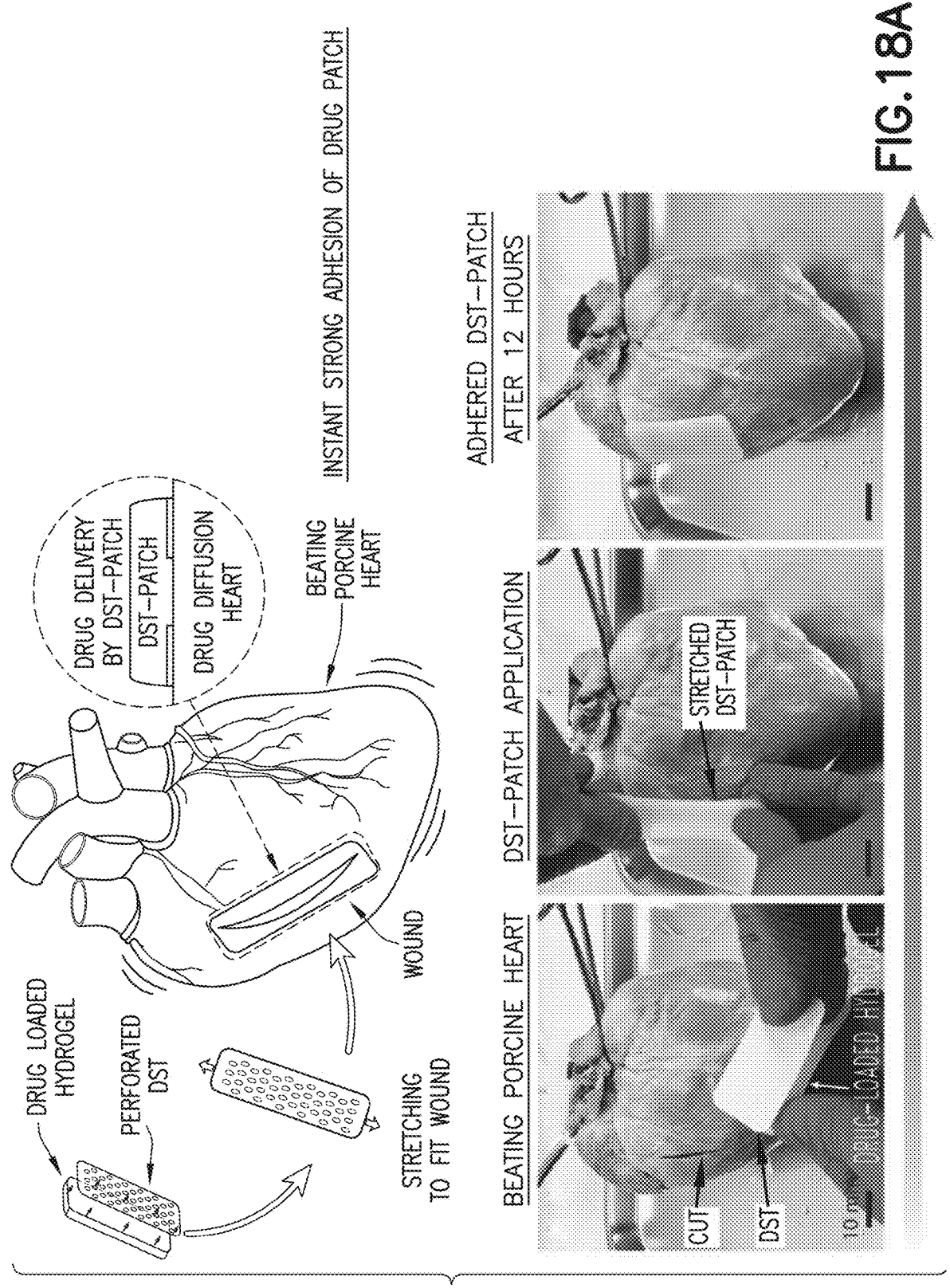
Figure 18B:
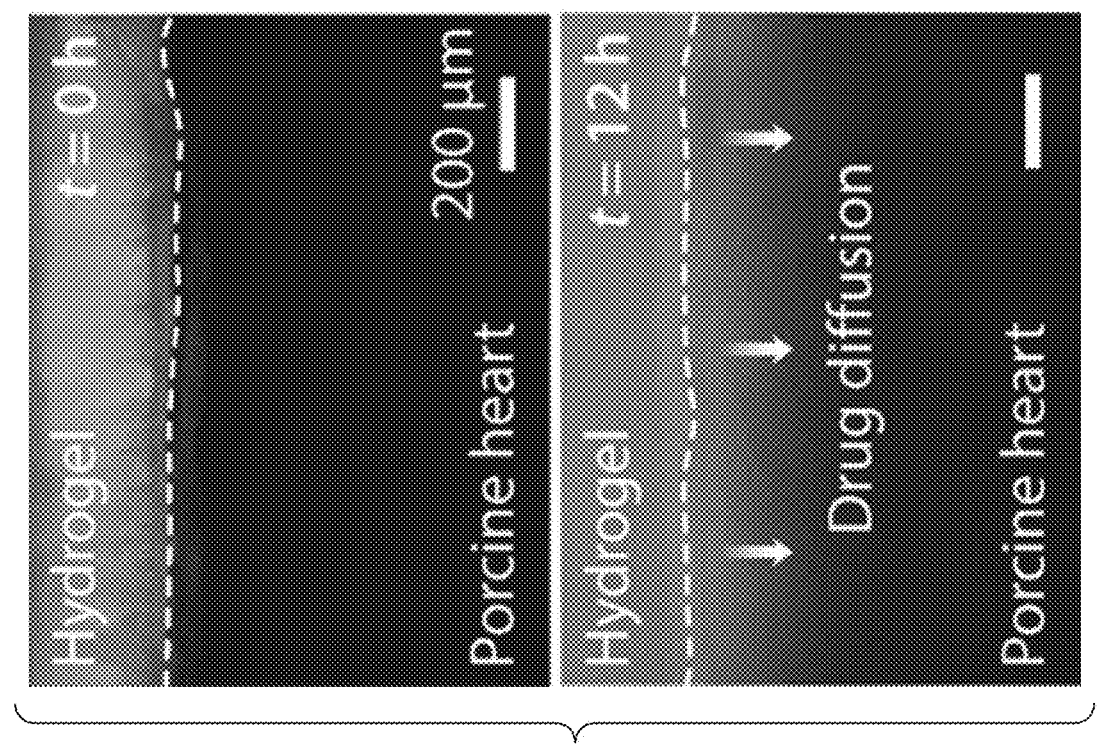

The quick and strong adhesion properties of the dry adhesive material are also highly desirable for attachments of various functional devices on dynamic and deformable tissues, including but not limited to, skin, tendon, and heart. For example, the dry adhesive material can be used to adhere a fluorescein-loaded hydrogel on a beating pig heart with one or more cuts to demonstrate the function of attaching drug-delivery devices on dynamic wet tissues (FIG. 18A). This was accomplished by forming a composite which included the dry adhesive material with the drug delivery device(s) attached to one or more sides of the dry adhesive material, and subsequently by adhering the composite to the dynamic wet tissue. In this example, pressurized air inputs were input into the ex vivo pig heart to mimic heart beats. The flexibility in fabrication of the dry adhesive material further slows for the use of a perforated dry adhesive material to facilitate the delivery of one or more materials (as demonstrated in FIG. 18A, a mock-drug fluorescein) from the drug delivery device(s) toward wet tissue on which the dry adhesive material is attached (e.g., heart tissue as demonstrated in FIG. 18A). Notably, the high stretchability and quick adhesion of the dry adhesive material enable adaptive application of a drug device (e.g. a drug patch) by stretching the DST-patch to match or correspond closely to the size and shape of the cut in the target wet tissue (e.g. a beating pig heart in FIG. 18A). As demonstrated, the adhered DST-patch was capable of maintaining adhesion without any detachment on the beating heart for over 12 hours to achieve progressive delivery of the drug toward the heart tissue (FIG. 18B).

Figure 18C:
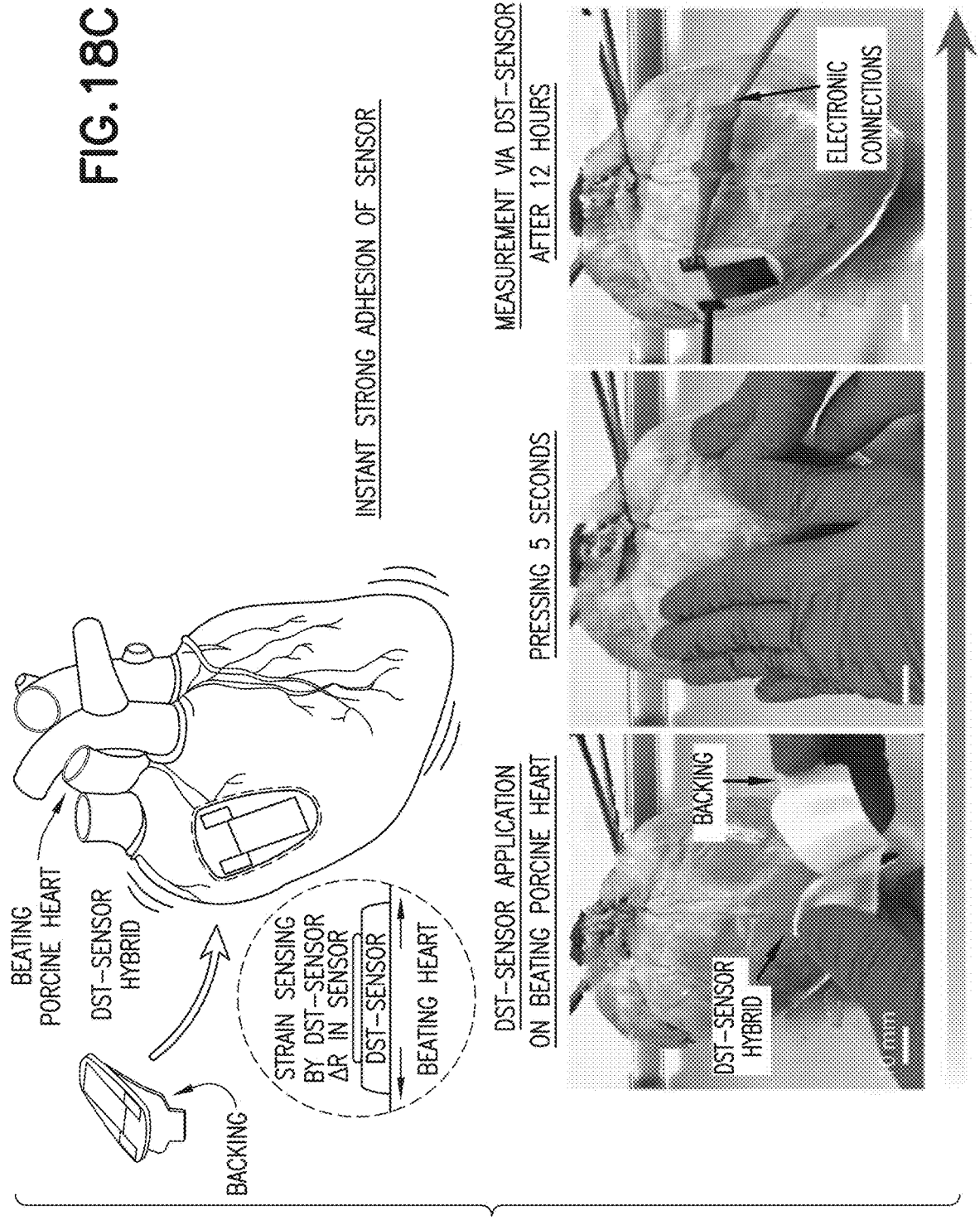
Figure 18D:
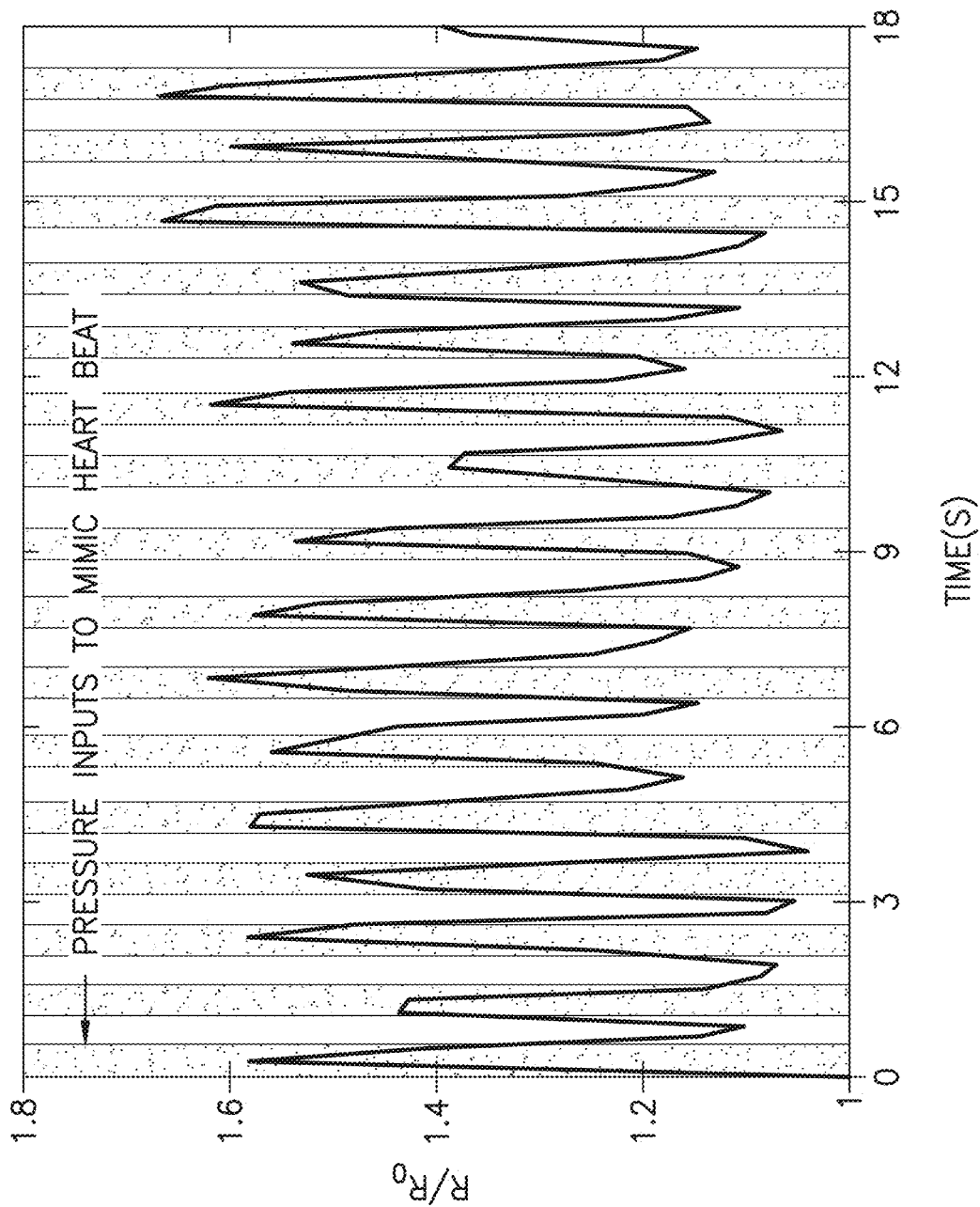
Figure 19:
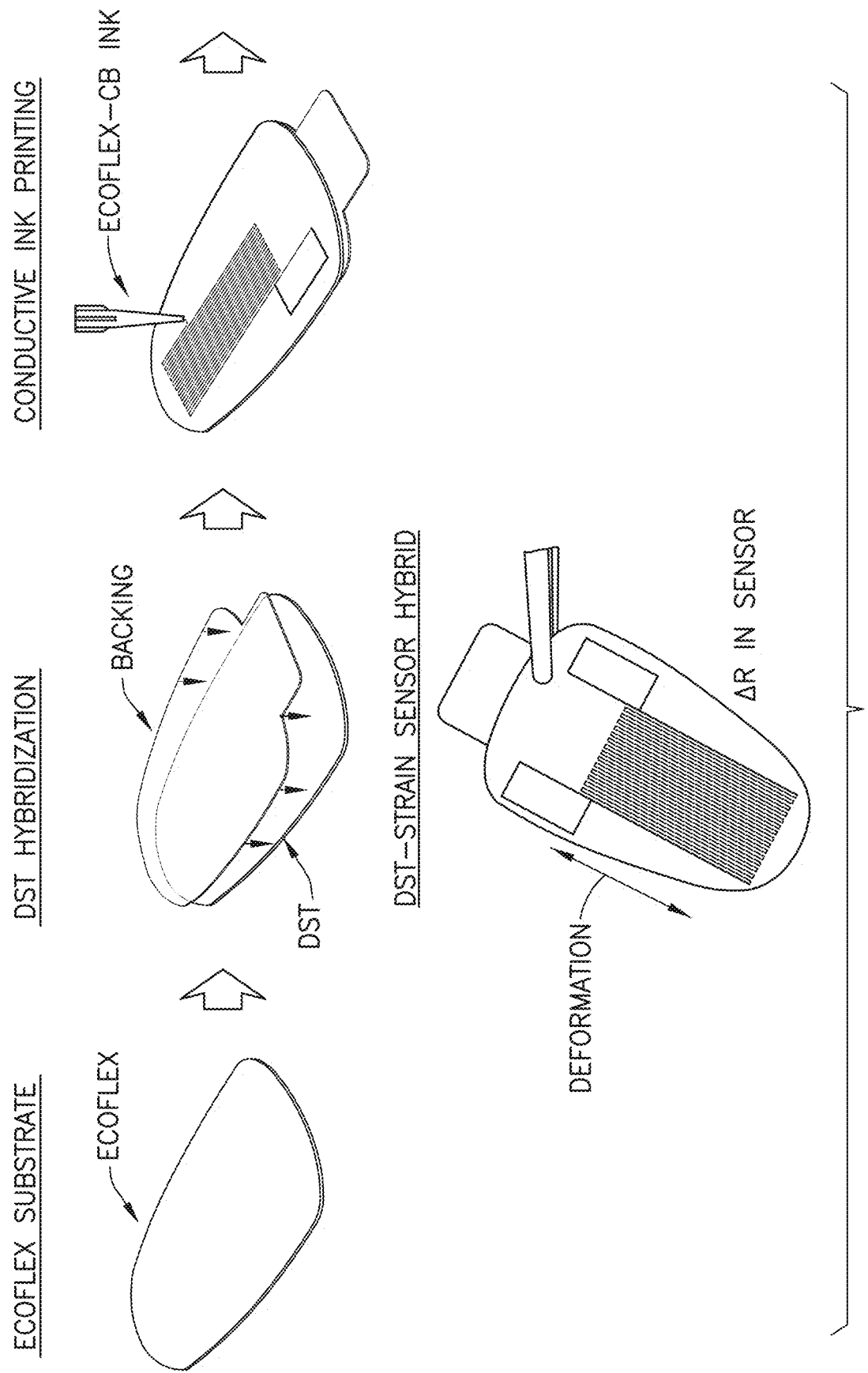
FIG. 19 schematically illustrates fabrication of a DST-strain sensor hybrid according to an embodiment of the present invention.

As another example, a stretchable strain sensor was adhered on the beating pig heart (FIG. 18C). The quick and strong adhesion by the dry adhesive material in the form of a DST (dry double sided tape) allows facile attachment of the strain sensor on the dynamic and curved surface of the beating pig heart as well as long-term electrical measurements of the heart movements (FIG. 18C). Notably, the stretchable DST-sensor hybrid was prepared by printing a conductive ink on a DST-Ecoflex hybrid substrate (FIG. 19), providing convenience in the application owing to its ready-to-use characteristic (FIG. 18C). In particular, as depicted in FIG. 19, the DST-strain sensor hybrid may be prepared by a using hydrogel-elastomer hybrids technique, wherein a strain sensor is fabricated by printing a conductive ink (such as an ink based on Ecoflex™ resin and carbon black (CB)). The resultant DST-strain sensor hybrid can readily be adhered on wet tissues and can measure deformations by monitoring changes in electrical resistance of the strain sensor (FIG. 18D). Such DST-device hybrids can potentially serve as a versatile platform for wearable and implantable devices to adhere on various parts of the human body.

Figure 20:
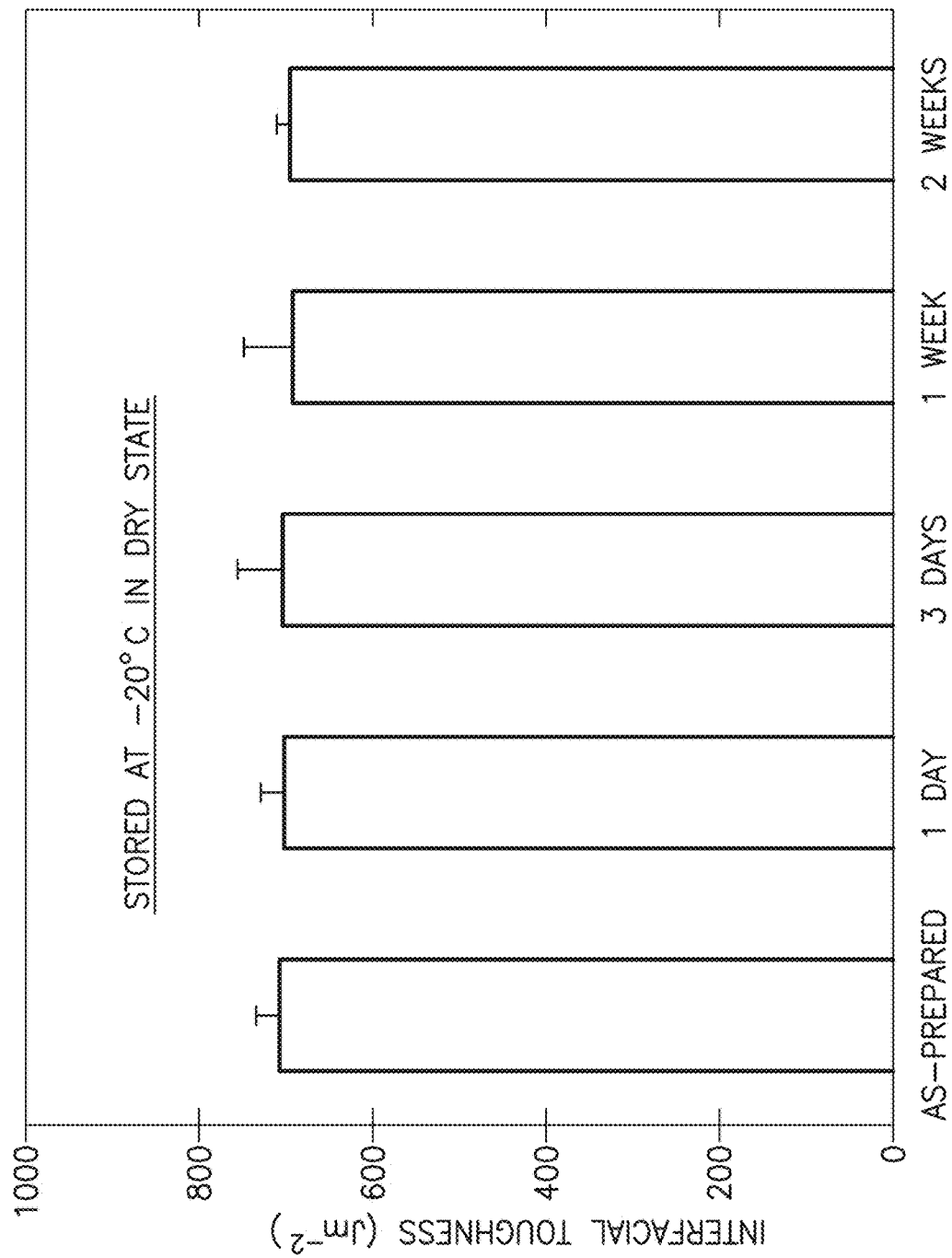
FIG. 20 graphically shows adhesion performance of a DST according to an embodiment of the present invention during long-term storage up to 2 weeks. Values represent the mean and the standard deviation (n=3-5).

Thus, the present invention provides an improved tissue adhesives in the form of a dry adhesive material, preferably in the form of a dry film or tape, such as a dry double sided film or tape (DST) based on a new dry cross linking mechanism which provides quick strong adhesion of diverse wet tissues and devices. The dry-preservable and ready-to-use nature of the adhesive material provides ease in storage, distribution, and usage for extended periods of time (e.g., over two weeks) without losing performances. This is demonstrated in FIG. 20, which graphically shows adhesion performance (interfacial toughness of the adhered material) between wet pig skins and the dry adhesive material stored at −20° C. in dry state for varying periods of time: as prepared, one day after preparation, three days after preparation, one week after preparation and two weeks after preparation.

As such, the present invention dry adhesive material eliminates the difficulties in storing perishable liquids or wet gels as well as mixing of reagents right before each use, common in existing tissue adhesives. Furthermore, the pre-set dry adhesive material is a simple composition, having high flexibility in fabrication, with a unique thin tape form. As such, it can provide substantial economic advantages, potentially facilitating the fast and widespread dissemination and translation of the material. These new capabilities of theory adhesive material address a set of long-lasting challenges in existing tissue adhesives and may offer new opportunities for future developments in tissue engineering, drug delivery, and bio-integrated devices. The new dry crosslinking mechanism for wet adhesion may further inspire the design of future adhesives in wet and underwater environments.

Materials and Methods for Experimental Data

Materials. All chemicals were obtained from Sigma-Aldrich otherwise mentioned and used without further purification. For preparation of the double-sided tape (DST), acrylic acid, gelatin methacrylate (type A bloom 90-100 from porcine skin with 60% substitution), acrylic acid N-hydroxysuccinimide ester (AAc-NHS), α-ketoglutaric acid, gelatin (type A bloom 300 from porcine skin), and chitosan (75-85% deacetylated) were used. In the examples, α-ketoglutaric acid is a photoinitiator used to polymerize monomers into polymer forms during the preparation. For visualization of the DST, red food dye (McCormick) and FITC-gelatin (Thermo Fisher Scientific) were used for photographs and microscope images, respectively. For in vitro biodegradation tests, Dulbecco's phosphate buffered saline (DPBS; with calcium and magnesium, Gibco), collagenase, lysozyme, and NAGase were used. For preparation of hydrogel, acrylamide and photoinitiator Irgacure 2959 (12959) were used. For surface functionalization of engineering solids, (3-aminopropyl) triethoxysilane (APTES) and hexamethyldiamine (HMDA) were used. For preparation of the stretchable strain sensor, Ecoflex 00-30 (Smooth-On), silicone curing retardant (SLO-JO, Smooth-On), and carbon black (Alfa Aesar) were used. All engineering solids were obtained from McMaster Carr otherwise mentioned. Pig skin, tendon, stomach, muscle, heart, liver, and blood were purchased from a local grocery store.

Preparation of the Dry Double-Sided Tape (DST).

The dry DST was prepared based on either gelatin or chitosan. To prepare the gelatin-based DST, 30 w/w % acrylic acid, 10 w/w % gelatin, 1 w/w % AAc-NHS, 0.1 w/w % gelatin methacrylate, and 0.2 w/w % α-ketoglutaric acid were dissolved in deionized water. The mixture was then filtered with 0.2 μm sterile syringe filters and poured on a glass mold with spacers. The DST was cured in a UV chamber (284 nm, 10 W power) for 20 min and completely dried under nitrogen flow. The dry DST was further soaked in ethanol for 12 h to leach out unreacted reagents and completely dried in vacuum chamber to remove ethanol. The final dry DST was sealed in plastic bags and stored in −20° C. before use. The chitosan-based DST was prepared by replacing 10 w/w % gelatin with 2 w/w % chitosan. In experiments, the gelatin-based DST with 210 μm as-prepared thickness was used unless otherwise mentioned. To prepare the DST in various shapes, a large sheet of dry DST was cut into each design by using a laser cutter (Epilog). Polyethylene-coated paper was used as backing for the DST. To aid visualization of the DST, 0.5 w/w % of red food dye (for photographs) or 0.2 w/w % FITC-gelatin (for fluorescent microscope images) were added into precursor solution of the DST before curing.

Mechanical Tests.

For tissue samples stored more than 1 hour before mechanical tests, the surface of samples was sprayed with aqueous 0.1 w/w % sodium azide solution after applying the DST and sealed in plastic bags to prevent degradation and dehydration of the tissues. All tissues and engineering solids were adhered by the DST after washout of the surfaces with water followed by 5 s pressing. To measure interfacial toughness, the adhered samples with 2.5 cm in width were prepared and tested by the standard 180-degree peeling test (ASTM F2256) or 90-degree peeling test (ASTM D2861) (for rigid substrate such as silicon) with a mechanical testing machine (2.5 kN load-cell, Zwick/Roell Z2.5). All tests were conducted with a constant peeling speed of 50 mm min'. The measured force reached a plateau as the peeling process entered the steady-state. Interfacial toughness was determined by dividing two times of the plateau force (for 180-degree peeling test) or the plateau force (for 90-degree peeling test) with the width of the tissue sample. Poly (methyl methacrylate) films (50 μm thickness, Goodfellow) were applied by using cyanoacrylate glues (Krazy Glue) as stiff backings for tissues and hydrogels.

To measure tensile strength, the adhered samples with adhesion area of 2.5 cm in width and 1 cm in length were prepared and tested by the standard lap-shear test (ASTM F2255) with the mechanical testing machine. All tests were conducted with a constant tensile speed of 50 mm min'. Shear strength was determined by dividing the maximum force with the adhesion area. Poly(methyl methacrylate) films were applied by using cyanoacrylate glues as stiff backings for tissues and hydrogels.

To measure tensile strength, the adhered samples with adhesion area of 2.5 cm in width and 2.5 cm in length were prepared and tested by the standard tensile test (ASTM F2258) with the mechanical testing machine. All tests were conducted with a constant tensile speed of 50 mm min'. Tensile strength was determined by dividing the maximum force with the adhesion area. Aluminum fixtures were applied by using cyanoacrylate glues to provide grips for tensile tests.

To characterize mechanical properties of the DST, the DST was equilibrated in DPBS before tests. Tensile property and fracture toughness of the DST were measured via pure-shear tensile tests of thin rectangular samples (10 mm in length, 30 mm in width, and 0.5 mm in thickness) with the mechanical testing machine (20 N load-cell, Zwick/Roell Z2.5). All tests were conducted with a constant tensile speed of 50 mm min'. The fracture toughness of the DST was calculated by following the previously reported method based on tensile tests of unnotched and notched samples with 1 cm notch length.

Preparation of Engineering Solids.

To prepare hydrogels for adhesion tests of engineering solids, 20 w/w % acrylamide, 10 w/w % gelatin, 0.2 w/w % gelatin methacrylate, and 0.5 w/w % 12959 were dissolved in deionized water. The mixture was then filtered with 0.2 μm sterile syringe filters and poured on a glass mold with spacers. The hydrogels were cured in a UV chamber (284 nm, 10 W power) for 60 min. To facilitate covalent coupling with the DST, engineering solids except hydrogel were functionalized with primary amines. For silicon, titanium, and PDMS, the substrates were first treated with oxygen plasma for 2 min (30 W power, Harrick Plasma) to activate the surface. Subsequently, the plasma-treated substrates were covered with the APTES solution (1 w/w % APTES in 50% ethanol) and incubated for 3 h at room temperature. The substrates were then thoroughly washed with isopropyl alcohol and dried with nitrogen flow. For polyimide and polycarbonate, the substrates were immersed into the HMDA solution (10 v/v % in deionized water) for 24 h at room temperature. The substrates were then thoroughly washed with deionized water and dried with nitrogen flow.

In Vitro Biodegradation Tests.

In vitro biodegradation tests of the DST were conducted based on enzymatic degradation media following the previously reported protocol (See Boutry, C. M. et al. A stretchable and biodegradable strain and pressure sensor for orthopaedic application. *Nature Electronics* 1, 314-321 (2018)). To prepare in vitro enzymatic biodegradation media for the gelatin-based DST, 5 mg collagenase was added in 100 mL DPBS. To prepare in vitro enzymatic biodegradation media for the chitosan-based DST, 5 mg collagenase, 5 mg lysozyme, and 10 μL of 1 mg mL$^{-1}$ NAGase aqueous solution were added in 100 mL DPBS. The dry DST was cut into small samples (10 mm in width and 10 mm in length) and accurately weighed. Before immersion in the enzymatic media, the samples were sterilized in 75% ethanol for 15 min and washed three times with DPBS. Each sample was then immersed in 15 mL of the enzymatic media within glass scintillation vials and incubated at 37° C. with 60 rpm shaking. About 0.01 w/v % sodium azide was added into the enzymatic media to prevent growth of any microorganism during the tests. At each time interval, the DST was removed from the incubation media, exhaustively washed with deionized water, and lyophilized. Weight-loss was determined as a percent ratio of mass of the lyophilized sample at each time interval normalized by the dry-mass of the original sample.

In Vitro Biocompatibility Tests.

In vitro biocompatibility tests were conducted by using the DST-conditioned media for cell culture (See Darnell, M. C. et al. Performance and biocompatibility of extremely tough alginate/polyacrylamide hydrogels. *Biomaterials* 34, 8042-8048 (2013)). To prepare the DST-conditioned media for in vitro biocompatibility tests, 20 mg of the DST was incubated in 1 mL Dulbecco's modified eagle medium (DMEM) at 37° C. for 24 h. The pristine DMEM was used as a control. Wild-type mouse embryonic fibroblasts (mEFs) were plated in 96-well plate (N=10 per each case). The cells were then treated with the DST-conditioned media and incubated at 37° C. for 24 h in 5% CO2. The cell viability was determined with a Live/Dead viability/cytotoxicity kit for mammalian cells (Thermo Fisher Scientific) by adding 4 μM calcein and ethidium homodimer-1 into the culture media. A confocal microscope (SP 8, Leica) was used to image live cells with excitation/emission at 495 nm/515 nm, and dead cells at 495 nm/635 nm, respectively.

Preparation of the DST-Strain Sensor Hybrid.

The DST-strain sensor hybrid was prepared by printing a conductive ink onto a DST-elastomer hybrid substrate. An elastomer substrate was first prepared by casting Ecoflex 00-30 resin into a laser-cut acrylic mold. Subsequently, a thin layer of DST (100 μm dry thickness) was introduced on the bottom side of the Ecoflex substrate following the previously reported protocol for hydrogel-elastomer hybrids (See Yamagishi, K. et al. Tissue-adhesive wirelessly powered optoelectronic device for metronomic photodynamic cancer therapy. *Nature Biomedical Engineering* 3, 27-36 (2019)). The strain sensor was fabricated by printing the conductive ink onto the DST-Ecoflex hybrid substrate by using a custom direct ink writing (DIW) 3D printer (See Yuk, H. & Zhao, X. A new 3d printing strategy by harnessing deformation, instability, and fracture of viscoelastic inks. *Advanced Materials* 30, 1704028 (2018)). Briefly, the conductive ink was prepared by mixing 10 w/w % carbon black and 1 w/w % silicone curing retardant into Ecoflex 00-30 resin via a planetary mixer (AR100, Thinky). The printing paths were generated via production of G-codes that control the XYZ motions of a robotic gantry (Aerotech). A pressure-based microdispenser (Ultimus V, Nordson EFD) was used to print the conductive ink with a 200 μm diameter nozzle (Smoothflow tapered tip, Nordson EFD) on the substrate via a custom LabVIEW interface (National Instruments). The deformation-induced changes in electrical resistance of the strain sensor were monitored by a digital multimeter (34450A, Keysight).

Instant Sealing of Pig Lung.

This ex vivo experiment was conducted by using a fresh pig lung purchased from a local grocery store. Cuts were made on the pig trachea and lung lobe by a razor blade. A tube was then connected to the pig trachea to inflate and deflate the pig lung (at pressure of 3 kPa or 22.5 mmHg). A hydrogel patch (2.5 cm in width and 5 cm in length) was adhered on the damaged pig trachea and lung lobe by the DST with 5 s pressing to instantly seal the cuts. The sealed pig lung was kept for 12 h at room temperature to monitor robustness of the DST-based instant sealing in long-term.

Instant Sealing of Pig Stomach.

This ex vivo experiment was conducted by using a fresh pig stomach purchased from a local grocery store. A 10 mm-diameter hole was punched on the pig stomach. A tube with flowing water was then connected to the pig stomach to allow continuous water flow through the hole. A hydrogel patch with 40 mm-diameter was adhered on the damaged pig stomach by the DST with 5 s pressing to instantly seal the hole. The sealed pig stomach was kept for 12 h at room temperature to monitor robustness of the DST-based instant sealing in long-term.

Instant Adhesion of Devices on a Beating Pig Heart.

These ex vivo experiments were conducted by using a fresh pig heart purchased from a local grocery store. Programmed pressurized air inputs were introduced into the pig heart by using the microdispenser to mimic heart beats. All devices were adhered on the beating pig heart after washout of the surfaces with water followed by 5 s pressing. To prevent dehydration and degradation, a wet towel soaked with aqueous 0.1 w/w % sodium azide solution was covered on the beating pig heart for experiments longer than 1 h in ambient condition. For the instant strong adhesion of a drug-delivery device, a cut was introduced on the pig heart. To prepare the drug-delivery device, 0.5 w/w % fluorescein sodium salt was added as a mock-drug into a hydrogel patch (2.5 cm in width and 5 cm in length). The drug-loaded hydrogel patch was then stretched to fit the cut and adhered on the beating pig heart by the perforated DST. The adhered drug patch on the beating pig heart was kept for 12 h at room temperature to allow diffusion of the mock-drug into the heart tissue. The diffusion of the mock-drug was imaged by using a fluorescence microscope (LV100ND, Nikon). For the instant strong adhesion of a strain sensor, the DST-strain sensor hybrid was adhered on the beating pig heart after removing the backing. The adhered strain sensor on the beating pig heart was kept for 12 h at room temperature, and then connected with the digital multimeter to monitor the deformation of the beating heart.

The present invention provides a new type of tissue adhesives in the form of a dry double-sided tape (DST) to address the limitations with currently available materials and methods for adhering tissues and attaching devices to tissues. The present invention dry adhesive material, together with its dry cross linking mechanism, is particularly desirable for instant adhesion of various tissues, due to the intrinsically wet nature of biological tissues and frequent introduction of water on tissue surfaces during surgical processes (e.g., washout or irrigation with water). As a result, the adhesion formation between various wet tissues (skin, tendon, stomach, muscle, heart, and liver) and engineering solids (hydrogel, silicon, titanium, polydimethylsiloxane, polyimide, and polycarbonate) occurs much more quickly than with existing materials and mechanisms (e.g., less than 1 minute and even as quickly as less than 5 seconds) with excellent interfacial toughness (e.g., on the order of up to 1,150 J m$^{-2}$), and improved shear and tensile strengths (e.g., on the order of up to 160 kPa). Further, as demonstrated, the present dry adhesive material has shear moduli and stretchability similar to that of soft tissues. Still further, the biocompatibility of the dry adhesive-conditioned media is comparable to that of the control media, and the biodegradation rate of the dry adhesive material is controllable by tuning its composition without appreciable depreciation in its properties. The present dry adhesive material further demonstrated unprecedented functions in ex vivo experiments including sealing an air-leaking pig lung and a fluid-leaking pig stomach, was well as adhering a drug patch and a strain sensor on a beating pig heart.

What is claimed is:

1. A dry adhesive material for adhering one or more wet surfaces comprising:
   (i) one or more hydrophilic polymers;
   (ii) one or more amine coupling groups, and
   (iii) one or more cross linkers,
   wherein, the dry adhesive material is in the form of a film or tape having a top surface and a bottom surface, and
   wherein the dry adhesive material has a liquid content such that placement of one or more of the top and/or bottom surfaces of the dry adhesive material in contact with the one or more wet surfaces causes the dry adhesive material to absorb liquid from the one or more wet surfaces, swell to form temporary crosslinking between the dry adhesive material and the wet surface, and form covalent crosslinking between the one or more amine coupling groups and the one or more wet surfaces,
   wherein the dry adhesive material further comprises poly(acrylic acid) grafted with N-hydroxysuccinimide ester, crosslinked by biodegradable gelatin methacrylate, and further comprising one or more biodegradable biopolymers.

2. The dry adhesive material of claim 1, wherein the (ii) one or more amine coupling groups are selected from N-hydroxysuccinimide ester, N-hydroxysulfosuccinimide ester, aldehyde, imidoester, epoxide, isocyanate, catechol, and combinations thereof.

3. The dry adhesive material of claim 1, wherein the (iii) one or more crosslinkers are selected from gelatin methacrylate, hyaluronic acid methacrylate, oxidized methacrylic alginate, polycaprolactone diacrylate,N,N'-bis(acryloyl) cystamine, N,N'-methylenebis(acrylamide), polyethylene glycol diacrylate, polyethylene glycol dimethacrylate, and combinations thereof.

4. The dry adhesive material of claim 1, wherein the one or more biodegradable biopolymers are selected from gelatin, chitosan, and combination thereof.

5. The dry adhesive material of claim 1, wherein negatively charged carboxylic acid groups in the poly(acrylic acid) grafted with N-hydroxysuccinimide ester facilitate absorption of liquid and swelling of the dry adhesive material and further form intermolecular bonds with the one or more wet tissue surfaces within less than 60 seconds after contact between the dry adhesive material and the one or more wet surfaces.

6. The dry adhesive material of claim 1, wherein the N-hydroxysuccinimide ester grafted in the poly(acrylic acid) forms covalent coupling with primary amine groups present on the one or more wet surfaces.

7. The dry adhesive material of claim 1, wherein after the covalent crosslinking is formed between the one or more amine coupling groups and the one or more wet surfaces, the swollen dry adhesive material transforms into a layer of a hydrogel.

8. The dry adhesive of claim 7, wherein the hydrogel has a fracture toughness of at least 1,000 J m$^{-2}$.

9. The dry adhesive material of claim 1 in the form of a flat sheet, a perforated sheet, a double sided tape or film, and a perforated double sided tape or film.

10. The dry adhesive material of claim 9, wherein the dry adhesive material comprises a top surface and a bottom surface, and wherein adhesive material further comprises one or more backing material layers disposed on at least one of the top surface and bottom surface.

11. The dry adhesive material of claim 10, wherein the backing material is a removable backing material and is fabricated of polyethylene, a hydrophobic polymer-coated paper, poly(methyl methacrylate), a hydrophobic polymer film, or combinations thereof.

12. The dry adhesive material of claim 10, wherein the backing material is a non-removable material layer and is fabricated of silicone elastomer, thermoplastic polyurethane, hydrogel, a biocompatible material that is non-adhesive to wet tissues, or combinations thereof.

13. The dry adhesive material of claim 1, further comprising one or more engineering solids, and/or devices adhered to one or more surfaces of the dry adhesive material.

14. The dry adhesive material of claim 13, wherein the one or more engineering solids are selected from hydrogel, silicon, titanium, polydimethylsiloxane, polyimide, polycarbonate, and combination thereof.

15. The dry adhesive material of claim 1, wherein the dry adhesive material is biodegradable.

16. The dry adhesive material of claim 15, wherein the (i) one or more polymers and/or the (iii) one or more crosslinkers are selected so as to modify biodegradability properties.

* * * * *